United States Patent
Ashby et al.

(10) Patent No.: US 10,433,612 B2
(45) Date of Patent: Oct. 8, 2019

(54) PRESSURE SENSOR TO QUANTIFY WORK

(71) Applicant: ICON Health & Fitness, Inc., Logan, UT (US)

(72) Inventors: Darren C. Ashby, Richmond, UT (US); Scott R. Watterson, Logan, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 556 days.

(21) Appl. No.: 14/641,663

(22) Filed: Mar. 9, 2015

(65) Prior Publication Data

US 2015/0253210 A1   Sep. 10, 2015

Related U.S. Application Data

(60) Provisional application No. 61/950,606, filed on Mar. 10, 2014.

(51) Int. Cl.
*A43B 5/14* (2006.01)
*A43B 3/00* (2006.01)
(Continued)

(52) U.S. Cl.
CPC .............. *A43B 5/14* (2013.01); *A43B 3/0005* (2013.01); *A43B 3/0015* (2013.01); *A61B 5/6807* (2013.01); *F03G 5/06* (2013.01); *G01L 1/142* (2013.01); *A63B 21/008* (2013.01); *A63B 21/0085* (2013.01); *A63B 21/012* (2013.01); *A63B 21/22* (2013.01); *A63B 22/0046* (2013.01); *A63B 22/0056* (2013.01); *A63B 22/0605* (2013.01); *A63B 2220/20* (2013.01); *A63B 2220/30* (2013.01); *A63B 2220/40* (2013.01); *A63B 2220/51* (2013.01); *A63B 2220/56* (2013.01); *A63B 2225/50* (2013.01); *A63B 2230/06* (2013.01); *A63B 2230/207* (2013.01); *A63B 2230/30* (2013.01); *A63B 2230/75* (2013.01); *B62J 2099/002* (2013.01);
(Continued)

(58) Field of Classification Search
CPC ........................................................ A43B 5/14
USPC ........................................................ 702/41
See application file for complete search history.

(56) References Cited

U.S. PATENT DOCUMENTS 232,022 A   9/1880   Gifford
284,294 A   9/1883   Graves
(Continued)

FOREIGN PATENT DOCUMENTS

| TW | M424795 | 3/2012 |
|---|---|---|
| TW | M441216 | 2/2013 |
| WO | 2009082215 | 7/2009 |

OTHER PUBLICATIONS

International Search Report issued for PCT/US2015/019492 dated May 22, 2015.
(Continued)

*Primary Examiner* — Igwe U Anya
(74) *Attorney, Agent, or Firm* — Maschoff Brennan

(57) ABSTRACT

A monitoring system includes a shoe and a sole integrated into the shoe. The monitoring system also includes a connection mechanism attached to an underside of the sole and is shaped to connect the sole to a pedal. A pressure sensor is incorporated into the shoe that senses a force exerted on the pedal when the shoe is connected to the pedal through the connection mechanism.

20 Claims, 6 Drawing Sheets

(51) Int. Cl.
*A61B 5/00* (2006.01)
*G01L 1/14* (2006.01)
*F03G 5/06* (2006.01)
*A63B 21/008* (2006.01)
*A63B 21/012* (2006.01)
*A63B 21/22* (2006.01)
*A63B 22/06* (2006.01)
*A63B 22/00* (2006.01)
*B62M 3/08* (2006.01)
*B62M 6/50* (2010.01)
*B62J 99/00* (2009.01)

(52) U.S. Cl.
CPC ............ *B62K 2207/00* (2013.01); *B62M 3/08* (2013.01); *B62M 6/50* (2013.01)

(56) References Cited

U.S. PATENT DOCUMENTS

| | | |
|---|---|---|
| 321,388 A | 6/1885 | Ruebsam |
| 339,638 A | 4/1886 | Goldie |
| 348,493 A | 8/1886 | Greene |
| 421,779 A | 2/1890 | Steven |
| 447,780 A | 3/1891 | Luge |
| 450,792 A | 4/1891 | Dodd |
| 470,837 A | 3/1892 | Hart |
| 549,084 A | 10/1895 | Whitaker |
| 601,307 A | 3/1898 | Salisbury |
| 659,216 A | 10/1900 | Dowling |
| 663,486 A | 12/1900 | Boren |
| 674,391 A | 5/1901 | Baker |
| 683,284 A | 9/1901 | Honey |
| 766,930 A | 8/1904 | Clemons |
| 881,521 A | 3/1908 | Wilson |
| 897,722 A | 9/1908 | Day |
| 931,394 A | 8/1909 | Day |
| 937,795 A | 10/1909 | Hackney |
| 1,016,729 A | 2/1912 | Barrett |
| 1,020,777 A | 3/1912 | Peterson |
| 1,064,968 A | 6/1913 | Hagen |
| 1,082,940 A | 12/1913 | Flora |
| 1,211,765 A | 1/1917 | Schmidt |
| 1,570,482 A | 1/1926 | Hale |
| 1,580,530 A | 4/1926 | Rambo |
| 1,585,748 A | 5/1926 | Wendelken |
| 1,715,870 A | 6/1929 | Augustine |
| 1,766,089 A | 6/1930 | Wood |
| 1,778,635 A | 10/1930 | Heisler |
| 1,824,406 A | 9/1931 | Petersime |
| 1,850,530 A | 3/1932 | Brown |
| 1,893,728 A | 1/1933 | Bullis |
| 1,902,694 A | 3/1933 | Edwards |
| 1,919,627 A | 7/1933 | Fitz Gerald |
| 1,928,089 A | 9/1933 | Blickman |
| 1,930,416 A | 10/1933 | Chauvot |
| 1,973,945 A | 9/1934 | Chavin |
| 1,978,579 A | 10/1934 | Hooks |
| 1,982,843 A | 12/1934 | Traver |
| 2,067,136 A | 1/1937 | Bridenbaugh |
| 2,117,957 A | 5/1938 | Ritter |
| 2,165,700 A | 7/1939 | Henry |
| 2,177,957 A | 10/1939 | Stewart |
| 2,219,219 A | 10/1940 | Boger |
| 2,247,946 A | 7/1941 | Hein et al. |
| 2,255,864 A | 9/1941 | Stephens |
| 2,315,485 A | 4/1943 | Le Roy |
| 2,399,915 A | 5/1946 | Drake |
| 2,413,841 A | 1/1947 | Minuto |
| 2,440,644 A | 4/1948 | Powell |
| 2,569,007 A | 9/1951 | Klyce |
| 2,632,645 A | 3/1953 | Barkschat |
| 2,645,539 A | 7/1953 | Thompson |
| 2,646,282 A | 7/1953 | Ringman |
| 2,648,540 A | 8/1953 | Hunter |
| 2,674,453 A | 4/1954 | Hummert |
| 2,743,623 A | 5/1956 | Wells |
| 2,746,822 A | 5/1956 | Copenhaver |
| 2,779,139 A | 1/1957 | Boettcher |
| 2,842,365 A | 7/1958 | Kelley |
| 2,855,200 A | 10/1958 | Blickman |
| 2,874,971 A | 2/1959 | Devery |
| 2,906,532 A | 9/1959 | Echols |
| 2,969,060 A | 1/1961 | Swanda |
| 2,984,594 A | 5/1961 | Runton |
| 3,035,671 A | 5/1962 | Sicherman |
| 3,059,312 A | 10/1962 | Jamieson |
| 3,068,950 A | 12/1962 | Davidson |
| 3,072,426 A | 1/1963 | Gilbert |
| 3,112,108 A | 11/1963 | Hanke |
| 3,127,171 A | 3/1964 | Noland et al. |
| 3,179,071 A | 4/1965 | Johnston |
| 3,193,287 A | 7/1965 | Robinson |
| 3,205,888 A | 9/1965 | Stroop |
| 3,316,898 A | 5/1967 | Brown |
| 3,319,273 A | 5/1967 | Lawrence |
| 3,342,485 A | 9/1967 | Gaul |
| 3,345,067 A | 10/1967 | Smith |
| 3,358,813 A | 12/1967 | Kohlhagen |
| 3,378,259 A | 4/1968 | Kupchinski |
| 3,394,934 A | 7/1968 | Petros |
| 3,408,067 A | 10/1968 | Armstrong |
| 3,408,069 A | 10/1968 | Lewis |
| 3,411,497 A | 11/1968 | Rickey et al. |
| 3,416,174 A | 12/1968 | Novitske |
| 3,424,005 A | 1/1969 | Brown |
| 3,430,507 A | 3/1969 | Hurst et al. |
| 3,432,164 A | 3/1969 | Deeks |
| 3,438,627 A | 4/1969 | La Lanne |
| 3,444,830 A | 5/1969 | Doetsch |
| 3,446,503 A | 5/1969 | Lawton |
| 3,501,140 A | 3/1970 | Eichorn |
| 3,511,500 A | 5/1970 | Dunn |
| 3,514,110 A | 5/1970 | Thomander |
| 3,518,985 A | 7/1970 | Quinton |
| 3,547,435 A | 12/1970 | Scott |
| 3,554,541 A | 1/1971 | Spoth |
| 3,563,541 A | 2/1971 | Sanquist |
| 3,566,861 A | 3/1971 | Weiss |
| 3,567,219 A | 3/1971 | Foster |
| 3,568,669 A | 3/1971 | Stites |
| 3,572,700 A | 3/1971 | Mastropaolo |
| 3,583,465 A | 6/1971 | Youngs et al. |
| 3,586,322 A | 6/1971 | Kverneland |
| 3,589,715 A | 6/1971 | Mark |
| 3,592,466 A | 7/1971 | Parsons |
| 3,598,404 A | 8/1971 | Bowman |
| 3,602,502 A | 8/1971 | Jaegar |
| 3,606,320 A | 9/1971 | Erwin, Jr. |
| 3,608,898 A | 9/1971 | Berlin |
| 3,614,097 A | 10/1971 | Blickman |
| 3,628,654 A | 12/1971 | Haracz |
| 3,628,791 A | 12/1971 | Garcia |
| 3,634,895 A | 1/1972 | Childers |
| 3,636,577 A | 1/1972 | Nissen |
| 3,638,941 A | 2/1972 | Kulkens |
| 3,640,528 A | 2/1972 | Proctor |
| 3,641,601 A | 2/1972 | Sieg |
| 3,642,279 A | 2/1972 | Cutter |
| 3,643,943 A | 2/1972 | Erwin, Jr. et al. |
| 3,650,529 A | 3/1972 | Salm |
| 3,658,327 A | 4/1972 | Thiede |
| 3,659,845 A | 5/1972 | Quinton |
| 3,664,666 A | 5/1972 | Lloyd |
| 3,686,776 A | 8/1972 | Dahl |
| 3,689,066 A | 9/1972 | Hagen |
| 3,703,284 A | 11/1972 | Hesen |
| 3,708,166 A | 1/1973 | Annas |
| 3,709,197 A | 1/1973 | Moseley |
| 3,728,940 A | 4/1973 | Peterson |
| 3,731,917 A | 5/1973 | Townsend |
| 3,738,649 A | 6/1973 | Miller |
| 3,741,538 A | 6/1973 | Useldinger |
| 3,744,480 A | 7/1973 | Gause et al. |
| 3,744,712 A | 7/1973 | Papadopoulos |

(56) References Cited

U.S. PATENT DOCUMENTS

| | | |
|---|---|---|
| 3,744,794 A | 7/1973 | Gause et al. |
| 3,751,033 A | 8/1973 | Rosenthal |
| 3,756,595 A | 9/1973 | Hague |
| 3,767,195 A | 10/1973 | Dimick |
| 3,782,718 A | 1/1974 | Saylor |
| 3,788,412 A | 1/1974 | Vincent |
| 3,792,860 A | 2/1974 | Selnes |
| 3,802,698 A | 4/1974 | Burian et al. |
| 3,809,393 A | 5/1974 | Jones |
| 3,814,420 A | 6/1974 | Encke |
| 3,818,194 A | 6/1974 | Biro |
| 3,822,488 A | 7/1974 | Johnson |
| 3,822,599 A | 7/1974 | Brentham |
| 3,826,491 A | 7/1974 | Elder |
| 3,834,696 A | 9/1974 | Spector |
| 3,845,756 A | 11/1974 | Olsson |
| 3,848,467 A | 11/1974 | Flavell |
| 3,851,874 A | 12/1974 | Wilkin |
| 3,858,938 A | 1/1975 | Kristensson et al. |
| 3,859,840 A | 1/1975 | Gause |
| 3,861,215 A | 1/1975 | Bradley |
| 3,869,121 A | 3/1975 | Flavell |
| 3,870,297 A | 3/1975 | Elder |
| 3,874,657 A | 4/1975 | Niebojewski |
| 3,880,274 A | 4/1975 | Bechtloff |
| 3,883,922 A | 5/1975 | Fleischhauer |
| 3,892,404 A | 7/1975 | Martucci |
| 3,901,379 A | 8/1975 | Bruhm |
| 3,902,480 A | 9/1975 | Wilson |
| 3,903,613 A | 9/1975 | Bisberg |
| 3,904,196 A | 9/1975 | Berlin |
| 3,909,857 A | 10/1975 | Herrera |
| 3,912,263 A | 10/1975 | Yatso |
| 3,918,710 A | 11/1975 | Niebojewski |
| 3,926,430 A | 12/1975 | Good |
| 3,929,026 A | 12/1975 | Hofmann |
| 3,938,400 A | 2/1976 | Konyha |
| 3,941,377 A | 3/1976 | Lie |
| 3,948,513 A | 4/1976 | Pfotenhauer |
| 3,963,101 A | 6/1976 | Stadelmann et al. |
| 3,974,491 A | 8/1976 | Sipe |
| 3,977,451 A | 8/1976 | Duba |
| 3,981,500 A | 9/1976 | Ryan |
| 4,012,015 A | 3/1977 | Nelson et al. |
| 4,020,795 A | 5/1977 | Marks |
| 4,024,949 A | 5/1977 | Kleysteuber et al. |
| 4,026,545 A | 5/1977 | Schonenberger |
| 4,027,531 A | 6/1977 | Dawson |
| 4,033,567 A | 7/1977 | Lipfert |
| 4,056,265 A | 11/1977 | Ide |
| 4,063,726 A | 12/1977 | Wilson |
| 4,063,727 A | 12/1977 | Hall |
| 4,066,257 A | 1/1978 | Moller |
| 4,066,259 A | 1/1978 | Brentham |
| 4,067,372 A | 1/1978 | Masson |
| 4,071,235 A | 1/1978 | Zent |
| 4,072,309 A | 2/1978 | Wilson |
| 4,077,626 A | 3/1978 | Newman |
| 4,082,267 A | 4/1978 | Flavell |
| 4,093,196 A | 6/1978 | Bauer |
| 4,094,330 A | 6/1978 | Jong |
| 4,111,417 A | 9/1978 | Gardner |
| 4,112,928 A | 9/1978 | Putsch |
| 4,113,071 A | 9/1978 | Muller et al. |
| 4,120,294 A | 10/1978 | Wolfe |
| 4,120,924 A | 10/1978 | Rainville |
| 4,141,158 A | 2/1979 | Benseler et al. |
| 4,146,222 A | 3/1979 | Hribar |
| 4,149,714 A | 4/1979 | Lambert, Jr. |
| 4,151,988 A | 5/1979 | Nabinger |
| 4,151,994 A | 5/1979 | Stalberger, Jr. |
| 4,161,998 A | 7/1979 | Trimble |
| 4,167,938 A | 9/1979 | Remih |
| 4,168,061 A | 9/1979 | Gordon |
| 4,171,805 A | 10/1979 | Abbott |
| 4,179,134 A | 12/1979 | Atkinson |
| 4,183,156 A | 1/1980 | Rudy |
| 4,183,494 A | 1/1980 | Cleveland |
| 4,188,030 A | 2/1980 | Hooper |
| 4,199,139 A | 4/1980 | Mahnke |
| 4,204,673 A | 5/1980 | Speer, Sr. |
| 4,208,049 A | 6/1980 | Wilson |
| 4,215,516 A | 8/1980 | Huschle et al. |
| 4,216,856 A | 8/1980 | Moring et al. |
| 4,220,996 A | 9/1980 | Searcy |
| 4,227,689 A | 10/1980 | Keiser |
| 4,235,437 A | 11/1980 | Ruis et al. |
| 4,236,239 A | 11/1980 | Imgruth et al. |
| 4,239,092 A | 12/1980 | Janson |
| 4,240,627 A | 12/1980 | Brentham |
| 4,248,476 A | 2/1981 | Phelps |
| 4,249,725 A | 2/1981 | Mattox |
| 4,251,932 A | 2/1981 | Love |
| 4,253,661 A | 3/1981 | Russell |
| 4,258,821 A | 3/1981 | Wendt |
| 4,258,913 A | 3/1981 | Brentham |
| 4,274,625 A | 6/1981 | Gaetano |
| 4,278,095 A | 7/1981 | Lapeyre |
| 4,278,249 A | 7/1981 | Forrest |
| 4,286,782 A | 9/1981 | Fuhrhop |
| 4,290,601 A | 9/1981 | Mittelstadt |
| 4,298,893 A | 11/1981 | Holmes |
| 4,300,761 A | 11/1981 | Howard |
| 4,301,808 A | 11/1981 | Taus |
| 4,313,602 A | 2/1982 | Sullivan |
| 4,313,603 A | 2/1982 | Simjian |
| 4,322,609 A | 3/1982 | Kato |
| 4,323,237 A | 4/1982 | Jungerwirth |
| 4,324,501 A | 4/1982 | Herbenar |
| 4,333,978 A | 6/1982 | Kocher |
| 4,334,676 A | 6/1982 | Schonenberger |
| 4,334,695 A | 6/1982 | Ashby |
| 4,337,283 A | 6/1982 | Haas, Jr. |
| 4,337,529 A | 6/1982 | Morokawa |
| 4,342,452 A | 8/1982 | Summa |
| 4,344,616 A | 8/1982 | Ogden |
| 4,349,597 A | 9/1982 | Fine et al. |
| 4,350,336 A | 9/1982 | Hanford |
| 4,354,676 A | 10/1982 | Ariel |
| 4,355,645 A | 10/1982 | Mitani et al. |
| 4,358,105 A | 11/1982 | Sweeney, Jr. |
| 4,363,480 A | 12/1982 | Fisher et al. |
| 4,363,486 A | 12/1982 | Chaudhry |
| 4,367,895 A | 1/1983 | Pacitti et al. |
| 4,369,081 A | 1/1983 | Curry et al. |
| 4,370,766 A | 2/1983 | Herzig et al. |
| 4,374,587 A | 2/1983 | Ogden |
| 4,377,045 A | 3/1983 | Aurensan |
| 4,378,111 A | 3/1983 | Tsuchida et al. |
| 4,383,684 A | 5/1983 | Schliep |
| 4,383,714 A | 5/1983 | Ishida |
| 4,389,047 A | 6/1983 | Hall |
| 4,397,462 A | 8/1983 | Wilmarth |
| 4,406,451 A | 9/1983 | Gaetano |
| 4,408,613 A | 10/1983 | Relyea |
| 4,422,635 A | 12/1983 | Herod |
| 4,422,636 A | 12/1983 | de Angeli |
| 4,423,630 A | 1/1984 | Morrison |
| 4,423,864 A | 1/1984 | Wiik |
| 4,426,077 A | 1/1984 | Becker |
| 4,431,181 A | 2/1984 | Baswell |
| 4,434,981 A | 3/1984 | Norton |
| 4,441,708 A | 4/1984 | Brentham |
| 4,445,684 A | 5/1984 | Ruff |
| 4,452,448 A | 6/1984 | Ausherman |
| 4,453,766 A | 6/1984 | DiVito |
| 4,461,472 A | 7/1984 | Martinez |
| 4,465,277 A | 8/1984 | Dittrich |
| 4,476,582 A | 10/1984 | Strauss et al. |
| 4,477,071 A | 10/1984 | Brown et al. |
| 4,480,831 A | 11/1984 | Muller-Deinhardt |
| 4,489,933 A | 12/1984 | Fisher |
| 4,491,318 A | 1/1985 | Francke |
| 4,493,561 A | 1/1985 | Bouchet |

(56) References Cited

U.S. PATENT DOCUMENTS

| | | |
|---|---|---|
| 4,494,662 A | 1/1985 | Clymer |
| 4,495,560 A | 1/1985 | Sugimoto et al. |
| 4,496,147 A | 1/1985 | DeCloux et al. |
| 4,499,784 A | 2/1985 | Shum |
| 4,502,679 A | 3/1985 | De Lorenzo |
| 4,504,055 A | 3/1985 | Wells |
| 4,504,968 A | 3/1985 | Kaneko et al. |
| 4,505,474 A | 3/1985 | Mattox |
| 4,505,475 A | 3/1985 | Olschansky et al. |
| 4,509,510 A | 4/1985 | Hook |
| 4,512,566 A | 4/1985 | Bicocchi |
| 4,512,567 A | 4/1985 | Phillips |
| 4,512,571 A | 4/1985 | Hermelin |
| 4,515,988 A | 5/1985 | Bayer et al. |
| 4,519,603 A | 5/1985 | Decloux |
| 4,522,394 A | 6/1985 | Broussard |
| 4,529,194 A | 7/1985 | Haaheim |
| 4,529,196 A | 7/1985 | Logan |
| 4,533,136 A | 8/1985 | Smith et al. |
| 4,536,244 A | 8/1985 | Greci et al. |
| 4,537,396 A | 8/1985 | Hooper |
| 4,538,805 A | 9/1985 | Parviainen |
| 4,542,897 A | 9/1985 | Melton |
| 4,542,899 A | 9/1985 | Hendricks |
| 4,544,152 A | 10/1985 | Taitel |
| 4,544,153 A | 10/1985 | Babcock |
| 4,546,971 A | 10/1985 | Raasoch |
| 4,548,405 A | 10/1985 | Lee |
| 4,549,044 A | 10/1985 | Durham |
| 4,549,733 A | 10/1985 | Salyer |
| 4,555,108 A | 11/1985 | Monteiro |
| 4,556,216 A | 12/1985 | Pitkanen |
| 4,563,001 A | 1/1986 | Terauds |
| 4,563,003 A | 1/1986 | Bugallo et al. |
| 4,564,193 A | 1/1986 | Stewart |
| 4,566,461 A | 1/1986 | Lubell et al. |
| 4,566,689 A | 1/1986 | Ogden |
| 4,566,732 A | 1/1986 | Ostergaard, Sr. |
| 4,569,518 A | 2/1986 | Fulks |
| 4,571,682 A | 2/1986 | Silverman et al. |
| 4,572,500 A | 2/1986 | Weiss |
| 4,572,504 A | 2/1986 | DiBartolo |
| 4,573,449 A | 3/1986 | Warnke |
| 4,576,352 A | 3/1986 | Ogden |
| 4,576,376 A | 3/1986 | Miller |
| 4,577,860 A | 3/1986 | Matias et al. |
| 4,577,865 A | 3/1986 | Shishido |
| 4,580,983 A | 4/1986 | Cassini et al. |
| 4,581,269 A | 4/1986 | Tilman |
| 4,582,320 A | 4/1986 | Shaw |
| 4,586,495 A | 5/1986 | Petrofsky |
| 4,589,656 A | 5/1986 | Baldwin |
| 4,591,147 A | 5/1986 | Smith et al. |
| 4,592,544 A | 6/1986 | Smith et al. |
| 4,600,196 A | 7/1986 | Jones |
| 4,601,142 A | 7/1986 | Frommelt |
| 4,602,779 A | 7/1986 | Ogden |
| 4,610,449 A | 9/1986 | Diercks, Jr. |
| 4,614,337 A | 9/1986 | Schonenberger |
| 4,616,822 A | 10/1986 | Trulaske |
| 4,618,139 A | 10/1986 | Haaheim |
| 4,618,140 A | 10/1986 | Brown |
| 4,619,454 A | 10/1986 | Walton |
| 4,621,623 A | 11/1986 | Wang |
| 4,624,457 A | 11/1986 | Silberman et al. |
| 4,625,962 A | 12/1986 | Street |
| 4,627,614 A | 12/1986 | De Angeli |
| 4,627,615 A | 12/1986 | Nurkowski |
| 4,627,616 A | 12/1986 | Kauffman |
| 4,630,817 A | 12/1986 | Buckley |
| 4,632,385 A | 12/1986 | Geraci |
| 4,632,386 A | 12/1986 | Beech |
| 4,632,390 A | 12/1986 | Richey |
| 4,634,127 A | 1/1987 | Rockwell |
| 4,635,927 A | 1/1987 | Shu |
| 4,635,928 A | 1/1987 | Ogden et al. |
| 4,637,605 A | 1/1987 | Ritchie |
| 4,638,523 A | 1/1987 | Todd |
| 4,638,969 A | 1/1987 | Brown |
| 4,641,833 A | 2/1987 | Trethewey |
| 4,642,080 A | 2/1987 | Takano et al. |
| 4,642,769 A | 2/1987 | Petrofsky |
| 4,643,418 A | 2/1987 | Bart |
| 4,645,197 A | 2/1987 | Mcfee |
| 4,645,200 A | 2/1987 | Hix |
| 4,645,201 A | 2/1987 | Evans |
| 4,645,917 A | 2/1987 | Penney et al. |
| 4,647,037 A | 3/1987 | Donohue |
| 4,647,041 A | 3/1987 | Whiteley |
| 4,650,067 A | 3/1987 | Brule |
| 4,650,184 A | 3/1987 | Brebner |
| 4,650,185 A | 3/1987 | Cartwright |
| 4,651,446 A | 3/1987 | Yukawa et al. |
| 4,651,581 A | 3/1987 | Svensson |
| 4,659,074 A | 4/1987 | Taitel et al. |
| 4,659,077 A | 4/1987 | Stropkay |
| 4,659,078 A | 4/1987 | Blome |
| 4,662,630 A | 5/1987 | Dignard et al. |
| 4,664,371 A | 5/1987 | Viander |
| 4,664,373 A | 5/1987 | Hait |
| 4,664,646 A | 5/1987 | Rorabaugh |
| 4,665,388 A | 5/1987 | Ivie et al. |
| 4,671,257 A | 6/1987 | Kaiser et al. |
| 4,673,177 A | 6/1987 | Szymski |
| 4,674,740 A | 6/1987 | Iams et al. |
| 4,674,743 A | 6/1987 | Hirano |
| 4,678,182 A | 7/1987 | Nakao et al. |
| 4,678,185 A | 7/1987 | Mahnke |
| 4,679,786 A | 7/1987 | Rodgers |
| 4,679,787 A | 7/1987 | Guilbault |
| 4,684,121 A | 8/1987 | Nestegard |
| 4,685,670 A | 8/1987 | Zinkin |
| 4,687,195 A | 8/1987 | Potts |
| 4,697,809 A | 10/1987 | Rockwell |
| 4,700,946 A | 10/1987 | Breunig |
| 4,702,475 A | 10/1987 | Elstein et al. |
| 4,705,267 A | 11/1987 | Jackson |
| 4,708,337 A | 11/1987 | Shyu |
| 4,708,338 A | 11/1987 | Potts |
| 4,708,837 A | 11/1987 | Baxter et al. |
| 4,709,917 A | 12/1987 | Yang |
| 4,709,918 A | 12/1987 | Grinblat |
| 4,709,920 A | 12/1987 | Schnell |
| 4,711,447 A | 12/1987 | Mansfield |
| 4,714,244 A | 12/1987 | Kolomayets et al. |
| 4,714,248 A | 12/1987 | Koss |
| 4,718,207 A | 1/1988 | Frommelt |
| 4,720,093 A | 1/1988 | Del Mar |
| 4,720,099 A | 1/1988 | Carlson |
| 4,720,789 A | 1/1988 | Hector et al. |
| 4,721,303 A | 1/1988 | Fitzpatrick |
| 4,725,057 A | 2/1988 | Shifferaw |
| 4,726,581 A | 2/1988 | Chang |
| 4,726,582 A | 2/1988 | Fulks |
| 4,728,099 A | 3/1988 | Pitre |
| 4,729,558 A | 3/1988 | Kuo |
| 4,729,562 A | 3/1988 | Pipasik |
| 4,730,828 A | 3/1988 | Lane |
| 4,730,829 A | 3/1988 | Carlson |
| 4,733,858 A | 3/1988 | Lan |
| 4,743,009 A | 5/1988 | Beale |
| 4,743,015 A | 5/1988 | Marshall |
| 4,744,559 A | 5/1988 | Mahnke et al. |
| 4,746,115 A | 5/1988 | Lahman |
| 4,749,184 A | 6/1988 | Tobin |
| 4,750,736 A | 6/1988 | Watterson |
| 4,750,738 A | 6/1988 | Dang |
| 4,751,755 A | 6/1988 | Carey, Jr. et al. |
| 4,756,098 A | 7/1988 | Boggia |
| 4,757,495 A | 7/1988 | Decker et al. |
| 4,757,987 A | 7/1988 | Allemand |
| 4,759,540 A | 7/1988 | Yu et al. |
| 4,763,284 A | 8/1988 | Carlin |
| 4,765,613 A | 8/1988 | Voris |

(56) References Cited

U.S. PATENT DOCUMENTS

| | | |
|---|---|---|
| 4,770,411 A | 9/1988 | Armstrong et al. |
| 4,771,148 A | 9/1988 | Bersonnet |
| 4,771,577 A | 9/1988 | Abe |
| 4,772,015 A | 9/1988 | Carlson et al. |
| 4,773,170 A | 9/1988 | Moore et al. |
| 4,774,679 A | 9/1988 | Carlin |
| 4,776,582 A | 10/1988 | Ramhorst |
| 4,779,884 A | 10/1988 | Minati |
| 4,786,049 A | 11/1988 | Lautenschlager |
| 4,786,050 A | 11/1988 | Geschwender |
| 4,789,153 A | 12/1988 | Brown |
| 4,790,522 A | 12/1988 | Drutchas |
| 4,790,528 A | 12/1988 | Nakao et al. |
| 4,792,134 A | 12/1988 | Chen |
| 4,797,968 A | 1/1989 | Wenzlick |
| 4,798,377 A | 1/1989 | White |
| 4,798,760 A | 1/1989 | Diaz-Kotti |
| 4,799,475 A | 1/1989 | Iams et al. |
| 4,799,671 A | 1/1989 | Hoggan et al. |
| 4,801,079 A | 1/1989 | Gonella |
| 4,804,178 A | 2/1989 | Friedebach |
| 4,805,901 A | 2/1989 | Kulick |
| 4,807,874 A | 2/1989 | Little |
| 4,809,804 A | 3/1989 | Houston et al. |
| 4,809,972 A | 3/1989 | Rasmussen et al. |
| 4,813,665 A | 3/1989 | Carr |
| 4,813,667 A | 3/1989 | Watterson |
| 4,813,668 A | 3/1989 | Solloway |
| 4,813,743 A | 3/1989 | Mizelle |
| 4,814,661 A | 3/1989 | Ratzlaff et al. |
| 4,817,938 A | 4/1989 | Nakao et al. |
| 4,817,940 A | 4/1989 | Shaw et al. |
| 4,818,175 A | 4/1989 | Kimura |
| 4,818,234 A | 4/1989 | Redington |
| 4,819,583 A | 4/1989 | Guerra |
| 4,819,818 A | 4/1989 | Simkus |
| 4,822,029 A | 4/1989 | Sarno |
| 4,822,034 A | 4/1989 | Shields |
| 4,826,153 A | 5/1989 | Schalip |
| 4,826,157 A | 5/1989 | Fitzpatrick |
| 4,826,158 A | 5/1989 | Fields, Jr. |
| 4,826,159 A | 5/1989 | Hersey |
| 4,828,255 A | 5/1989 | Lahman |
| 4,828,257 A | 5/1989 | Dyer et al. |
| 4,828,522 A | 5/1989 | Santos |
| 4,828,713 A | 5/1989 | McDonald et al. |
| 4,830,362 A | 5/1989 | Bull |
| 4,830,363 A | 5/1989 | Kennedy |
| 4,832,332 A | 5/1989 | Dumbser |
| 4,836,530 A | 6/1989 | Stanley, Jr. |
| 4,837,157 A | 6/1989 | Turnell et al. |
| 4,838,543 A | 6/1989 | Armstrong et al. |
| 4,838,544 A | 6/1989 | Sasakawa et al. |
| 4,840,372 A | 6/1989 | Oglesby et al. |
| 4,842,266 A | 6/1989 | Sweeney, Sr. |
| 4,842,274 A | 6/1989 | Oosthuizen |
| 4,844,449 A | 7/1989 | Truslaske |
| 4,844,450 A | 7/1989 | Rodgers, Jr. |
| 4,846,693 A | 7/1989 | Baer |
| 4,848,737 A | 7/1989 | Ehrenfield |
| 4,850,585 A | 7/1989 | Dalebout |
| 4,855,942 A | 8/1989 | Bianco |
| 4,860,763 A | 8/1989 | Schminke |
| 4,861,023 A | 8/1989 | Wedman |
| 4,861,025 A | 8/1989 | Rockwell |
| 4,863,157 A | 9/1989 | Mendel et al. |
| 4,863,161 A | 9/1989 | Telle |
| 4,865,344 A | 9/1989 | Romero, Sr. et al. |
| 4,866,704 A | 9/1989 | Bergman |
| 4,867,442 A | 9/1989 | Matthews |
| 4,867,443 A | 9/1989 | Jensen |
| 4,869,493 A | 9/1989 | Johnston |
| 4,869,494 A | 9/1989 | Lambert, Sr. |
| 4,869,497 A | 9/1989 | Stewart et al. |
| 4,875,676 A | 10/1989 | Zimmer |
| 4,877,239 A | 10/1989 | Dela Rosa |
| 4,878,662 A | 11/1989 | Chern |
| 4,878,663 A | 11/1989 | Luquette |
| 4,880,227 A | 11/1989 | Sowell |
| 4,883,272 A | 11/1989 | Lay |
| 4,886,266 A | 12/1989 | Trulaske |
| 4,889,108 A | 12/1989 | Bond et al. |
| 4,889,131 A | 12/1989 | Salem et al. |
| 4,891,764 A | 1/1990 | McIntosh |
| 4,891,785 A | 1/1990 | Donohoo |
| 4,894,933 A | 1/1990 | Tonkel et al. |
| 4,898,379 A | 2/1990 | Shiba |
| 4,898,381 A | 2/1990 | Gordon |
| 4,900,012 A | 2/1990 | Fu |
| 4,900,013 A | 2/1990 | Rodgers, Jr. |
| 4,900,017 A | 2/1990 | Bold, Jr. |
| 4,900,018 A | 2/1990 | Ish, III |
| 4,902,006 A | 2/1990 | Stallings, Jr. |
| 4,904,829 A | 2/1990 | Berthaud et al. |
| 4,905,330 A | 3/1990 | Jacobs |
| 4,907,795 A | 3/1990 | Shaw et al. |
| 4,907,797 A | 3/1990 | Gezari et al. |
| 4,907,798 A | 3/1990 | Burchatz |
| 4,907,973 A | 3/1990 | Hon |
| 4,909,504 A | 3/1990 | Yang |
| 4,911,427 A | 3/1990 | Matsumoto et al. |
| 4,911,438 A | 3/1990 | Van Straaten |
| 4,912,638 A | 3/1990 | Pratt, Jr. |
| 4,913,396 A | 4/1990 | Dalebout et al. |
| 4,913,423 A | 4/1990 | Farran |
| 4,915,377 A | 4/1990 | Malnke et al. |
| 4,915,379 A | 4/1990 | Sapp |
| 4,917,376 A | 4/1990 | Lo |
| 4,919,418 A | 4/1990 | Miller |
| 4,919,419 A | 4/1990 | Houston |
| 4,921,242 A | 5/1990 | Watterson |
| 4,921,247 A | 5/1990 | Sterling |
| 4,923,193 A | 5/1990 | Pitzen et al. |
| 4,925,183 A | 5/1990 | Kim |
| 4,925,189 A | 5/1990 | Braeunig |
| 4,925,724 A | 5/1990 | Ogden |
| 4,927,136 A | 5/1990 | Leask |
| 4,928,546 A | 5/1990 | Walters |
| 4,928,957 A | 5/1990 | Lanier et al. |
| 4,930,768 A | 6/1990 | Lapcevic |
| 4,930,769 A | 6/1990 | Nenoff |
| 4,930,770 A | 6/1990 | Baker |
| 4,934,690 A | 6/1990 | Bull |
| 4,934,692 A | 6/1990 | Owens |
| 4,934,694 A | 6/1990 | Mcintosh |
| 4,938,469 A | 7/1990 | Crandell |
| 4,938,473 A | 7/1990 | Lee |
| 4,938,474 A | 7/1990 | Sweeney et al. |
| 4,940,233 A | 7/1990 | Bull |
| 4,941,652 A | 7/1990 | Nagano et al. |
| 4,941,673 A | 7/1990 | Bennett |
| 4,948,121 A | 8/1990 | Haaheim et al. |
| 4,949,954 A | 8/1990 | Hix |
| 4,949,958 A | 8/1990 | Richey |
| 4,949,959 A | 8/1990 | Stevens |
| 4,949,993 A | 8/1990 | Stark et al. |
| 4,952,265 A | 8/1990 | Yamanaka et al. |
| 4,953,415 A | 9/1990 | Lehtonen |
| 4,953,858 A | 9/1990 | Zelli |
| 4,955,466 A | 9/1990 | Almes et al. |
| 4,958,832 A | 9/1990 | Kim |
| 4,959,713 A | 9/1990 | Morotomi et al. |
| 4,960,276 A | 10/1990 | Feuer et al. |
| 4,964,632 A | 10/1990 | Rockwell |
| 4,968,028 A | 11/1990 | Wehrell |
| 4,971,316 A | 11/1990 | Dalebout et al. |
| 4,974,831 A | 12/1990 | Dunham |
| 4,974,832 A | 12/1990 | Dalebout |
| 4,976,424 A | 12/1990 | Sargeant et al. |
| 4,976,428 A | 12/1990 | Ghazi |
| 4,976,435 A | 12/1990 | Shatford |
| 4,983,847 A | 1/1991 | Bryan |
| 4,984,810 A | 1/1991 | Stearns et al. |
| 4,986,261 A | 1/1991 | Iams et al. |

(56) References Cited

U.S. PATENT DOCUMENTS

| | | |
|---|---|---|
| 4,986,534 A | 1/1991 | Meier et al. |
| 4,986,689 A | 1/1991 | Drutchas |
| 4,989,860 A | 2/1991 | Iams et al. |
| 4,992,190 A | 2/1991 | Shtarkman |
| 4,998,725 A | 3/1991 | Watterson et al. |
| 5,000,440 A | 3/1991 | Lynch |
| 5,000,442 A | 3/1991 | Dalebout et al. |
| 5,001,632 A | 3/1991 | Hall Tipping |
| 5,002,271 A | 3/1991 | Gonzales |
| 5,004,224 A | 4/1991 | Wang |
| 5,007,630 A | 4/1991 | Real et al. |
| 5,007,631 A | 4/1991 | Wang |
| 5,013,031 A | 5/1991 | Bull |
| 5,015,926 A | 5/1991 | Casler |
| 5,016,870 A | 5/1991 | Bulloch et al. |
| 5,020,793 A | 6/1991 | Loane |
| 5,020,794 A | 6/1991 | Englehardt et al. |
| 5,020,795 A | 6/1991 | Airy et al. |
| 5,024,441 A | 6/1991 | Rousseau |
| 5,026,049 A | 6/1991 | Goodman |
| 5,029,801 A | 7/1991 | Dalebout et al. |
| 5,031,901 A | 7/1991 | Saarinen |
| 5,034,576 A | 7/1991 | Dalebout et al. |
| 5,035,418 A | 7/1991 | Harabayashi |
| RE33,662 E | 8/1991 | Blair et al. |
| 5,037,084 A | 8/1991 | Flor |
| 5,037,089 A | 8/1991 | Spagnuolo |
| 5,039,088 A | 8/1991 | Shifferaw |
| 5,039,089 A | 8/1991 | Lapcevic |
| 5,039,091 A | 8/1991 | Johnson |
| 5,042,799 A | 8/1991 | Stanley |
| 5,046,382 A | 9/1991 | Steinberg |
| 5,046,722 A | 9/1991 | Antoon |
| 5,048,823 A | 9/1991 | Bean |
| 5,051,638 A | 9/1991 | Pyles |
| 5,052,375 A | 10/1991 | Stark |
| 5,052,684 A | 10/1991 | Kosuge et al. |
| 5,054,770 A | 10/1991 | Bull |
| 5,054,774 A | 10/1991 | Belsito |
| 5,058,881 A | 10/1991 | Measom |
| 5,058,882 A | 10/1991 | Dalebout et al. |
| 5,058,888 A | 10/1991 | Walker et al. |
| 5,062,626 A | 11/1991 | Dalebout et al. |
| 5,062,629 A | 11/1991 | Vaughan |
| 5,062,632 A | 11/1991 | Dalebout et al. |
| 5,066,000 A | 11/1991 | Dolan |
| 5,067,710 A | 11/1991 | Watterson et al. |
| 5,071,115 A | 12/1991 | Welch |
| 5,072,928 A | 12/1991 | Stearns et al. |
| 5,072,929 A | 12/1991 | Peterson et al. |
| 5,074,550 A | 12/1991 | Sloan |
| 5,077,916 A | 1/1992 | Beneteau |
| 5,078,152 A | 1/1992 | Bond et al. |
| 5,080,353 A | 1/1992 | Tench |
| 5,081,991 A | 1/1992 | Chance |
| 5,085,426 A | 2/1992 | Wanzer et al. |
| 5,085,427 A | 2/1992 | Finn |
| 5,086,385 A | 2/1992 | Launey et al. |
| 5,087,047 A | 2/1992 | McConnell |
| 5,088,729 A | 2/1992 | Dalebout |
| 5,089,960 A | 2/1992 | Sweeney, Jr. |
| 5,094,249 A | 3/1992 | Marras et al. |
| 5,094,447 A | 3/1992 | Wang |
| 5,096,225 A | 3/1992 | Osawa |
| 5,102,122 A | 4/1992 | Piane, Jr. |
| 5,102,380 A | 4/1992 | Jacobson et al. |
| 5,104,119 A | 4/1992 | Lynch |
| 5,104,120 A | 4/1992 | Watterson et al. |
| 5,108,093 A | 4/1992 | Watterson |
| 5,109,778 A | 5/1992 | Berkowitz et al. |
| 5,110,117 A | 5/1992 | Fisher et al. |
| 5,112,045 A | 5/1992 | Mason et al. |
| 5,113,427 A | 5/1992 | Ryoichi et al. |
| 5,114,388 A | 5/1992 | Trulaske |
| 5,114,391 A | 5/1992 | Pitzen et al. |
| 5,117,674 A | 6/1992 | Howard |
| 5,118,112 A | 6/1992 | Bregman et al. |
| 5,123,629 A | 6/1992 | Takeuchi |
| 5,123,885 A | 6/1992 | Shields |
| 5,123,886 A | 6/1992 | Cook |
| 5,129,872 A | 7/1992 | Dalton et al. |
| 5,131,895 A | 7/1992 | Rogers, Jr. |
| 5,135,458 A | 8/1992 | Huang |
| 5,137,501 A | 8/1992 | Mertesdorf |
| 5,138,730 A | 8/1992 | Masuda |
| 5,141,480 A | 8/1992 | Lennox et al. |
| 5,142,358 A | 8/1992 | Jason |
| 5,145,475 A | 9/1992 | Cares |
| 5,145,481 A | 9/1992 | Friedebach |
| 5,147,266 A | 9/1992 | Ricard |
| 5,149,084 A | 9/1992 | Dalebout et al. |
| 5,149,312 A | 9/1992 | Croft et al. |
| 5,152,210 A | 10/1992 | Chen |
| 5,158,093 A | 10/1992 | Shvartz |
| 5,158,520 A | 10/1992 | Lemke et al. |
| 5,162,029 A | 11/1992 | Schine |
| 5,163,885 A | 11/1992 | Wanzer et al. |
| 5,167,597 A | 12/1992 | David |
| 5,167,850 A | 12/1992 | Shtarkman |
| 5,171,196 A | 12/1992 | Lynch |
| 5,176,602 A | 1/1993 | Roberts |
| 5,178,593 A | 1/1993 | Roberts |
| 5,178,599 A | 1/1993 | Scott |
| 5,180,347 A | 1/1993 | Chen |
| 5,180,351 A | 1/1993 | Ehrenfried |
| 5,180,647 A | 1/1993 | Rowland et al. |
| 5,181,894 A | 1/1993 | Shieng |
| 5,184,295 A | 2/1993 | Mann |
| 5,184,988 A | 2/1993 | Dunham |
| 5,186,471 A | 2/1993 | Vancraeynest |
| 5,186,697 A | 2/1993 | Rennex |
| 5,192,255 A | 3/1993 | Dalebout et al. |
| 5,192,257 A | 3/1993 | Panasewicz |
| 5,192,258 A | 3/1993 | Keller |
| 5,195,781 A | 3/1993 | Osawa |
| 5,195,935 A | 3/1993 | Fencel |
| 5,195,937 A | 3/1993 | Engel et al. |
| 5,199,931 A | 4/1993 | Easley et al. |
| 5,201,694 A | 4/1993 | Zappel |
| 5,201,772 A | 4/1993 | Maxwell |
| 5,202,424 A | 4/1993 | Vlassara et al. |
| 5,203,229 A | 4/1993 | Chen |
| 5,203,800 A | 4/1993 | Meredith |
| 5,203,826 A | 4/1993 | Dalebout |
| 5,204,670 A | 4/1993 | Stinton |
| 5,205,798 A | 4/1993 | Lekhtman |
| 5,205,800 A | 4/1993 | Grant |
| 5,206,671 A | 4/1993 | Eydelman et al. |
| 5,207,489 A | 5/1993 | Miller |
| 5,207,622 A | 5/1993 | Wilkinson et al. |
| 5,207,625 A | 5/1993 | White |
| 5,207,628 A | 5/1993 | Graham |
| 5,211,617 A | 5/1993 | Millen |
| 5,213,555 A | 5/1993 | Hood |
| 5,215,510 A | 6/1993 | Baran |
| 5,217,422 A | 6/1993 | Domzalski |
| 5,226,866 A | 7/1993 | Engel et al. |
| 5,230,672 A | 7/1993 | Brown et al. |
| 5,230,673 A | 7/1993 | Maeyama et al. |
| 5,232,422 A | 8/1993 | Bishop, Jr. |
| 5,233,520 A | 8/1993 | Kretsch et al. |
| 5,234,392 A | 8/1993 | Clark |
| 5,234,395 A | 8/1993 | Miller et al. |
| 5,240,417 A | 8/1993 | Smithson et al. |
| 5,242,339 A | 9/1993 | Thornton |
| 5,242,340 A | 9/1993 | Jerome |
| 5,242,343 A | 9/1993 | Miller |
| 5,242,347 A | 9/1993 | Keeton |
| 5,243,998 A | 9/1993 | Silverman et al. |
| 5,246,411 A | 9/1993 | Rackman |
| 5,247,853 A | 9/1993 | Dalebout |
| 5,250,012 A | 10/1993 | Whitcomb, Jr. |
| 5,250,013 A | 10/1993 | Brangi |
| 5,254,066 A | 10/1993 | Brown et al. |

(56) References Cited

U.S. PATENT DOCUMENTS

| | | |
|---|---|---|
| 5,254,067 A | 10/1993 | Habing et al. |
| 5,256,115 A | 10/1993 | Scholder |
| 5,256,117 A | 10/1993 | Potts et al. |
| 5,256,118 A | 10/1993 | Chen |
| 5,256,126 A | 10/1993 | Grotstein |
| 5,257,084 A | 10/1993 | Marsh |
| 5,257,701 A | 11/1993 | Edelson |
| 5,257,964 A | 11/1993 | Petters |
| 5,260,870 A | 11/1993 | Tsuchiya et al. |
| 5,261,864 A | 11/1993 | Fitzpatrick |
| 5,267,925 A | 12/1993 | Boyd |
| 5,269,081 A | 12/1993 | Gray |
| 5,269,519 A | 12/1993 | Malone |
| 5,269,736 A | 12/1993 | Roberts |
| 5,271,416 A | 12/1993 | Lepley |
| 5,273,285 A | 12/1993 | Long |
| 5,277,678 A | 1/1994 | Friedebach et al. |
| 5,279,528 A | 1/1994 | Dalebout et al. |
| 5,279,529 A | 1/1994 | Eschenbach |
| 5,279,531 A | 1/1994 | Jen Huey |
| 5,282,776 A | 2/1994 | Dalebout |
| 5,284,461 A | 2/1994 | Wilkinson et al. |
| 5,290,205 A | 3/1994 | Densmore et al. |
| 5,290,211 A | 3/1994 | Stearns |
| 5,292,293 A | 3/1994 | Schumacher |
| 5,295,928 A | 3/1994 | Rennex |
| 5,295,935 A | 3/1994 | Wang |
| 5,299,810 A | 4/1994 | Pierce et al. |
| 5,299,992 A | 4/1994 | Wilkinson |
| 5,299,993 A | 4/1994 | Habing |
| 5,301,154 A | 4/1994 | Suga |
| 5,302,162 A | 4/1994 | Pasero |
| 5,306,220 A | 4/1994 | Kearney |
| 5,306,221 A | 4/1994 | Itaru |
| 5,308,075 A | 5/1994 | Theriault |
| 5,308,296 A | 5/1994 | Eckstein |
| 5,308,300 A | 5/1994 | Chino et al. |
| 5,308,304 A | 5/1994 | Habing |
| 5,309,355 A | 5/1994 | Lockwood |
| 5,310,392 A | 5/1994 | Lo |
| 5,313,852 A | 5/1994 | Arena |
| 5,313,942 A | 5/1994 | Platzker |
| 5,314,389 A | 5/1994 | Dotan |
| 5,314,390 A | 5/1994 | Westing et al. |
| 5,314,391 A | 5/1994 | Potash et al. |
| 5,314,392 A | 5/1994 | Hawkins et al. |
| 5,314,394 A | 5/1994 | Ronan |
| 5,316,534 A | 5/1994 | Dalebout et al. |
| 5,318,487 A | 6/1994 | Golen et al. |
| 5,318,491 A | 6/1994 | Houston |
| 5,320,343 A | 6/1994 | McKinney |
| 5,320,588 A | 6/1994 | Wanzer et al. |
| 5,320,591 A | 6/1994 | Harmon et al. |
| 5,323,650 A | 6/1994 | Fullen et al. |
| 5,323,784 A | 6/1994 | Shu |
| 5,324,242 A | 6/1994 | Lo |
| 5,328,420 A | 7/1994 | Allen |
| 5,328,422 A | 7/1994 | Nichols |
| 5,328,429 A | 7/1994 | Potash et al. |
| 5,330,401 A | 7/1994 | Walstead |
| 5,330,402 A | 7/1994 | Johnson |
| 5,334,120 A | 8/1994 | Rasmussen |
| 5,335,188 A | 8/1994 | Brisson |
| 5,336,144 A | 8/1994 | Rodden |
| 5,336,145 A | 8/1994 | Keiser |
| 5,336,146 A | 8/1994 | Piaget et al. |
| 5,342,264 A | 8/1994 | Gordon |
| 5,342,271 A | 8/1994 | Long |
| RE34,728 E | 9/1994 | Hall-Tipping |
| 5,344,372 A | 9/1994 | Hung |
| 5,348,524 A | 9/1994 | Grant |
| 5,350,344 A | 9/1994 | Kissel |
| 5,352,166 A | 10/1994 | Chang |
| 5,352,167 A | 10/1994 | Ulicny |
| 5,352,169 A | 10/1994 | Eschenbach |
| 5,353,452 A | 10/1994 | Rulis |
| 5,354,248 A | 10/1994 | Rawls et al. |
| 5,354,251 A | 10/1994 | Sleamaker |
| 5,356,356 A | 10/1994 | Hildebrandt et al. |
| 5,357,696 A | 10/1994 | Gray |
| 5,358,461 A | 10/1994 | Bailey, Jr. |
| 5,359,986 A | 11/1994 | Magrath, III et al. |
| 5,361,091 A | 11/1994 | Hoarty et al. |
| 5,361,778 A | 11/1994 | Seitz |
| 5,362,069 A | 11/1994 | Hall-Tipping |
| 5,362,295 A | 11/1994 | Nurge |
| 5,362,298 A | 11/1994 | Brown et al. |
| 5,364,271 A | 11/1994 | Aknin et al. |
| 5,364,327 A | 11/1994 | Graham |
| 5,368,532 A | 11/1994 | Farnet |
| 5,372,556 A | 12/1994 | Ropp |
| 5,372,559 A | 12/1994 | Dalebout et al. |
| 5,372,560 A | 12/1994 | Chang |
| 5,372,564 A | 12/1994 | Spirito |
| 5,374,227 A | 12/1994 | Webb |
| 5,375,068 A | 12/1994 | Palmer et al. |
| 5,377,171 A | 12/1994 | Schlup |
| 5,377,258 A | 12/1994 | Bro |
| 5,378,212 A | 1/1995 | Pin-Kuo |
| 5,380,258 A | 1/1995 | Hawley, Jr. |
| 5,382,207 A | 1/1995 | Skowronski et al. |
| 5,382,208 A | 1/1995 | Hu |
| 5,382,209 A | 1/1995 | Pasier |
| 5,383,827 A | 1/1995 | Stern |
| 5,383,828 A | 1/1995 | Sands et al. |
| 5,385,346 A | 1/1995 | Carroll et al. |
| 5,385,519 A | 1/1995 | Hsu |
| 5,385,520 A | 1/1995 | Lepine et al. |
| 5,387,164 A | 2/1995 | Brown, Jr. |
| 5,387,169 A | 2/1995 | Wang |
| 5,387,170 A | 2/1995 | Rawls et al. |
| 5,387,171 A | 2/1995 | Casey et al. |
| 5,391,080 A | 2/1995 | Bernacki |
| 5,394,922 A | 3/1995 | Colson et al. |
| 5,396,340 A | 3/1995 | Ishii et al. |
| 5,396,876 A | 3/1995 | Liscio et al. |
| 5,398,948 A | 3/1995 | Mathis |
| 5,401,226 A | 3/1995 | Stearns |
| 5,403,251 A | 4/1995 | Belsito et al. |
| 5,403,252 A | 4/1995 | Leon et al. |
| 5,403,253 A | 4/1995 | Gaylord |
| 5,403,254 A | 4/1995 | Lundin et al. |
| 5,403,255 A | 4/1995 | Johnston |
| 5,406,661 A | 4/1995 | Pekar |
| 5,407,402 A | 4/1995 | Brown et al. |
| 5,407,403 A | 4/1995 | Coleman |
| 5,407,408 A | 4/1995 | Wilkinson |
| 5,409,435 A | 4/1995 | Daniels |
| 5,410,471 A | 4/1995 | Alyfuku et al. |
| 5,410,472 A | 4/1995 | Anderson |
| RE34,959 E | 5/1995 | Potts |
| 5,410,971 A | 5/1995 | Golden et al. |
| 5,417,222 A | 5/1995 | Dempsey et al. |
| 5,417,643 A | 5/1995 | Taylor |
| 5,419,562 A | 5/1995 | Cromarty |
| 5,419,570 A | 5/1995 | Bollotte |
| 5,419,571 A | 5/1995 | Vaughan |
| 5,419,751 A | 5/1995 | Byrd et al. |
| 5,421,801 A | 6/1995 | Davies, III et al. |
| 5,423,729 A | 6/1995 | Eschenbach |
| 5,423,730 A | 6/1995 | Hirsch |
| 5,429,563 A | 7/1995 | Engel et al. |
| 5,429,569 A | 7/1995 | Gunnari |
| 5,431,612 A | 7/1995 | Holden |
| 5,433,679 A | 7/1995 | Szymczak et al. |
| 5,435,315 A | 7/1995 | McPhee et al. |
| 5,435,798 A | 7/1995 | Habing et al. |
| 5,435,799 A | 7/1995 | Lundin |
| 5,437,289 A | 8/1995 | Liverance |
| 5,441,467 A | 8/1995 | Stevens |
| 5,441,468 A | 8/1995 | Deckers et al. |
| 5,445,583 A | 8/1995 | Habing |
| 5,449,334 A | 9/1995 | Kingsbury |
| 5,451,922 A | 9/1995 | Hamilton |

(56) References Cited

U.S. PATENT DOCUMENTS

| | | |
|---|---|---|
| 5,452,269 A | 9/1995 | Cherdak |
| 5,454,772 A | 10/1995 | Rodden |
| 5,454,773 A | 10/1995 | Blanchard et al. |
| 5,456,262 A | 10/1995 | Birnbaum |
| 5,456,648 A | 10/1995 | Edinburg |
| 5,460,586 A | 10/1995 | Wilkinson |
| 5,462,051 A | 10/1995 | Oka et al. |
| 5,462,503 A | 10/1995 | Benjamin et al. |
| 5,462,504 A | 10/1995 | Trulaske et al. |
| 5,466,200 A | 11/1995 | Ulrich et al. |
| 5,466,203 A | 11/1995 | Chen |
| 5,469,740 A | 11/1995 | French et al. |
| 5,470,298 A | 11/1995 | Curtis |
| 5,471,405 A | 11/1995 | Marsh |
| 5,472,205 A | 12/1995 | Bouton |
| 5,474,077 A | 12/1995 | Suga |
| 5,474,087 A | 12/1995 | Nashner |
| 5,474,090 A | 12/1995 | Begun et al. |
| 5,474,510 A | 12/1995 | Chen |
| 5,476,428 A | 12/1995 | Potash et al. |
| 5,476,430 A | 12/1995 | Lee et al. |
| 5,478,295 A | 12/1995 | Fracchia |
| 5,482,472 A | 1/1996 | Garoni et al. |
| 5,484,358 A | 1/1996 | Wang et al. |
| 5,484,362 A | 1/1996 | Skowronski et al. |
| 5,484,389 A | 1/1996 | Stark |
| 5,486,001 A | 1/1996 | Baker |
| 5,487,707 A | 1/1996 | Sharf et al. |
| 5,489,249 A | 2/1996 | Brewer et al. |
| 5,489,250 A | 2/1996 | Densmore et al. |
| 5,490,818 A | 2/1996 | Haber et al. |
| 5,492,514 A | 2/1996 | Daum |
| 5,492,520 A | 2/1996 | Brown |
| 5,493,127 A | 2/1996 | Lloyd et al. |
| 5,496,235 A | 3/1996 | Stevens |
| 5,496,236 A | 3/1996 | Buonauito |
| 5,496,238 A | 3/1996 | Taylor |
| 5,496,239 A | 3/1996 | Kallman |
| 5,499,956 A | 3/1996 | Habing et al. |
| 5,505,011 A | 4/1996 | Bleimhofer |
| 5,507,271 A | 4/1996 | Actor |
| 5,509,870 A | 4/1996 | Lloyd |
| 5,510,828 A | 4/1996 | Lutterbach |
| 5,512,025 A | 4/1996 | Dalebout et al. |
| 5,512,029 A | 4/1996 | Barnard |
| 5,514,053 A | 5/1996 | Hawkins et al. |
| 5,516,334 A | 5/1996 | Easton |
| 5,518,471 A | 5/1996 | Hettinger et al. |
| 5,518,473 A | 5/1996 | Miller |
| 5,519,189 A | 5/1996 | Gibisch |
| 5,520,599 A | 5/1996 | Chen |
| 5,522,783 A | 6/1996 | Gordon |
| 5,524,110 A | 6/1996 | Danneels et al. |
| 5,524,637 A | 6/1996 | Erickson |
| 5,527,239 A | 6/1996 | Abbondanza |
| 5,527,245 A | 6/1996 | Dalebout et al. |
| 5,529,554 A | 6/1996 | Eschenbach |
| 5,531,658 A | 7/1996 | L. S. C. |
| 5,533,899 A | 7/1996 | Young |
| 5,533,948 A | 7/1996 | Wilkinson |
| 5,533,951 A | 7/1996 | Chang |
| 5,535,664 A | 7/1996 | Rokowski |
| 5,538,486 A | 7/1996 | France et al. |
| 5,538,489 A | 7/1996 | Magid |
| 5,542,420 A | 8/1996 | Goldman |
| 5,542,672 A | 8/1996 | Meredith |
| 5,542,892 A | 8/1996 | Buhler |
| 5,545,112 A | 8/1996 | Densmore et al. |
| 5,547,439 A | 8/1996 | Rawls et al. |
| 5,549,052 A | 8/1996 | Hoffman |
| 5,549,536 A | 8/1996 | Clark |
| 5,551,934 A | 9/1996 | Binette |
| 5,551,937 A | 9/1996 | Kwo |
| 5,554,033 A | 9/1996 | Bizzi et al. |
| 5,554,083 A | 9/1996 | Chen |
| 5,556,362 A | 9/1996 | Whipps |
| 5,562,572 A | 10/1996 | Carmein |
| 5,562,574 A | 10/1996 | Miller |
| 5,563,487 A | 10/1996 | Davis |
| 5,568,993 A | 10/1996 | Potzick |
| 5,569,120 A | 10/1996 | Anjanappa et al. |
| 5,569,128 A | 10/1996 | Dalebout |
| 5,569,138 A | 10/1996 | Wang et al. |
| 5,572,643 A | 11/1996 | Judson |
| 5,573,485 A | 11/1996 | Geschwender |
| 5,575,740 A | 11/1996 | Piaget |
| 5,576,951 A | 11/1996 | Lockwood |
| 5,577,186 A | 11/1996 | Mann, II et al. |
| 5,577,981 A | 11/1996 | Jarvik |
| 5,577,985 A | 11/1996 | Miller |
| 5,577,987 A | 11/1996 | Brown |
| 5,580,249 A | 12/1996 | Jacobsen et al. |
| 5,582,563 A | 12/1996 | Fan |
| 5,584,700 A | 12/1996 | Feldman et al. |
| 5,584,779 A | 12/1996 | Knecht |
| 5,584,784 A | 12/1996 | Wu |
| 5,585,583 A | 12/1996 | Owen |
| 5,586,736 A | 12/1996 | Mollet |
| 5,586,962 A | 12/1996 | Hallmark |
| 5,588,938 A | 12/1996 | Schneider et al. |
| 5,590,128 A | 12/1996 | Maloney et al. |
| 5,590,181 A | 12/1996 | Hogan et al. |
| 5,590,893 A | 1/1997 | Robinson et al. |
| 5,591,104 A | 1/1997 | Andrus et al. |
| 5,591,106 A | 1/1997 | Dalebout et al. |
| 5,591,107 A | 1/1997 | Rodgers, Jr. |
| 5,593,372 A | 1/1997 | Rodgers, Jr. |
| 5,593,380 A | 1/1997 | Bittikofer |
| 5,595,556 A | 1/1997 | Dalebout et al. |
| 5,598,849 A | 2/1997 | Browne |
| 5,599,261 A | 2/1997 | Easley et al. |
| 5,600,310 A | 2/1997 | Whipple, III et al. |
| 5,603,675 A | 2/1997 | Wu |
| 5,603,678 A | 2/1997 | Wilson |
| 5,605,336 A | 2/1997 | Gaoiran |
| 5,607,375 A | 3/1997 | Dalebout |
| 5,613,216 A | 3/1997 | Galler |
| 5,613,856 A | 3/1997 | Hoover |
| 5,616,103 A | 4/1997 | Lee |
| 5,618,245 A | 4/1997 | Trulaske et al. |
| 5,618,250 A | 4/1997 | Butz |
| 5,619,412 A | 4/1997 | Hapka |
| 5,619,991 A | 4/1997 | Sloane |
| 5,622,527 A | 4/1997 | Watterson et al. |
| 5,625,577 A | 4/1997 | Kunii et al. |
| 5,626,539 A | 5/1997 | Piaget |
| 5,630,566 A | 5/1997 | Case |
| 5,632,209 A | 5/1997 | Sakakibara |
| 5,634,870 A | 6/1997 | Wilkinson |
| 5,638,343 A | 6/1997 | Ticknor |
| 5,643,142 A | 7/1997 | Salerno et al. |
| 5,643,144 A | 7/1997 | Trulaske |
| 5,643,146 A | 7/1997 | Stark et al. |
| 5,643,147 A | 7/1997 | Huang |
| 5,643,152 A | 7/1997 | Simonson |
| 5,643,153 A | 7/1997 | Nylen et al. |
| 5,643,157 A | 7/1997 | Seliber |
| 5,645,509 A | 7/1997 | Brewer et al. |
| 5,645,513 A | 7/1997 | Haydocy et al. |
| 5,645,914 A | 7/1997 | Horowitz |
| 5,649,882 A | 7/1997 | Parikh et al. |
| 5,650,709 A | 7/1997 | Rotunda et al. |
| 5,652,304 A | 7/1997 | Calderon et al. |
| 5,652,824 A | 7/1997 | Hirayama et al. |
| 5,653,662 A | 8/1997 | Rodgers, Jr. |
| 5,655,945 A | 8/1997 | Jani |
| 5,655,997 A | 8/1997 | Greenberg et al. |
| 5,656,003 A | 8/1997 | Robinson et al. |
| 5,658,227 A | 8/1997 | Stearns |
| 5,659,691 A | 8/1997 | Durward et al. |
| 5,662,557 A | 9/1997 | Watterson et al. |
| 5,665,031 A | 9/1997 | Hsieh |
| 5,665,033 A | 9/1997 | Palmer |
| 5,667,459 A | 9/1997 | Su |

(56) References Cited

U.S. PATENT DOCUMENTS

| | | |
|---|---|---|
| 5,669,833 A | 9/1997 | Stone |
| 5,669,857 A | 9/1997 | Watterson et al. |
| 5,669,865 A | 9/1997 | Gordon |
| 5,672,140 A | 9/1997 | Watterson et al. |
| 5,674,156 A | 10/1997 | Watterson et al. |
| 5,674,453 A | 10/1997 | Watterson et al. |
| 5,676,138 A | 10/1997 | Zawilinski |
| 5,676,624 A | 10/1997 | Watterson et al. |
| 5,679,047 A | 10/1997 | Engel |
| 5,679,101 A | 10/1997 | Magid |
| 5,683,332 A | 11/1997 | Watterson et al. |
| 5,685,804 A | 11/1997 | Whan-Tong et al. |
| 5,688,209 A | 11/1997 | Trulaske et al. |
| 5,688,216 A | 11/1997 | Mauriello |
| 5,690,582 A | 11/1997 | Ulrich et al. |
| 5,690,587 A | 11/1997 | Gruenangerl |
| 5,690,589 A | 11/1997 | Rodgers, Jr. |
| 5,690,852 A | 11/1997 | Saito et al. |
| 5,692,994 A | 12/1997 | Eschenbach |
| 5,693,004 A | 12/1997 | Carlson et al. |
| 5,695,400 A | 12/1997 | Fennell, Jr. et al. |
| 5,695,436 A | 12/1997 | Huang |
| 5,697,834 A | 12/1997 | Heumann et al. |
| 5,702,323 A | 12/1997 | Poulton |
| 5,702,325 A | 12/1997 | Watterson et al. |
| 5,704,875 A | 1/1998 | Tanabe |
| 5,704,879 A | 1/1998 | Watterson et al. |
| 5,707,319 A | 1/1998 | Riley |
| 5,708,355 A | 1/1998 | Schrey |
| 5,709,632 A | 1/1998 | Socwell |
| 5,709,633 A | 1/1998 | Sokol |
| 5,710,884 A | 1/1998 | Dedrick |
| 5,711,745 A | 1/1998 | Yang |
| 5,711,746 A | 1/1998 | Carlson |
| 5,711,749 A | 1/1998 | Miller |
| 5,713,549 A | 2/1998 | Shieh |
| 5,713,794 A | 2/1998 | Shimojima et al. |
| 5,713,821 A | 2/1998 | Nissen |
| 5,716,308 A | 2/1998 | Lee |
| 5,718,657 A | 2/1998 | Dalebout et al. |
| 5,718,660 A | 2/1998 | Chen |
| 5,719,825 A | 2/1998 | Dotter |
| 5,720,200 A | 2/1998 | Anderson et al. |
| 5,720,474 A | 2/1998 | Sugiyama |
| 5,720,771 A | 2/1998 | Snell |
| 5,721,539 A | 2/1998 | Goetzl |
| 5,722,418 A | 3/1998 | Bro |
| 5,722,420 A | 3/1998 | Lee |
| 5,722,917 A | 3/1998 | Olschansky et al. |
| 5,722,920 A | 3/1998 | Bauer |
| 5,722,922 A | 3/1998 | Watterson et al. |
| 5,724,025 A | 3/1998 | Tavori |
| 5,725,459 A | 3/1998 | Rexach |
| 5,730,236 A | 3/1998 | Miller et al. |
| 5,733,228 A | 3/1998 | Stevens |
| 5,733,229 A | 3/1998 | Dalebout et al. |
| 5,734,625 A | 3/1998 | Kondo |
| 5,735,586 A | 4/1998 | Cheng |
| 5,735,773 A | 4/1998 | Vittone |
| 5,735,776 A | 4/1998 | Swezey |
| 5,738,612 A | 4/1998 | Tsuda |
| 5,739,457 A | 4/1998 | Devecka |
| 5,741,205 A | 4/1998 | Doll et al. |
| 5,743,193 A | 4/1998 | Kakuta et al. |
| 5,743,832 A | 4/1998 | Sands et al. |
| 5,743,833 A | 4/1998 | Watterson et al. |
| 5,743,835 A | 4/1998 | Trotter |
| 5,746,682 A | 5/1998 | Hung |
| 5,749,372 A | 5/1998 | Allen |
| 5,749,787 A | 5/1998 | Jank |
| 5,749,807 A | 5/1998 | Webb |
| 5,749,809 A | 5/1998 | Lin |
| 5,749,813 A | 5/1998 | Domzalski |
| 5,752,879 A | 5/1998 | Berdut |
| 5,752,883 A | 5/1998 | Butcher et al. |
| 5,752,897 A | 5/1998 | Skowronski et al. |
| 5,754,765 A | 5/1998 | Danneels et al. |
| 5,755,642 A | 5/1998 | Miller |
| 5,755,645 A | 5/1998 | Miller et al. |
| 5,755,651 A | 5/1998 | Homyonfer |
| 5,759,136 A | 6/1998 | Chen |
| 5,759,199 A | 6/1998 | Snell et al. |
| 5,760,353 A | 6/1998 | Rapp |
| 5,761,831 A | 6/1998 | Cho |
| 5,762,503 A | 6/1998 | Hoo et al. |
| 5,762,587 A | 6/1998 | Dalebout et al. |
| 5,762,588 A | 6/1998 | Chen |
| 5,769,755 A | 6/1998 | Henry et al. |
| 5,769,759 A | 6/1998 | Alter |
| 5,771,152 A | 6/1998 | Crompton et al. |
| 5,771,354 A | 6/1998 | Crawford |
| 5,772,508 A | 6/1998 | Sugita et al. |
| 5,772,522 A | 6/1998 | Nesbit |
| 5,772,558 A | 6/1998 | Rodgers, Jr. |
| 5,772,560 A | 6/1998 | Watterson et al. |
| 5,776,582 A | 7/1998 | Needham |
| 5,777,678 A | 7/1998 | Ogata et al. |
| 5,779,596 A | 7/1998 | Weber |
| 5,779,599 A | 7/1998 | Chen |
| 5,779,607 A | 7/1998 | Harris |
| 5,782,639 A | 7/1998 | Beal |
| 5,782,723 A | 7/1998 | Kuo |
| 5,785,630 A | 7/1998 | Bobick et al. |
| 5,785,631 A | 7/1998 | Heidecke |
| 5,785,632 A | 7/1998 | Greenberg et al. |
| 5,788,609 A | 8/1998 | Miller |
| 5,788,610 A | 8/1998 | Eschenbach |
| 5,788,611 A | 8/1998 | Kuo |
| 5,790,785 A | 8/1998 | Klug et al. |
| 5,792,027 A | 8/1998 | Gvoich |
| 5,792,031 A | 8/1998 | Alton |
| 5,794,210 A | 8/1998 | Goldhaber et al. |
| 5,795,270 A | 8/1998 | Woods et al. |
| 5,797,578 A | 8/1998 | Graffeo |
| 5,797,805 A | 8/1998 | Lubell et al. |
| 5,799,281 A | 8/1998 | Login et al. |
| 5,803,870 A | 9/1998 | Buhler |
| 5,803,874 A | 9/1998 | Wilkinson |
| 5,803,877 A | 9/1998 | Franey |
| 5,803,882 A | 9/1998 | Habing et al. |
| 5,807,210 A | 9/1998 | Devlin |
| 5,810,696 A | 9/1998 | Webb |
| 5,810,697 A | 9/1998 | Joiner |
| 5,810,698 A | 9/1998 | Hullett et al. |
| 5,810,747 A | 9/1998 | Brudny et al. |
| 5,813,142 A * | 9/1998 | Demon ............... A43B 3/0005 36/28 |
| 5,813,864 A | 9/1998 | Ikuta |
| 5,813,945 A | 9/1998 | Bernacki |
| 5,813,947 A | 9/1998 | Densmore |
| 5,813,953 A | 9/1998 | Whipple |
| 5,816,372 A | 10/1998 | Carlson et al. |
| 5,816,443 A | 10/1998 | Bustos |
| 5,816,981 A | 10/1998 | Hung |
| 5,820,478 A | 10/1998 | Wood et al. |
| 5,820,525 A | 10/1998 | Riley |
| 5,823,618 A | 10/1998 | Fox et al. |
| 5,823,913 A | 10/1998 | Aruin |
| 5,825,983 A | 10/1998 | Park et al. |
| 5,827,154 A | 10/1998 | Gill |
| 5,827,155 A | 10/1998 | Jensen et al. |
| 5,827,158 A | 10/1998 | Drecksel |
| 5,830,107 A | 11/1998 | Brigliadoro |
| 5,830,113 A | 11/1998 | Coody et al. |
| 5,830,114 A | 11/1998 | Halfen et al. |
| 5,833,577 A | 11/1998 | Hurt |
| 5,833,583 A | 11/1998 | Chuang |
| 5,833,584 A | 11/1998 | Piaget et al. |
| 5,833,587 A | 11/1998 | Strong et al. |
| 5,836,770 A | 11/1998 | Powers |
| 5,838,906 A | 11/1998 | Doyle et al. |
| 5,839,990 A | 11/1998 | Virkkala |
| 5,839,993 A | 11/1998 | Fox |
| 5,842,961 A | 12/1998 | Davis |

(56) References Cited

U.S. PATENT DOCUMENTS

| | | |
|---|---|---|
| 5,845,230 A | 12/1998 | Lamberson |
| 5,846,166 A | 12/1998 | Kuo |
| 5,848,396 A | 12/1998 | Gerace |
| 5,848,954 A | 12/1998 | Stearns et al. |
| 5,852,264 A | 12/1998 | Muller |
| 5,854,833 A | 12/1998 | Hogan et al. |
| 5,855,537 A | 1/1999 | Coody et al. |
| 5,855,538 A | 1/1999 | Argabright |
| 5,857,939 A | 1/1999 | Kaufman |
| 5,857,940 A | 1/1999 | Husted |
| 5,857,941 A | 1/1999 | Maresh |
| 5,857,943 A | 1/1999 | Murray |
| 5,860,893 A | 1/1999 | Watterson et al. |
| 5,860,894 A | 1/1999 | Dalebout et al. |
| 5,860,899 A | 1/1999 | Rassman |
| 5,864,018 A | 1/1999 | Morser et al. |
| 5,865,710 A | 2/1999 | Wilson-Hyde |
| 5,865,733 A | 2/1999 | Malinouskas et al. |
| 5,868,108 A | 2/1999 | Schmitz et al. |
| 5,868,648 A | 2/1999 | Coody et al. |
| 5,871,421 A | 2/1999 | Trulaske et al. |
| 5,873,369 A | 2/1999 | Laniado et al. |
| 5,876,095 A | 3/1999 | Johnston |
| 5,879,270 A | 3/1999 | Huish et al. |
| 5,879,271 A | 3/1999 | Stearns et al. |
| 5,879,273 A | 3/1999 | Wei |
| 5,879,276 A | 3/1999 | Miller |
| 5,880,677 A | 3/1999 | Lestician |
| 5,882,281 A | 3/1999 | Stearns et al. |
| 5,885,197 A | 3/1999 | Barton |
| 5,888,172 A | 3/1999 | Andrus et al. |
| 5,890,149 A | 3/1999 | Schmonsees |
| 5,890,562 A | 4/1999 | Bartels et al. |
| 5,890,906 A | 4/1999 | Macri |
| 5,890,995 A | 4/1999 | Bobick et al. |
| 5,890,996 A | 4/1999 | Frame et al. |
| 5,890,997 A | 4/1999 | Roth |
| 5,891,001 A | 4/1999 | Carnes et al. |
| 5,891,003 A | 4/1999 | Deac et al. |
| 5,891,042 A | 4/1999 | Sham et al. |
| 5,895,339 A | 4/1999 | Maresh |
| 5,895,340 A | 4/1999 | Keller |
| 5,897,457 A | 4/1999 | Mackovjak |
| 5,897,459 A | 4/1999 | Habing et al. |
| 5,897,460 A | 4/1999 | McBride et al. |
| 5,897,461 A | 4/1999 | Socwell |
| 5,897,463 A | 4/1999 | Maresh |
| 5,899,833 A | 5/1999 | Ryan et al. |
| 5,899,834 A | 5/1999 | Dalebout et al. |
| 5,899,963 A | 5/1999 | Hutchings |
| 5,902,214 A | 5/1999 | Makikawa et al. |
| 5,904,398 A | 5/1999 | Farricielli |
| 5,904,636 A | 5/1999 | Chen |
| 5,905,442 A | 5/1999 | Mosebrook et al. |
| 5,906,269 A | 5/1999 | Zabron et al. |
| 5,906,494 A | 5/1999 | Ogawa et al. |
| 5,906,564 A | 5/1999 | Jacobsen |
| 5,906,581 A | 5/1999 | Tsuda |
| 5,909,544 A | 6/1999 | Anderson, II et al. |
| 5,910,070 A | 6/1999 | Henry et al. |
| 5,910,072 A | 6/1999 | Rawls et al. |
| 5,911,044 A | 6/1999 | Lo et al. |
| 5,911,132 A | 6/1999 | Sloane |
| 5,911,687 A | 6/1999 | Sato et al. |
| 5,913,310 A | 6/1999 | Brown |
| 5,913,751 A | 6/1999 | Eschenbach |
| 5,913,830 A | 6/1999 | Miles |
| 5,916,063 A | 6/1999 | Alessandri |
| 5,916,064 A | 6/1999 | Eschenbach |
| 5,916,065 A | 6/1999 | McBride et al. |
| 5,916,069 A | 6/1999 | Wang |
| 5,917,405 A | 6/1999 | Joao |
| 5,917,692 A | 6/1999 | Schmitz et al. |
| 5,919,117 A | 7/1999 | Thompson et al. |
| 5,919,118 A | 7/1999 | Stearns |
| 5,921,891 A | 7/1999 | Browne |
| 5,921,892 A | 7/1999 | Easton |
| 5,921,896 A | 7/1999 | Boland |
| 5,925,001 A | 7/1999 | Hoyt et al. |
| 5,929,748 A | 7/1999 | Odinak |
| 5,929,782 A | 7/1999 | Stark |
| 5,929,848 A | 7/1999 | Albukerk et al. |
| 5,931,763 A | 8/1999 | Alessandri |
| 5,937,387 A | 8/1999 | Gonzalez |
| 5,938,551 A | 8/1999 | Warner |
| 5,938,565 A | 8/1999 | Bernacki |
| 5,938,570 A | 8/1999 | Maresh |
| 5,938,571 A | 8/1999 | Stevens |
| 5,938,575 A | 8/1999 | Stearns |
| 5,940,502 A | 8/1999 | Hirai et al. |
| 5,940,911 A | 8/1999 | Wang |
| 5,941,797 A | 8/1999 | Kashiwaguchi |
| 5,941,807 A | 8/1999 | Cassidy |
| 5,943,794 A | 8/1999 | Gelsomini |
| 5,944,638 A | 8/1999 | Maresh |
| 5,944,641 A | 8/1999 | Habing |
| 5,947,868 A | 9/1999 | Dugan |
| 5,947,869 A | 9/1999 | Shea |
| 5,947,872 A | 9/1999 | Ryan et al. |
| 5,951,444 A | 9/1999 | Webber |
| 5,951,447 A | 9/1999 | Butler |
| 5,951,449 A | 9/1999 | Oppriecht |
| 5,956,509 A | 9/1999 | Kevner |
| 5,957,699 A | 9/1999 | Peterson et al. |
| 5,957,814 A | 9/1999 | Eschenbach |
| 5,961,423 A | 10/1999 | Sellers |
| 5,961,430 A | 10/1999 | Zuckerman et al. |
| 5,961,561 A | 10/1999 | Wakefield, II |
| 5,961,593 A | 10/1999 | Gabber et al. |
| 5,964,701 A | 10/1999 | Asada et al. |
| 5,967,944 A | 10/1999 | Vittone et al. |
| 5,967,954 A | 10/1999 | Habing |
| 5,967,955 A | 10/1999 | Westfall et al. |
| 5,967,975 A | 10/1999 | Ridgeway |
| 5,970,340 A | 10/1999 | Edgar |
| 5,971,902 A | 10/1999 | Robertson et al. |
| 5,973,696 A | 10/1999 | Agranat et al. |
| 5,976,039 A | 11/1999 | Epel et al. |
| 5,976,061 A | 11/1999 | Moon et al. |
| 5,976,083 A | 11/1999 | Richardson et al. |
| 5,980,429 A | 11/1999 | Nashner |
| 5,980,430 A | 11/1999 | Wang |
| 5,980,432 A | 11/1999 | Ahman |
| 5,981,168 A | 11/1999 | Reiner et al. |
| 5,984,798 A | 11/1999 | Gilmour |
| 5,984,839 A | 11/1999 | Corkum |
| 5,989,161 A | 11/1999 | Wang et al. |
| 5,989,163 A | 11/1999 | Rodgers, Jr. |
| 5,989,168 A | 11/1999 | See |
| 5,990,405 A | 11/1999 | Auten et al. |
| 5,991,143 A | 11/1999 | Wright et al. |
| 5,993,356 A | 11/1999 | Houston et al. |
| 5,993,358 A | 11/1999 | Gureghian et al. |
| 5,993,359 A | 11/1999 | Eschenbach |
| 5,993,362 A | 11/1999 | Ghobadi |
| 5,995,868 A | 11/1999 | Dorfmeister et al. |
| 5,997,447 A | 12/1999 | Giannelli et al. |
| 5,997,450 A | 12/1999 | Wilkinson |
| 5,997,476 A | 12/1999 | Brown |
| 6,002,982 A | 12/1999 | Fry |
| 6,003,481 A | 12/1999 | Pischinger et al. |
| 6,004,243 A | 12/1999 | Ewert |
| 6,004,244 A | 12/1999 | Simonson |
| 6,006,379 A | 12/1999 | Hensley |
| 6,010,432 A | 1/2000 | Vawter |
| 6,010,451 A | 1/2000 | Clawson |
| 6,012,591 A | 1/2000 | Brandenberg |
| 6,012,772 A | 1/2000 | Conde et al. |
| 6,013,007 A | 1/2000 | Root et al. |
| 6,013,009 A | 1/2000 | Karkanen |
| 6,013,011 A | 1/2000 | Moore et al. |
| 6,014,432 A | 1/2000 | Modney |
| 6,014,634 A | 1/2000 | Scroggie et al. |
| 6,015,367 A | 1/2000 | Scaramucci |

(56) References Cited

U.S. PATENT DOCUMENTS

| | | |
|---|---|---|
| 6,015,368 A | 1/2000 | Clem |
| 6,018,705 A | 1/2000 | Gaudet et al. |
| 6,027,428 A | 2/2000 | Thomas et al. |
| 6,027,429 A | 2/2000 | Daniels |
| 6,027,430 A | 2/2000 | Stearns et al. |
| 6,027,432 A | 2/2000 | Cheng |
| 6,029,858 A | 2/2000 | Srokose |
| 6,030,320 A | 2/2000 | Stearns |
| 6,030,323 A | 2/2000 | Fontenot |
| 6,033,227 A | 3/2000 | Ishige |
| 6,033,344 A | 3/2000 | Trulaske et al. |
| 6,033,347 A | 3/2000 | Dalebout et al. |
| 6,033,350 A | 3/2000 | Krull |
| 6,036,622 A | 3/2000 | Gordon |
| 6,039,677 A | 3/2000 | Spletzer |
| 6,042,512 A | 3/2000 | Eschenbach |
| 6,042,514 A | 3/2000 | Abelbeck |
| 6,042,515 A | 3/2000 | Wang |
| 6,042,516 A | 3/2000 | Norton |
| 6,042,518 A | 3/2000 | Hildebrandt et al. |
| 6,042,519 A | 3/2000 | Shea |
| 6,042,523 A | 3/2000 | Graham |
| 6,045,487 A | 4/2000 | Miller |
| 6,045,488 A | 4/2000 | Eschenbach |
| 6,045,490 A | 4/2000 | Shafer |
| 6,045,491 A | 4/2000 | McNergney |
| 6,050,822 A | 4/2000 | Faughn |
| 6,050,920 A | 4/2000 | Ehrenfried |
| 6,050,921 A | 4/2000 | Wang |
| 6,050,922 A | 4/2000 | Wang |
| 6,050,923 A | 4/2000 | Yu |
| 6,050,924 A | 4/2000 | Shea |
| 6,050,942 A | 4/2000 | Rust et al. |
| 6,053,737 A | 4/2000 | Babbitt et al. |
| 6,053,844 A | 4/2000 | Clem |
| 6,053,847 A | 4/2000 | Stearns et al. |
| 6,053,848 A | 4/2000 | Eschenbach |
| 6,055,513 A | 4/2000 | Katz et al. |
| 6,055,573 A | 4/2000 | Gardenswartz et al. |
| 6,055,747 A | 5/2000 | Lombardino |
| 6,056,670 A | 5/2000 | Shu et al. |
| 6,056,678 A | 5/2000 | Giannelli et al. |
| 6,059,576 A | 5/2000 | Brann |
| 6,059,692 A | 5/2000 | Hickman |
| 6,059,695 A | 5/2000 | Hung |
| 6,063,009 A | 5/2000 | Stearns |
| 6,065,572 A | 5/2000 | Schober et al. |
| 6,066,075 A | 5/2000 | Poulton |
| 6,066,077 A | 5/2000 | Horst |
| 6,066,705 A | 5/2000 | Calderon et al. |
| 6,068,578 A | 5/2000 | Wang |
| 6,068,579 A | 5/2000 | Killian et al. |
| 6,071,031 A | 6/2000 | Bailey |
| 6,071,216 A | 6/2000 | Giannelli et al. |
| 6,075,525 A | 6/2000 | Hsieh |
| 6,077,196 A | 6/2000 | Eschenbach |
| 6,077,198 A | 6/2000 | Eschenbach |
| 6,077,199 A | 6/2000 | Hsu |
| 6,077,200 A | 6/2000 | Lin |
| 6,080,091 A | 6/2000 | Habing et al. |
| 6,086,379 A | 7/2000 | Pendergast et al. |
| 6,086,520 A | 7/2000 | Rodriquez |
| 6,090,014 A | 7/2000 | Eschenbach |
| 6,090,016 A | 7/2000 | Kuo |
| 6,090,017 A | 7/2000 | Wang |
| 6,095,951 A | 8/2000 | Skowronski et al. |
| 6,099,439 A | 8/2000 | Ryan et al. |
| 6,102,412 A | 8/2000 | Staffaroni |
| 6,102,832 A | 8/2000 | Tani |
| 6,102,846 A | 8/2000 | Patton et al. |
| 6,103,203 A | 8/2000 | Fischer |
| 6,106,297 A | 8/2000 | Pollak et al. |
| 6,110,076 A | 8/2000 | Hurt |
| 6,110,077 A | 8/2000 | Yu |
| 6,113,188 A | 9/2000 | Stewart et al. |
| 6,113,522 A | 9/2000 | Montgomery |
| 6,113,537 A | 9/2000 | Castano |
| 6,117,049 A | 9/2000 | Lowe |
| 6,120,421 A | 9/2000 | Kuo |
| 6,122,340 A | 9/2000 | Darley et al. |
| 6,123,646 A | 9/2000 | Colassi |
| 6,123,647 A | 9/2000 | Mitchell |
| 6,123,648 A | 9/2000 | Stevens |
| 6,123,649 A | 9/2000 | Lee |
| 6,123,650 A | 9/2000 | Birrell |
| 6,125,851 A | 10/2000 | Walker et al. |
| 6,126,574 A | 10/2000 | Stearns et al. |
| 6,126,575 A | 10/2000 | Wang |
| 6,126,576 A | 10/2000 | Wang |
| 6,126,577 A | 10/2000 | Chang |
| 6,128,663 A | 10/2000 | Thomas |
| 6,129,962 A | 10/2000 | Quigley et al. |
| 6,132,337 A | 10/2000 | Krupka et al. |
| 6,132,340 A | 10/2000 | Wang |
| 6,133,610 A | 10/2000 | Bolam et al. |
| 6,135,924 A | 10/2000 | Gibbs et al. |
| 6,135,925 A | 10/2000 | Liu |
| 6,142,870 A | 11/2000 | Wada et al. |
| 6,142,912 A | 11/2000 | Profaci |
| 6,142,913 A | 11/2000 | Ewert |
| 6,142,914 A | 11/2000 | Crawford et al. |
| 6,142,915 A | 11/2000 | Eschenbach |
| 6,146,313 A | 11/2000 | Whan-Tong et al. |
| 6,146,315 A | 11/2000 | Schonenberger |
| 6,148,262 A | 11/2000 | Fry |
| 6,149,551 A | 11/2000 | Pyles et al. |
| 6,149,552 A | 11/2000 | Chen |
| 6,151,586 A | 11/2000 | Brown |
| 6,152,854 A | 11/2000 | Carmein |
| 6,152,856 A | 11/2000 | Studor et al. |
| 6,152,859 A | 11/2000 | Stearns |
| 6,159,131 A | 12/2000 | Pfeffer |
| 6,162,151 A | 12/2000 | Tani et al. |
| 6,162,183 A | 12/2000 | Hoover |
| 6,162,189 A | 12/2000 | Girone et al. |
| 6,163,451 A | 12/2000 | Chiu |
| 6,165,107 A | 12/2000 | Birrell |
| 6,168,551 B1 | 1/2001 | Mcguinness |
| 6,171,186 B1 | 1/2001 | Kurosawa et al. |
| 6,171,216 B1 | 1/2001 | Wang |
| 6,171,218 B1 | 1/2001 | Shea |
| 6,174,267 B1 | 1/2001 | Dalebout |
| 6,174,268 B1 | 1/2001 | Novak |
| 6,175,608 B1 | 1/2001 | Pyles et al. |
| 6,176,241 B1 | 1/2001 | Blau et al. |
| 6,176,814 B1 | 1/2001 | Ryan et al. |
| 6,179,746 B1 | 1/2001 | Delman |
| 6,179,753 B1 | 1/2001 | Barker et al. |
| 6,181,647 B1 | 1/2001 | Tipton et al. |
| 6,183,259 B1 | 2/2001 | Macri et al. |
| 6,183,397 B1 | 2/2001 | Stearns et al. |
| 6,183,425 B1 | 2/2001 | Whalen |
| 6,186,145 B1 | 2/2001 | Brown |
| 6,186,290 B1 | 2/2001 | Carlson |
| 6,186,460 B1 | 2/2001 | Lin |
| 6,186,929 B1 | 2/2001 | Endelman et al. |
| 6,189,846 B1 | 2/2001 | Wang |
| 6,190,289 B1 | 2/2001 | Pyles et al. |
| 6,193,631 B1 | 2/2001 | Hickman |
| 6,193,635 B1 | 2/2001 | Webber et al. |
| 6,198,394 B1 | 3/2001 | Jacobsen et al. |
| 6,203,474 B1 | 3/2001 | Jones |
| 6,206,795 B1 | 3/2001 | Ou |
| 6,210,305 B1 | 4/2001 | Eschenbach |
| 6,211,451 B1 | 4/2001 | Tohgi et al. |
| 6,213,919 B1 | 4/2001 | Wang |
| 6,215,870 B1 | 4/2001 | Hirai et al. |
| 6,217,487 B1 | 4/2001 | Reinert |
| 6,220,865 B1 | 4/2001 | Macri et al. |
| 6,220,990 B1 | 4/2001 | Crivello |
| 6,220,995 B1 | 4/2001 | Chen |
| 6,221,451 B1 | 4/2001 | Lauer et al. |
| 6,221,667 B1 | 4/2001 | Reiner et al. |
| 6,224,387 B1 | 5/2001 | Jones |

(56) References Cited

U.S. PATENT DOCUMENTS

| | | |
|---|---|---|
| 6,224,516 B1 | 5/2001 | Disch |
| 6,224,519 B1 | 5/2001 | Doolittle |
| 6,225,977 B1 | 5/2001 | Li |
| 6,227,968 B1 | 5/2001 | Suzuki et al. |
| 6,230,047 B1 | 5/2001 | McHugh |
| 6,230,460 B1 | 5/2001 | Huyett |
| 6,230,501 B1 | 5/2001 | Bailey, Sr. et al. |
| 6,231,481 B1 | 5/2001 | Brock |
| 6,231,482 B1 | 5/2001 | Thompson |
| 6,231,946 B1 | 5/2001 | Brown, Jr. et al. |
| 6,234,935 B1 | 5/2001 | Chu |
| 6,234,936 B1 | 5/2001 | Wang |
| 6,237,583 B1 | 5/2001 | Ripley et al. |
| 6,238,323 B1 | 5/2001 | Simonson |
| 6,241,524 B1 | 6/2001 | Aoshima et al. |
| 6,241,638 B1 | 6/2001 | Hurt |
| 6,244,987 B1 | 6/2001 | Ohsuga et al. |
| 6,244,988 B1 | 6/2001 | Delman |
| 6,244,992 B1 | 6/2001 | James |
| 6,245,001 B1 | 6/2001 | Siaperas |
| 6,251,047 B1 | 6/2001 | Stearns et al. |
| 6,251,048 B1 | 6/2001 | Kaufman |
| 6,252,153 B1 | 6/2001 | Toyama |
| 6,254,513 B1 | 7/2001 | Takenaka et al. |
| 6,254,514 B1 | 7/2001 | Maresh et al. |
| 6,254,515 B1 | 7/2001 | Carman et al. |
| 6,259,944 B1 | 7/2001 | Margulis et al. |
| 6,260,970 B1 | 7/2001 | Horn |
| 6,261,209 B1 | 7/2001 | Coody |
| 6,264,586 B1 | 7/2001 | Webber |
| 6,267,710 B1 | 7/2001 | Liu |
| 6,273,842 B1 | 8/2001 | Wang |
| 6,273,843 B1 | 8/2001 | Lo |
| 6,276,749 B1 | 8/2001 | Okazawa et al. |
| 6,277,054 B1 | 8/2001 | Kuo |
| 6,277,056 B1 | 8/2001 | McBride et al. |
| 6,278,378 B1 | 8/2001 | Feiner et al. |
| 6,280,361 B1 | 8/2001 | Harvey et al. |
| 6,280,362 B1 | 8/2001 | Dalebout et al. |
| 6,280,367 B1 | 8/2001 | Arsenault |
| 6,282,816 B1 | 9/2001 | Rosendahl |
| 6,283,760 B1 | 9/2001 | Wakamoto |
| 6,283,859 B1 | 9/2001 | Carlson et al. |
| 6,283,896 B1 | 9/2001 | Grunfeld |
| 6,287,239 B1 | 9/2001 | Hernandez |
| 6,287,240 B1 | 9/2001 | Trabbic |
| 6,292,688 B1 | 9/2001 | Patton |
| 6,293,375 B1 | 9/2001 | Chen |
| 6,293,802 B1 | 9/2001 | Ahlgren |
| 6,299,959 B1 | 10/2001 | Squires et al. |
| 6,302,815 B1 | 10/2001 | Shishido et al. |
| 6,302,826 B1 | 10/2001 | Lee |
| 6,302,828 B1 | 10/2001 | Martin et al. |
| 6,302,829 B1 | 10/2001 | Schmidt |
| 6,302,830 B1 | 10/2001 | Stearns |
| 6,302,833 B1 | 10/2001 | Ellis et al. |
| 6,306,108 B1 | 10/2001 | Butler |
| 6,307,167 B1 | 10/2001 | Kajio et al. |
| 6,308,565 B1 | 10/2001 | French |
| 6,312,363 B1 | 11/2001 | Watterson et al. |
| 6,312,366 B1 | 11/2001 | Prusick |
| 6,313,363 B1 | 11/2001 | Joly et al. |
| 6,314,058 B1 | 11/2001 | Lee |
| 6,314,667 B1 | 11/2001 | Rife et al. |
| 6,315,486 B1 | 11/2001 | Lunz |
| 6,317,151 B1 | 11/2001 | Ohsuga et al. |
| 6,322,059 B1 | 11/2001 | Kelm et al. |
| 6,322,451 B1 | 11/2001 | Miura |
| 6,322,481 B1 | 11/2001 | Krull |
| 6,325,745 B1 | 12/2001 | Yu |
| 6,325,746 B1 | 12/2001 | Wang |
| 6,328,676 B1 | 12/2001 | Alessandri |
| 6,328,677 B1 | 12/2001 | Drapeau |
| 6,334,624 B1 | 1/2002 | Giglio |
| 6,336,891 B1 | 1/2002 | Fedrigon et al. |
| 6,342,028 B1 | 1/2002 | De Sane |
| 6,344,986 B1 | 2/2002 | Jain et al. |
| 6,345,197 B1 | 2/2002 | Fabrizio |
| 6,347,603 B1 | 2/2002 | Felger |
| 6,348,028 B1 | 2/2002 | Cragg |
| 6,350,218 B1 | 2/2002 | Dalebout et al. |
| 6,352,494 B2 | 3/2002 | McAlonan |
| 6,356,856 B1 | 3/2002 | Damen et al. |
| 6,357,077 B1 | 3/2002 | Jones, Jr. et al. |
| 6,358,187 B1 | 3/2002 | Smith |
| 6,361,476 B1 | 3/2002 | Eschenbach |
| 6,368,251 B1 | 4/2002 | Casler |
| 6,368,252 B1 | 4/2002 | Stearns |
| 6,368,254 B1 | 4/2002 | Wall |
| 6,369,313 B2 | 4/2002 | Devecka |
| 6,371,123 B1 | 4/2002 | Stark et al. |
| 6,371,738 B2 | 4/2002 | Jones |
| 6,371,850 B1 | 4/2002 | Sonoda |
| 6,371,895 B1 | 4/2002 | Endelman et al. |
| 6,375,580 B1 | 4/2002 | Schmidt |
| 6,379,289 B1 | 4/2002 | Gossie |
| 6,382,627 B1 | 5/2002 | Lundberg |
| 6,383,120 B1 | 5/2002 | Lo |
| 6,385,651 B2 | 5/2002 | Dancs et al. |
| 6,387,015 B1 | 5/2002 | Watson |
| 6,387,016 B1 | 5/2002 | Lo |
| 6,390,923 B1 | 5/2002 | Yoshitomi et al. |
| 6,390,953 B1 | 5/2002 | Maresh |
| 6,390,955 B1 | 5/2002 | Wang |
| 6,394,239 B1 | 5/2002 | Carlson |
| 6,397,797 B1 | 6/2002 | Kolmanovsky et al. |
| 6,398,695 B2 | 6/2002 | Miller |
| 6,402,520 B1 | 6/2002 | Freer |
| 6,402,558 B1 | 6/2002 | Hung-Ju et al. |
| 6,402,666 B2 | 6/2002 | Krull |
| 6,404,418 B1 | 6/2002 | Leem |
| 6,405,077 B1 | 6/2002 | Birnbaum et al. |
| 6,409,513 B1 | 6/2002 | Kawamura et al. |
| 6,409,632 B1 | 6/2002 | Eschenbach |
| 6,409,633 B1 | 6/2002 | Abelbeck |
| 6,413,197 B2 | 7/2002 | McKechnie et al. |
| 6,416,442 B1 | 7/2002 | Stearns et al. |
| 6,416,444 B1 | 7/2002 | Lim |
| 6,418,394 B1 | 7/2002 | Puolakanaho et al. |
| 6,419,611 B1 | 7/2002 | Levine et al. |
| 6,421,358 B1 | 7/2002 | Stimmel et al. |
| 6,422,976 B1 | 7/2002 | Eschenbach |
| 6,422,977 B1 | 7/2002 | Eschenbach |
| 6,422,983 B1 | 7/2002 | Weck |
| 6,428,449 B1 | 8/2002 | Apseloff |
| 6,430,997 B1 | 8/2002 | French et al. |
| 6,432,026 B1 | 8/2002 | Wang |
| 6,435,466 B1 | 8/2002 | Adams |
| 6,436,007 B1 | 8/2002 | Eschenbach |
| 6,436,008 B1 | 8/2002 | Skowronski et al. |
| 6,440,013 B1 | 8/2002 | Brown |
| 6,440,042 B2 | 8/2002 | Eschenbach |
| 6,443,875 B1 | 9/2002 | Golen, Jr. et al. |
| 6,446,745 B1 | 9/2002 | Lee |
| 6,447,424 B1 | 9/2002 | Ashby et al. |
| 6,447,430 B1 | 9/2002 | Webb et al. |
| 6,450,284 B1 | 9/2002 | Sakyo et al. |
| 6,450,922 B1 | 9/2002 | Henderson et al. |
| 6,450,923 B1 | 9/2002 | Vatti |
| 6,450,925 B1 | 9/2002 | Kuo |
| 6,454,679 B1 | 9/2002 | Radow |
| 6,454,682 B1 | 9/2002 | Kuo |
| 6,455,960 B1 | 9/2002 | Trago et al. |
| 6,458,060 B1 | 10/2002 | Watterson et al. |
| 6,458,061 B2 | 10/2002 | Simonson |
| 6,461,275 B1 | 10/2002 | Wang et al. |
| 6,461,279 B1 | 10/2002 | Kuo |
| 6,463,385 B1 | 10/2002 | Fry |
| 6,464,618 B1 | 10/2002 | Shea |
| 6,466,460 B1 | 10/2002 | Rein et al. |
| 6,468,189 B2 | 10/2002 | Alessandri |
| 6,471,622 B1 | 10/2002 | Hammer et al. |
| 6,473,483 B2 | 10/2002 | Pyles |
| 6,474,193 B1 | 11/2002 | Farney |

(56) References Cited

U.S. PATENT DOCUMENTS

| | | |
|---|---|---|
| 6,475,115 B1 | 11/2002 | Candito |
| 6,475,121 B2 | 11/2002 | Wang |
| 6,475,122 B2 | 11/2002 | Wu |
| 6,478,721 B1 | 11/2002 | Hunter |
| 6,478,736 B1 | 11/2002 | Mault |
| 6,482,128 B1 | 11/2002 | Michalow |
| 6,482,130 B1 | 11/2002 | Pasero et al. |
| 6,482,132 B2 | 11/2002 | Eschenbach |
| 6,484,062 B1 | 11/2002 | Kim |
| 6,485,397 B1 | 11/2002 | Manderbacka |
| 6,488,020 B1 | 12/2002 | Rosas-Magallan |
| 6,491,610 B1 | 12/2002 | Henn |
| 6,493,652 B1 | 12/2002 | Ohlenbusch et al. |
| 6,494,814 B1 | 12/2002 | Wang |
| 6,494,817 B2 | 12/2002 | Lake |
| 6,497,426 B2 | 12/2002 | Vanpelt |
| 6,500,097 B1 | 12/2002 | Hall |
| 6,503,173 B2 | 1/2003 | Clem |
| 6,505,503 B1 | 1/2003 | Teresi et al. |
| 6,511,402 B2 | 1/2003 | Shu et al. |
| 6,513,381 B2 | 2/2003 | Fyfe et al. |
| 6,513,532 B2 | 2/2003 | Mault et al. |
| 6,513,669 B2 | 2/2003 | Ozawa et al. |
| 6,514,180 B1 | 2/2003 | Rawls |
| 6,515,593 B1 | 2/2003 | Stark et al. |
| 6,520,891 B1 | 2/2003 | Stephens, Jr. |
| 6,527,674 B1 | 3/2003 | Clem |
| 6,527,678 B1 | 3/2003 | Wang |
| 6,527,685 B2 | 3/2003 | Endelman et al. |
| 6,527,711 B1 | 3/2003 | Stivoric et al. |
| 6,527,712 B1 | 3/2003 | Brown et al. |
| 6,527,796 B1 | 3/2003 | Magovern |
| 6,530,864 B1 | 3/2003 | Parks |
| 6,533,707 B2 | 3/2003 | Wang |
| 6,537,184 B2 | 3/2003 | Kim |
| 6,539,931 B2 | 4/2003 | Trajkovic et al. |
| 6,543,247 B2 | 4/2003 | Strauss |
| 6,544,146 B1 | 4/2003 | Stearns et al. |
| 6,547,701 B1 | 4/2003 | Eschenbach |
| 6,547,702 B1 | 4/2003 | Heidecke |
| 6,551,218 B2 | 4/2003 | Goh |
| 6,551,220 B1 | 4/2003 | Schroeder |
| 6,551,223 B2 | 4/2003 | Cheng |
| 6,554,749 B2 | 4/2003 | Iund et al. |
| 6,558,301 B1 | 5/2003 | Jackson |
| 6,560,903 B1 | 5/2003 | Darley |
| 6,561,951 B2 | 5/2003 | Cannon et al. |
| 6,561,955 B1 | 5/2003 | Dreissigacker et al. |
| 6,561,960 B2 | 5/2003 | Webber |
| 6,563,489 B1 | 5/2003 | Latypov et al. |
| 6,569,061 B2 | 5/2003 | Stearns et al. |
| 6,569,062 B2 | 5/2003 | Wang |
| 6,572,511 B1 | 6/2003 | Volpe |
| 6,572,512 B2 | 6/2003 | Anderson et al. |
| 6,572,513 B2 | 6/2003 | Whan-Tong et al. |
| 6,575,878 B1 | 6/2003 | Choy |
| 6,579,210 B1 | 6/2003 | Stearns et al. |
| 6,579,214 B2 | 6/2003 | Crump |
| 6,582,342 B2 | 6/2003 | Kaufman |
| 6,582,344 B2 | 6/2003 | Tang |
| 6,585,622 B1 | 7/2003 | Shum et al. |
| 6,585,624 B1 | 7/2003 | Chen |
| 6,585,626 B2 | 7/2003 | McBride |
| 6,589,138 B2 | 7/2003 | Dyer et al. |
| 6,592,502 B1 | 7/2003 | Phillips |
| 6,599,223 B2 | 7/2003 | Wang |
| 6,601,016 B1 | 7/2003 | Brown et al. |
| 6,601,358 B1 | 8/2003 | Panatta |
| 6,601,825 B2 | 8/2003 | Bressner et al. |
| 6,602,191 B2 | 8/2003 | Quy |
| 6,604,008 B2 | 8/2003 | Chudley et al. |
| 6,604,023 B1 | 8/2003 | Brown et al. |
| 6,604,419 B2 | 8/2003 | Guzman |
| 6,605,020 B1 | 8/2003 | Huang |
| 6,605,038 B1 | 8/2003 | Teller et al. |
| 6,605,044 B2 | 8/2003 | Bimbaum |
| 6,606,374 B1 | 8/2003 | Rokoff et al. |
| 6,609,478 B2 | 8/2003 | Del Valle |
| 6,610,063 B2 | 8/2003 | Kumar et al. |
| 6,611,789 B1 | 8/2003 | Darley |
| 6,612,170 B2 | 9/2003 | Brown |
| 6,612,492 B1 | 9/2003 | Yen |
| 6,612,969 B2 | 9/2003 | Eschenbach |
| 6,612,971 B1 | 9/2003 | Morris |
| 6,616,578 B2 | 9/2003 | Alessandri |
| 6,619,681 B2 | 9/2003 | Gutierrez |
| 6,619,835 B2 | 9/2003 | Kita |
| 6,620,079 B2 | 9/2003 | Kuo |
| 6,623,407 B2 | 9/2003 | Novak |
| 6,623,409 B1 | 9/2003 | Abelbeck |
| 6,626,799 B2 | 9/2003 | Watterson et al. |
| 6,626,800 B1 | 9/2003 | Casler |
| 6,626,802 B1 | 9/2003 | Rodgers, Jr. |
| 6,626,803 B1 | 9/2003 | Oglesby et al. |
| 6,629,902 B2 | 10/2003 | Murphy et al. |
| 6,629,909 B1 | 10/2003 | Stearns et al. |
| 6,629,910 B1 | 10/2003 | Krull |
| 6,632,161 B1 | 10/2003 | Nir |
| 6,634,992 B1 | 10/2003 | Ogawa |
| 6,634,996 B2 | 10/2003 | Jacobsen |
| 6,635,015 B2 | 10/2003 | Sagel |
| 6,637,811 B2 | 10/2003 | Zheng |
| 6,637,818 B2 | 10/2003 | Williams |
| 6,638,160 B2 | 10/2003 | Yoshitomi |
| 6,645,124 B1 | 11/2003 | Clem |
| 6,645,125 B1 | 11/2003 | Stearns et al. |
| 6,645,126 B1 | 11/2003 | Martin et al. |
| 6,645,130 B2 | 11/2003 | Webber |
| 6,648,353 B1 | 11/2003 | Cabal |
| 6,648,798 B2 | 11/2003 | Yoo |
| 6,648,800 B2 | 11/2003 | Stearns et al. |
| 6,648,801 B2 | 11/2003 | Stearns et al. |
| 6,648,802 B2 | 11/2003 | Ware |
| 6,652,424 B2 | 11/2003 | Dalebout |
| 6,652,425 B1 | 11/2003 | Martin et al. |
| 6,652,429 B2 | 11/2003 | Bushnell |
| 6,656,091 B1 | 12/2003 | Abelbeck |
| 6,659,916 B1 | 12/2003 | Shea |
| 6,659,946 B2 | 12/2003 | Batchelor et al. |
| 6,660,949 B2 | 12/2003 | Kamino et al. |
| 6,661,136 B1 | 12/2003 | Lee |
| 6,663,127 B2 | 12/2003 | Miller |
| 6,663,498 B2 | 12/2003 | Stipan |
| 6,663,500 B2 | 12/2003 | Huang |
| 6,666,800 B2 | 12/2003 | Krull |
| 6,666,801 B1 | 12/2003 | Michalow |
| 6,668,678 B1 | 12/2003 | Baba et al. |
| 6,669,600 B2 | 12/2003 | Warner |
| 6,669,609 B2 | 12/2003 | Gerschefske et al. |
| 6,671,975 B2 | 1/2004 | Hennessey |
| 6,672,991 B2 | 1/2004 | O'Malley |
| 6,672,992 B1 | 1/2004 | Lo et al. |
| 6,672,994 B1 | 1/2004 | Stearns et al. |
| 6,676,530 B2 | 1/2004 | Lochtefeld |
| 6,676,569 B1 | 1/2004 | Radow |
| 6,676,572 B2 | 1/2004 | Wang |
| 6,676,579 B1 | 1/2004 | Lin |
| 6,677,299 B2 | 1/2004 | Stern et al. |
| 6,679,816 B1 | 1/2004 | Krull |
| 6,679,820 B2 | 1/2004 | Barkus et al. |
| 6,681,014 B1 | 1/2004 | Ghassabian |
| 6,681,704 B1 | 1/2004 | Brookhiser |
| 6,681,728 B2 | 1/2004 | Haghgooie |
| 6,682,460 B2 | 1/2004 | Lo |
| 6,682,461 B2 | 1/2004 | Wang |
| 6,685,480 B2 | 2/2004 | Nishimoto et al. |
| 6,685,601 B2 | 2/2004 | Knapp |
| 6,685,602 B2 | 2/2004 | Colosky, Jr. et al. |
| 6,685,607 B1 | 2/2004 | Olson |
| 6,687,535 B2 | 2/2004 | Hautala et al. |
| 6,689,019 B2 | 2/2004 | Ohrt et al. |
| 6,689,057 B1 | 2/2004 | Shinsel et al. |
| 6,691,839 B1 | 2/2004 | El-Kassouf |
| 6,695,694 B2 | 2/2004 | Ishikawa et al. |

(56) References Cited

U.S. PATENT DOCUMENTS

| | | | |
|---|---|---|---|
| 6,695,799 | B2 | 2/2004 | Kitadou et al. |
| 6,698,110 | B1 | 3/2004 | Robbins |
| 6,699,159 | B2 | 3/2004 | Rouse |
| 6,699,162 | B2 | 3/2004 | Chen |
| 6,700,788 | B2 | 3/2004 | Matsushita et al. |
| 6,701,271 | B2 | 3/2004 | Willner et al. |
| 6,702,719 | B1 | 3/2004 | Brown et al. |
| 6,705,977 | B1 | 3/2004 | Ziak |
| 6,708,427 | B2 | 3/2004 | Sussmann et al. |
| 6,712,737 | B1 | 3/2004 | Nusbaum |
| 6,716,139 | B1 | 4/2004 | Hosseinzadeh-Dolkhani |
| 6,716,142 | B2 | 4/2004 | Kuo |
| 6,716,144 | B1 | 4/2004 | Shifferaw |
| 6,719,667 | B2 | 4/2004 | Wong et al. |
| 6,719,669 | B1 | 4/2004 | Wang |
| 6,722,888 | B1 | 4/2004 | Macri et al. |
| 6,723,413 | B2 | 4/2004 | Walters |
| 6,726,113 | B2 | 4/2004 | Guo |
| 6,726,600 | B2 | 4/2004 | Miller |
| 6,726,601 | B1 | 4/2004 | Beutel |
| 6,726,602 | B2 | 4/2004 | Chang |
| 6,730,002 | B2 | 5/2004 | Hald et al. |
| 6,733,423 | B1 | 5/2004 | Chang |
| 6,733,424 | B2 | 5/2004 | Krull |
| 6,736,360 | B1 | 5/2004 | Buczek |
| 6,736,759 | B1 | 5/2004 | Stubbs et al. |
| 6,738,274 | B2 | 5/2004 | Prasad et al. |
| 6,740,007 | B2 | 5/2004 | Gordon et al. |
| 6,740,009 | B1 | 5/2004 | Hall |
| 6,741,052 | B2 | 5/2004 | Fitzgibbon |
| 6,743,153 | B2 | 6/2004 | Watterson et al. |
| 6,746,247 | B2 | 6/2004 | Barton |
| 6,746,371 | B1 | 6/2004 | Brown et al. |
| 6,747,427 | B1 | 6/2004 | Carson |
| 6,749,432 | B2 | 6/2004 | French et al. |
| 6,749,536 | B1 | 6/2004 | Cuskaden et al. |
| 6,749,537 | B1 | 6/2004 | Hickman |
| 6,749,540 | B1 | 6/2004 | Pasero et al. |
| 6,749,542 | B2 | 6/2004 | Wu |
| 6,749,546 | B2 | 6/2004 | Yang |
| 6,751,439 | B2 | 6/2004 | Tice et al. |
| 6,757,572 | B1 | 6/2004 | Forest |
| 6,758,790 | B1 | 7/2004 | Ellis |
| 6,758,791 | B1 | 7/2004 | Kuo |
| 6,758,792 | B1 | 7/2004 | Chang |
| 6,761,387 | B2 | 7/2004 | Sloss |
| 6,761,667 | B1 | 7/2004 | Cutler et al. |
| 6,764,429 | B1 | 7/2004 | Michalow |
| 6,764,430 | B1 | 7/2004 | Fencel |
| 6,764,431 | B2 | 7/2004 | Yoss |
| 6,765,726 | B2 | 7/2004 | French et al. |
| 6,767,314 | B2 | 7/2004 | Thompson |
| 6,769,689 | B1 | 8/2004 | Shimomura et al. |
| 6,770,015 | B2 | 8/2004 | Simonson |
| 6,776,740 | B1 | 8/2004 | Anderson et al. |
| 6,778,938 | B1 | 8/2004 | Ng et al. |
| 6,783,482 | B2 | 8/2004 | Oglesby et al. |
| 6,786,415 | B2 | 9/2004 | Yiu |
| 6,786,821 | B2 | 9/2004 | Nobe et al. |
| 6,786,847 | B1 | 9/2004 | Morgan et al. |
| 6,786,848 | B2 | 9/2004 | Yamashita et al. |
| 6,786,850 | B2 | 9/2004 | Nizamuddin |
| 6,786,852 | B2 | 9/2004 | Watterson et al. |
| 6,790,162 | B1 | 9/2004 | Ellis et al. |
| 6,790,163 | B1 | 9/2004 | Van De Laarschot |
| 6,790,178 | B1 | 9/2004 | Mault et al. |
| 6,793,607 | B2 | 9/2004 | Neil |
| 6,793,609 | B1 | 9/2004 | Fan |
| 6,796,159 | B2 | 9/2004 | Kelm et al. |
| 6,796,927 | B2 | 9/2004 | Toyama |
| 6,798,378 | B1 | 9/2004 | Walters |
| 6,807,869 | B2 | 10/2004 | Farringdon et al. |
| 6,808,458 | B1 | 10/2004 | Jung |
| 6,808,472 | B1 | 10/2004 | Hickman |
| 6,808,473 | B2 | 10/2004 | Hisano et al. |
| 6,808,475 | B2 | 10/2004 | Kehrbaum |
| 6,811,516 | B1 | 11/2004 | Dugan |
| 6,811,519 | B2 | 11/2004 | Kuo |
| 6,811,520 | B2 | 11/2004 | Wu |
| 6,817,117 | B1 | 11/2004 | Campbell |
| 6,817,968 | B2 | 11/2004 | Galbraith et al. |
| 6,817,979 | B2 | 11/2004 | Nihtilä |
| 6,821,230 | B2 | 11/2004 | Dalebout et al. |
| 6,823,036 | B1 | 11/2004 | Chen |
| 6,823,327 | B1 | 11/2004 | Klug |
| 6,824,210 | B2 | 11/2004 | Zheng |
| 6,824,502 | B1 | 11/2004 | Huang |
| 6,825,164 | B1 | 11/2004 | Stern et al. |
| 6,825,876 | B1 | 11/2004 | Easwar et al. |
| 6,827,669 | B2 | 12/2004 | Cohen et al. |
| 6,827,670 | B1 | 12/2004 | Stark et al. |
| 6,827,822 | B2 | 12/2004 | Tao et al. |
| 6,830,540 | B2 | 12/2004 | Watterson |
| 6,830,541 | B2 | 12/2004 | Wu |
| 6,835,166 | B1 | 12/2004 | Stearns et al. |
| 6,837,827 | B1 | 1/2005 | Lee et al. |
| 6,837,829 | B2 | 1/2005 | Eschenbach |
| 6,837,830 | B2 | 1/2005 | Eldridge |
| 6,837,838 | B2 | 1/2005 | List |
| 6,840,892 | B1 | 1/2005 | Wu |
| 6,840,904 | B2 | 1/2005 | Goldberg |
| 6,842,928 | B2 | 1/2005 | Yang et al. |
| 6,843,732 | B1 | 1/2005 | Huang |
| 6,846,270 | B1 | 1/2005 | Etnyre |
| 6,846,272 | B2 | 1/2005 | Rosenow et al. |
| 6,849,032 | B2 | 2/2005 | Chu |
| 6,852,068 | B2 | 2/2005 | Ogawa |
| 6,852,069 | B2 | 2/2005 | Park |
| 6,855,093 | B2 | 2/2005 | Anderson et al. |
| 6,855,097 | B2 | 2/2005 | Krull |
| 6,857,993 | B2 | 2/2005 | Yeh |
| 6,859,215 | B1 | 2/2005 | Brown et al. |
| 6,860,836 | B1 | 3/2005 | Wu |
| 6,860,839 | B1 | 3/2005 | Dice |
| 6,863,641 | B1 | 3/2005 | Brown et al. |
| 6,866,613 | B1 | 3/2005 | Brown et al. |
| 6,872,077 | B2 | 3/2005 | Yeager |
| 6,872,168 | B2 | 3/2005 | Wang et al. |
| 6,872,175 | B2 | 3/2005 | Lin |
| 6,872,187 | B1 | 3/2005 | Stark et al. |
| 6,875,157 | B1 | 4/2005 | Wang |
| 6,875,160 | B2 | 4/2005 | Watterson et al. |
| 6,876,496 | B2 | 4/2005 | French et al. |
| 6,876,947 | B1 | 4/2005 | Darley et al. |
| 6,878,099 | B2 | 4/2005 | Corbalis et al. |
| 6,878,101 | B2 | 4/2005 | Colley |
| 6,880,487 | B2 | 4/2005 | Reinkensmeyer et al. |
| 6,881,176 | B2 | 4/2005 | Oishi et al. |
| 6,882,955 | B1 | 4/2005 | Ohlenbusch et al. |
| 6,885,971 | B2 | 4/2005 | Vock et al. |
| 6,886,613 | B1 | 5/2005 | Zahdeh |
| 6,887,185 | B1 | 5/2005 | Kuo |
| 6,887,190 | B1 | 5/2005 | Azari |
| 6,893,383 | B1 | 5/2005 | Chang et al. |
| 6,896,645 | B1 | 5/2005 | Krull |
| 6,899,657 | B2 | 5/2005 | Chuang |
| 6,899,659 | B2 | 5/2005 | Anderson et al. |
| 6,902,513 | B1 | 6/2005 | Mcclure |
| 6,902,515 | B2 | 6/2005 | Howell et al. |
| 6,905,440 | B2 | 6/2005 | Heppert |
| 6,905,446 | B2 | 6/2005 | Greenland |
| 6,908,416 | B2 | 6/2005 | Mercado et al. |
| 6,908,417 | B2 | 6/2005 | Jackson |
| 6,913,562 | B2 | 7/2005 | Chen |
| 6,913,563 | B2 | 7/2005 | Chen |
| 6,915,271 | B1 | 7/2005 | Meyer et al. |
| 6,916,278 | B2 | 7/2005 | Webber |
| 6,918,858 | B2 | 7/2005 | Watterson et al. |
| 6,918,859 | B1 | 7/2005 | Yeh |
| 6,918,860 | B1 | 7/2005 | Nusbaum |
| 6,921,351 | B1 | 7/2005 | Hickman et al. |
| 6,921,354 | B1 | 7/2005 | Shifferaw |
| 6,921,355 | B2 | 7/2005 | Campanaro et al. |
| 6,923,746 | B1 | 8/2005 | Skowronski et al. |

(56) References Cited

U.S. PATENT DOCUMENTS

| | | |
|---|---|---|
| 6,923,747 B1 | 8/2005 | Chu |
| 6,926,644 B2 | 8/2005 | Chen |
| 6,926,646 B1 | 8/2005 | Nguyen |
| 6,932,745 B1 | 8/2005 | Ellis |
| 6,934,658 B2 | 8/2005 | Clabes et al. |
| 6,936,007 B2 | 8/2005 | Quy |
| 6,937,289 B1 | 8/2005 | Ranta et al. |
| 6,939,271 B1 | 9/2005 | Whan-Tong et al. |
| 6,942,599 B1 | 9/2005 | Racine |
| 6,944,294 B2 | 9/2005 | Tsay |
| 6,945,912 B2 | 9/2005 | Levi |
| 6,945,916 B2 | 9/2005 | Schroeder |
| 6,945,917 B1 | 9/2005 | Baatz |
| 6,949,053 B1 | 9/2005 | Stearns |
| 6,949,054 B1 | 9/2005 | Stearns |
| 6,952,221 B1 | 10/2005 | Holtz et al. |
| 6,953,418 B1 | 10/2005 | Chen |
| 6,955,542 B2 | 10/2005 | Roncalez et al. |
| 6,960,156 B2 | 11/2005 | Smith |
| 6,964,632 B1 | 11/2005 | Ko |
| 6,966,872 B2 | 11/2005 | Eschenbach |
| 6,971,972 B1 | 12/2005 | Mcgovern |
| 6,971,973 B2 | 12/2005 | Cohen et al. |
| 6,974,403 B2 | 12/2005 | Wong et al. |
| 6,974,404 B1 | 12/2005 | Watterson et al. |
| 6,975,910 B1 | 12/2005 | Brown et al. |
| 6,976,624 B2 | 12/2005 | Hsiao |
| 6,976,698 B2 | 12/2005 | Kuiken |
| 6,976,958 B2 | 12/2005 | Quy |
| 6,979,283 B2 | 12/2005 | Pan |
| 6,991,586 B2 | 1/2006 | Lapcevic |
| 6,991,588 B1 | 1/2006 | Adams |
| 6,994,306 B1 | 2/2006 | Sweere et al. |
| 6,994,657 B1 | 2/2006 | Eschenbach |
| 6,996,852 B1 | 2/2006 | Cabrera |
| 6,997,852 B2 | 2/2006 | Watterson et al. |
| 6,997,853 B1 | 2/2006 | Cuskaden et al. |
| 6,997,856 B1 | 2/2006 | Krull |
| 7,001,288 B2 | 2/2006 | Harrell |
| 7,003,122 B2 | 2/2006 | Chen |
| 7,004,271 B1 | 2/2006 | Kamen et al. |
| 7,004,887 B2 | 2/2006 | Pan et al. |
| 7,004,888 B1 | 2/2006 | Weng |
| 7,008,356 B2 | 3/2006 | Hung |
| 7,008,359 B2 | 3/2006 | Fan et al. |
| 7,011,326 B1 | 3/2006 | Schroeder et al. |
| 7,011,607 B2 | 3/2006 | Kolda et al. |
| 7,011,609 B1 | 3/2006 | Kuo |
| 7,015,950 B1 | 3/2006 | Pryor |
| 7,016,812 B2 | 3/2006 | Aritsuka et al. |
| 7,020,508 B2 | 3/2006 | Stivoric |
| 7,022,047 B2 | 4/2006 | Cohen et al. |
| 7,022,048 B1 | 4/2006 | Fernandez |
| 7,022,049 B2 | 4/2006 | Ryan et al. |
| 7,022,051 B2 | 4/2006 | Ota |
| 7,032,870 B2 | 4/2006 | Sweere et al. |
| 7,033,176 B2 | 4/2006 | Feldman |
| 7,033,306 B2 | 4/2006 | Graber |
| 7,035,936 B2 | 4/2006 | Fouquet |
| 7,038,855 B2 | 5/2006 | French et al. |
| 7,039,263 B2 | 5/2006 | Towle |
| 7,041,034 B1 | 5/2006 | Stearns et al. |
| 7,041,038 B2 | 5/2006 | Smith |
| 7,041,041 B2 | 5/2006 | Evans |
| 7,041,049 B1 | 5/2006 | Raniere |
| 7,044,891 B1 | 5/2006 | Rivera |
| 7,051,049 B2 | 5/2006 | Samn |
| 7,052,426 B2 | 5/2006 | Battat et al. |
| 7,052,440 B2 | 5/2006 | Pyles et al. |
| 7,052,444 B2 | 5/2006 | Webber |
| 7,052,446 B2 | 5/2006 | Morris et al. |
| 7,055,899 B2 | 6/2006 | Zhurong et al. |
| 7,056,265 B1 | 6/2006 | Shea |
| 7,060,005 B2 | 6/2006 | Carlsen et al. |
| 7,060,006 B1 | 6/2006 | Watterson et al. |
| 7,060,008 B2 | 6/2006 | Watterson et al. |
| 7,060,031 B2 | 6/2006 | Webb et al. |
| 7,063,644 B2 | 6/2006 | Albert et al. |
| 7,065,768 B1 | 6/2006 | Janzig et al. |
| 7,066,865 B2 | 6/2006 | Radow |
| 7,070,415 B2 | 7/2006 | Hojo et al. |
| 7,070,539 B2 | 7/2006 | Brown et al. |
| 7,070,542 B2 | 7/2006 | Reyes et al. |
| 7,070,545 B2 | 7/2006 | Lull et al. |
| 7,072,789 B2 | 7/2006 | Vock et al. |
| 7,073,852 B1 | 7/2006 | Zheng |
| 7,077,788 B2 | 7/2006 | Chang |
| 7,077,791 B2 | 7/2006 | Krull |
| 7,081,073 B1 | 7/2006 | Smith |
| 7,082,703 B2 | 8/2006 | Greene et al. |
| 7,086,994 B2 | 8/2006 | Turak et al. |
| 7,090,621 B2 | 8/2006 | Loane |
| 7,090,622 B2 | 8/2006 | Hetrick |
| 7,091,635 B1 | 8/2006 | Gilliland et al. |
| 7,094,184 B1 | 8/2006 | Chen et al. |
| 7,097,591 B2 | 8/2006 | Moon |
| 7,097,593 B2 | 8/2006 | Chang |
| 7,100,517 B1 | 9/2006 | Godwin |
| 7,101,319 B1 | 9/2006 | Potts |
| 7,101,322 B2 | 9/2006 | Carle |
| 7,101,330 B2 | 9/2006 | Elbaz et al. |
| 7,104,926 B2 | 9/2006 | Carlson |
| 7,104,937 B2 | 9/2006 | Arbuckle |
| 7,108,641 B2 | 9/2006 | Pertegaz-Esteban |
| 7,108,659 B2 | 9/2006 | Ross et al. |
| 7,113,166 B1 | 9/2006 | Rosenberg et al. |
| 7,115,073 B2 | 10/2006 | Nizamuddin |
| 7,115,076 B2 | 10/2006 | Oglesby et al. |
| 7,121,980 B2 | 10/2006 | Chen |
| 7,125,371 B2 | 10/2006 | Henderson |
| 7,128,692 B2 | 10/2006 | Black |
| 7,128,693 B2 | 10/2006 | Brown et al. |
| 7,132,939 B2 | 11/2006 | Tyndall et al. |
| 7,139,835 B2 | 11/2006 | Fouquet et al. |
| 7,140,626 B1 | 11/2006 | Keay |
| 7,141,008 B2 | 11/2006 | Krull et al. |
| 7,148,879 B2 | 12/2006 | Amento et al. |
| 7,151,214 B2 | 12/2006 | Barry |
| 7,156,776 B1 | 1/2007 | Maser |
| 7,156,808 B2 | 1/2007 | Quy |
| 7,156,809 B2 | 1/2007 | Quy |
| 7,158,938 B2 | 1/2007 | Labbe et al. |
| 7,163,489 B1 | 1/2007 | Nelson |
| 7,163,493 B1 | 1/2007 | Kuo |
| 7,163,498 B1 | 1/2007 | Abelbeck |
| 7,163,500 B2 | 1/2007 | Endelman et al. |
| 7,166,062 B1 | 1/2007 | Watterson et al. |
| 7,166,064 B2 | 1/2007 | Watterson et al. |
| 7,166,067 B2 | 1/2007 | Talish et al. |
| 7,168,668 B2 | 1/2007 | Coyle |
| 7,169,087 B2 | 1/2007 | Ercanbrack et al. |
| 7,169,088 B2 | 1/2007 | Rodgers, Jr. |
| 7,169,093 B2 | 1/2007 | Simonson et al. |
| 7,170,016 B2 | 1/2007 | Dumornay |
| 7,171,331 B2 | 1/2007 | Vock et al. |
| 7,172,531 B2 | 2/2007 | Rodgers, Jr. |
| 7,175,193 B2 | 2/2007 | Wu |
| 7,179,207 B2 | 2/2007 | Gerschefske |
| 7,179,208 B1 | 2/2007 | Nalley |
| 7,179,209 B2 | 2/2007 | Sechrest et al. |
| 7,182,738 B2 | 2/2007 | Bonutti et al. |
| 7,186,189 B2 | 3/2007 | Huang |
| 7,187,961 B2 | 3/2007 | Yamashita et al. |
| 7,188,439 B2 | 3/2007 | DiBenedetto et al. |
| 7,192,387 B2 | 3/2007 | Mendel |
| 7,192,388 B2 | 3/2007 | Dalebout et al. |
| 7,195,568 B2 | 3/2007 | Huang |
| 7,197,029 B1 | 3/2007 | Osterhout et al. |
| 7,200,517 B2 | 4/2007 | Darley et al. |
| 7,201,705 B2 | 4/2007 | Rodgers, Jr. |
| 7,201,707 B1 | 4/2007 | Moon |
| 7,204,328 B2 | 4/2007 | LoPresti |
| 7,207,930 B2 | 4/2007 | Bonutti |
| 7,211,029 B2 | 5/2007 | Kau |

(56) References Cited

U.S. PATENT DOCUMENTS

| | | |
|---|---|---|
| 7,217,224 B2 | 5/2007 | Thomas |
| 7,217,225 B2 | 5/2007 | Husted et al. |
| 7,220,219 B2 | 5/2007 | Papadopoulos et al. |
| 7,220,221 B2 | 5/2007 | Mosimann et al. |
| 7,223,209 B2 | 5/2007 | Lee |
| 7,223,213 B2 | 5/2007 | Golesh |
| 7,223,216 B1 | 5/2007 | McBride |
| 7,224,326 B2 | 5/2007 | Sefton |
| 7,225,282 B1 | 5/2007 | Lyle |
| 7,225,565 B2 | 6/2007 | DiBenedetto et al. |
| 7,225,694 B2 | 6/2007 | Said |
| 7,226,402 B1 | 6/2007 | Joya |
| 7,235,942 B2 | 6/2007 | Nagaoka et al. |
| 7,236,154 B1 | 6/2007 | Kerr et al. |
| 7,238,147 B2 | 7/2007 | Mills et al. |
| 7,247,128 B2 | 7/2007 | Oga |
| 7,250,022 B2 | 7/2007 | Dalebout |
| 7,254,516 B2 | 8/2007 | Case, Jr. et al. |
| 7,258,651 B2 | 8/2007 | Clarke |
| 7,259,906 B1 | 8/2007 | Islam |
| 7,264,554 B2 | 9/2007 | Bentley |
| 7,269,038 B2 | 9/2007 | Shekhawat |
| 7,278,934 B2 | 10/2007 | McBride et al. |
| 7,278,955 B2 | 10/2007 | Giannelli et al. |
| 7,278,966 B2 | 10/2007 | Hjelt et al. |
| 7,279,868 B2 | 10/2007 | Lanni |
| 7,285,075 B2 | 10/2007 | Cutler et al. |
| 7,285,090 B2 | 10/2007 | Stivoric et al. |
| 7,287,770 B2 | 10/2007 | Drabant et al. |
| 7,290,760 B1 | 11/2007 | Lindsay |
| 7,291,096 B2 | 11/2007 | Ho |
| 7,292,151 B2 | 11/2007 | Ferguson |
| 7,293,510 B1 | 11/2007 | Siao |
| 7,294,094 B1 | 11/2007 | Howle |
| 7,294,095 B2 | 11/2007 | Charnitski |
| 7,294,100 B2 | 11/2007 | Bull |
| 7,303,508 B2 | 12/2007 | Toyama et al. |
| 7,303,510 B2 | 12/2007 | Gebhardt |
| 7,308,818 B2 | 12/2007 | Considine et al. |
| 7,311,640 B2 | 12/2007 | Baatz |
| 7,316,633 B2 | 1/2008 | Liao et al. |
| 7,319,457 B2 | 1/2008 | Lin et al. |
| 7,322,907 B2 | 1/2008 | Bowser |
| 7,328,119 B1 | 2/2008 | Pryor |
| 7,329,684 B2 | 2/2008 | Mjalli et al. |
| 7,334,350 B2 | 2/2008 | Ellis, III |
| 7,335,139 B2 | 2/2008 | Bartholomew et al. |
| 7,335,140 B2 | 2/2008 | Webber et al. |
| 7,335,147 B2 | 2/2008 | Jones |
| 7,336,178 B2 | 2/2008 | Le |
| 7,344,481 B2 | 3/2008 | Watterson et al. |
| 7,346,935 B1 | 3/2008 | Patterson |
| 7,347,806 B2 | 3/2008 | Nakano et al. |
| 7,350,787 B2 | 4/2008 | Voss |
| 7,351,187 B2 | 4/2008 | Seliber |
| 7,352,365 B2 | 4/2008 | Trachte |
| 7,354,380 B2 | 4/2008 | Volpe, Jr. |
| 7,357,756 B2 | 4/2008 | Demas |
| 7,357,758 B2 | 4/2008 | Polk, III |
| 7,359,121 B2 | 4/2008 | French et al. |
| 7,361,125 B2 | 4/2008 | Webber et al. |
| 7,364,538 B2 | 4/2008 | Aucamp |
| 7,365,647 B2 | 4/2008 | Nativ |
| 7,366,921 B2 | 4/2008 | Ranganathan |
| 7,367,926 B2 | 5/2008 | Clark |
| 7,369,121 B2 | 5/2008 | Lane |
| 7,372,485 B1 | 5/2008 | Bodnar et al. |
| 7,373,820 B1 | 5/2008 | James |
| 7,374,519 B2 | 5/2008 | Naidus |
| 7,374,522 B2 | 5/2008 | Arnold |
| 7,377,881 B2 | 5/2008 | Moon |
| 7,383,081 B2 | 6/2008 | Oy |
| 7,384,013 B2 | 6/2008 | Yen |
| 7,393,308 B1 | 7/2008 | Huang |
| 7,398,151 B1 | 7/2008 | Burrell et al. |
| 7,401,918 B2 | 7/2008 | Howell et al. |
| 7,402,125 B2 | 7/2008 | Wang |
| 7,402,145 B1 | 7/2008 | Woggon |
| 7,412,206 B1 | 8/2008 | Hutchings et al. |
| 7,413,532 B1 | 8/2008 | Monsrud et al. |
| 7,416,537 B1 | 8/2008 | Stark et al. |
| 7,418,862 B2 | 9/2008 | Gruben et al. |
| 7,425,189 B1 | 9/2008 | Eschenbach |
| 7,428,760 B2 | 9/2008 | McCrimmon |
| 7,429,236 B2 | 9/2008 | Dalebout et al. |
| 7,432,184 B2 | 10/2008 | Hosokawa et al. |
| 7,432,454 B1 | 10/2008 | Sze et al. |
| 7,432,677 B2 | 10/2008 | Heydt et al. |
| 7,435,202 B2 | 10/2008 | Daly et al. |
| 7,435,205 B2 | 10/2008 | Reyes et al. |
| 7,452,336 B2 | 11/2008 | Thompson |
| 7,454,002 B1 | 11/2008 | Gardner et al. |
| 7,455,621 B1 | 11/2008 | Anthony |
| 7,455,622 B2 | 11/2008 | Watterson et al. |
| 7,455,626 B2 | 11/2008 | Trevino et al. |
| 7,455,628 B1 | 11/2008 | Stearns |
| 7,462,141 B1 | 12/2008 | Raboin et al. |
| 7,465,257 B1 | 12/2008 | Morgan, Jr. |
| 7,470,234 B1 | 12/2008 | Elhag et al. |
| 7,475,613 B2 | 1/2009 | Bailey |
| 7,477,890 B1 | 1/2009 | Narayanaswami |
| 7,480,512 B2 | 1/2009 | Graham et al. |
| 7,488,277 B1 | 2/2009 | Knapp |
| 7,489,979 B2 | 2/2009 | Rosenberg |
| 7,491,159 B2 | 2/2009 | Patterson |
| 7,494,450 B2 | 2/2009 | Solomon |
| 7,497,784 B2 | 3/2009 | Henry |
| 7,503,476 B2 | 3/2009 | Bhavnani |
| 7,503,878 B1 | 3/2009 | Amsbury et al. |
| 7,507,183 B2 | 3/2009 | Anderson |
| 7,507,187 B2 | 3/2009 | Dyer et al. |
| 7,507,189 B2 | 3/2009 | Krull |
| 7,507,190 B2 | 3/2009 | Piane, Jr. |
| 7,510,509 B2 | 3/2009 | Hickman |
| 7,510,511 B2 | 3/2009 | Von Detten |
| 7,517,303 B2 | 4/2009 | Crawford et al. |
| 7,519,327 B2 | 4/2009 | White |
| 7,519,537 B2 | 4/2009 | Rosenberg |
| 7,520,840 B2 | 4/2009 | Shifferaw |
| 7,521,623 B2 | 4/2009 | Bowen |
| 7,524,272 B2 | 4/2009 | Bruck et al. |
| 7,525,293 B1 | 4/2009 | Notohamiprodjo et al. |
| 7,532,977 B2 | 5/2009 | Chen |
| 7,534,206 B1 | 5/2009 | Lovitt et al. |
| 7,537,546 B2 | 5/2009 | Watterson et al. |
| 7,537,549 B2 | 5/2009 | Nelson et al. |
| 7,537,550 B1 | 5/2009 | Krull |
| 7,537,552 B2 | 5/2009 | Dalebout et al. |
| 7,539,487 B2 | 5/2009 | Sinclair et al. |
| 7,540,828 B2 | 6/2009 | Watterson et al. |
| 7,540,829 B1 | 6/2009 | Lin |
| 7,542,816 B2 | 6/2009 | Rosenberg |
| 7,543,934 B2 | 6/2009 | Howell et al. |
| 7,544,153 B2 | 6/2009 | Trevino et al. |
| 7,549,947 B2 | 6/2009 | Hickman et al. |
| 7,553,260 B2 | 6/2009 | Piaget et al. |
| 7,553,262 B2 | 6/2009 | Piane, Jr. |
| 7,556,590 B2 | 7/2009 | Watterson et al. |
| 7,556,591 B2 | 7/2009 | Chuang |
| 7,559,879 B2 | 7/2009 | Anderson et al. |
| 7,561,989 B2 | 7/2009 | Banks et al. |
| 7,562,117 B2 | 7/2009 | Rosenberg |
| 7,563,203 B2 | 7/2009 | Dalebout et al. |
| 7,563,205 B2 | 7/2009 | Alling |
| 7,569,000 B2 | 8/2009 | Wang |
| 7,569,004 B2 | 8/2009 | Kolomeir |
| 7,575,536 B1 | 8/2009 | Hickman |
| 7,575,537 B2 | 8/2009 | Ellis |
| 7,575,538 B1 | 8/2009 | Clark |
| 7,577,522 B2 | 8/2009 | Rosenberg |
| 7,579,946 B2 | 8/2009 | Case, Jr. |
| 7,585,251 B2 | 9/2009 | Doody, Jr. et al. |
| 7,585,254 B1 | 9/2009 | Vittone |
| 7,585,258 B2 | 9/2009 | Watson et al. |

(56) References Cited

U.S. PATENT DOCUMENTS

| | | |
|---|---|---|
| 7,586,032 B2 | 9/2009 | Louis |
| 7,591,770 B2 | 9/2009 | Stewart et al. |
| 7,591,795 B2 | 9/2009 | Whalen et al. |
| 7,594,877 B2 | 9/2009 | Anderson et al. |
| 7,594,878 B1 | 9/2009 | Joannou |
| 7,598,255 B2 | 10/2009 | Dvorak |
| 7,601,096 B2 | 10/2009 | Negrin |
| 7,601,097 B2 | 10/2009 | Miyamaru et al. |
| 7,601,101 B2 | 10/2009 | Jackson et al. |
| 7,602,301 B1 | 10/2009 | Stirling et al. |
| 7,603,255 B2 | 10/2009 | Case, Jr. et al. |
| 7,604,571 B2 | 10/2009 | Wilkins et al. |
| 7,604,572 B2 | 10/2009 | Stanford |
| 7,604,573 B2 | 10/2009 | Dalebout et al. |
| 7,607,243 B2 | 10/2009 | Berner, Jr. et al. |
| 7,608,015 B2 | 10/2009 | Radow |
| 7,608,021 B1 | 10/2009 | Nalley |
| 7,608,023 B2 | 10/2009 | Casagrande |
| 7,614,639 B2 | 11/2009 | Tholkes et al. |
| 7,614,981 B2 | 11/2009 | Cao |
| 7,616,097 B1 | 11/2009 | Whang |
| 7,618,345 B2 | 11/2009 | Corbalis et al. |
| 7,618,346 B2 | 11/2009 | Crawford et al. |
| 7,618,350 B2 | 11/2009 | Dalebout et al. |
| 7,619,514 B1 | 11/2009 | Stone |
| 7,621,850 B2 | 11/2009 | Piaget et al. |
| 7,621,855 B1 | 11/2009 | Krull |
| 7,625,314 B2 | 12/2009 | Ungari |
| 7,625,315 B2 | 12/2009 | Hickman |
| 7,625,316 B1 | 12/2009 | Amsbury et al. |
| 7,628,730 B1 | 12/2009 | Watterson et al. |
| 7,628,732 B1 | 12/2009 | Porszasz et al. |
| 7,628,737 B2 | 12/2009 | Kowallis et al. |
| 7,631,382 B2 | 12/2009 | DiBenedetto et al. |
| 7,637,847 B1 | 12/2009 | Hickman |
| 7,637,850 B2 | 12/2009 | Lin |
| 7,639,520 B1 | 12/2009 | Zansky et al. |
| 7,641,592 B2 | 1/2010 | Roche |
| 7,643,895 B2 | 1/2010 | Gupta et al. |
| 7,645,212 B2 | 1/2010 | Ashby et al. |
| 7,645,213 B1 | 1/2010 | Watterson |
| 7,645,214 B2 | 1/2010 | Lull |
| 7,645,218 B2 | 1/2010 | Potok et al. |
| 7,647,196 B2 | 1/2010 | Kahn et al. |
| 7,648,443 B2 | 1/2010 | Schenk |
| 7,648,446 B2 | 1/2010 | Chiles et al. |
| 7,648,463 B1 | 1/2010 | Elhag et al. |
| 7,648,858 B2 | 1/2010 | Tang et al. |
| 7,651,442 B2 | 1/2010 | Carlson |
| 7,654,229 B2 | 2/2010 | Smith |
| 7,654,948 B2 | 2/2010 | Kaplan et al. |
| 7,658,694 B2 | 2/2010 | Ungari |
| 7,658,695 B1 | 2/2010 | Amsbury et al. |
| 7,658,698 B2 | 2/2010 | Pacheco et al. |
| 7,662,065 B1 | 2/2010 | Kahn et al. |
| 7,662,282 B2 | 2/2010 | Lee et al. |
| 7,670,263 B2 | 3/2010 | Ellis |
| 7,674,205 B2 | 3/2010 | Dalebout et al. |
| 7,674,206 B2 | 3/2010 | Jones |
| 7,676,332 B2 | 3/2010 | Damen |
| 7,677,518 B2 | 3/2010 | Chouinard et al. |
| 7,677,723 B2 | 3/2010 | Howell et al. |
| 7,678,023 B1 | 3/2010 | Shea |
| 7,682,286 B2 | 3/2010 | Badarneh et al. |
| 7,682,287 B1 | 3/2010 | Hsieh |
| 7,682,290 B2 | 3/2010 | Liao et al. |
| 7,682,291 B2 | 3/2010 | Gill et al. |
| 7,683,252 B2 | 3/2010 | Oliver et al. |
| 7,689,437 B1 | 3/2010 | Teller et al. |
| 7,695,409 B2 | 4/2010 | Helie et al. |
| 7,698,101 B2 | 4/2010 | Alten et al. |
| 7,698,359 B2 | 4/2010 | Wray et al. |
| 7,699,752 B1 | 4/2010 | Anderson |
| 7,699,753 B2 | 4/2010 | Daikeler |
| 7,699,754 B2 | 4/2010 | Schneider |
| 7,699,755 B2 | 4/2010 | Feldman et al. |
| 7,702,781 B2 | 4/2010 | Devolites |
| 7,703,974 B2 | 4/2010 | Bouille |
| 7,704,191 B2 | 4/2010 | Smith et al. |
| 7,704,192 B2 | 4/2010 | Dyer et al. |
| 7,705,230 B2 | 4/2010 | Bowen |
| 7,708,668 B2 | 5/2010 | Rodgers, Jr. |
| 7,708,672 B2 | 5/2010 | Gibson et al. |
| 7,713,171 B1 | 5/2010 | Hickman |
| 7,713,172 B2 | 5/2010 | Watterson et al. |
| 7,713,177 B2 | 5/2010 | Lo |
| 7,717,825 B2 | 5/2010 | Van Der Hoeven |
| 7,717,826 B2 | 5/2010 | Cox et al. |
| 7,717,827 B2 | 5/2010 | Kurunmäki et al. |
| 7,717,828 B2 | 5/2010 | Simonson et al. |
| 7,717,830 B1 | 5/2010 | Charniga et al. |
| 7,717,866 B2 | 5/2010 | Damen |
| 7,722,503 B1 | 5/2010 | Smith et al. |
| 7,722,509 B2 | 5/2010 | Eder |
| 7,725,362 B2 | 5/2010 | Weathers, Jr. |
| 7,727,117 B2 | 6/2010 | Feldman et al. |
| 7,727,125 B2 | 6/2010 | Day |
| 7,728,214 B2 | 6/2010 | Oliver et al. |
| 7,731,634 B2 | 6/2010 | Stewart et al. |
| 7,736,272 B2 | 6/2010 | Martens |
| 7,736,273 B2 | 6/2010 | Cox et al. |
| 7,736,279 B2 | 6/2010 | Dalebout et al. |
| 7,736,280 B2 | 6/2010 | Weier et al. |
| 7,736,281 B2 | 6/2010 | Corbalis et al. |
| 7,739,076 B1 | 6/2010 | Vock et al. |
| 7,740,562 B2 | 6/2010 | Jones |
| 7,740,563 B2 | 6/2010 | Dalebout et al. |
| 7,740,588 B1 | 6/2010 | Sciarra |
| 7,745,716 B1 | 6/2010 | Murphy |
| 7,747,671 B2 | 6/2010 | Ku |
| 7,749,137 B2 | 7/2010 | Watt et al. |
| 7,753,824 B2 | 7/2010 | Wang |
| 7,753,825 B2 | 7/2010 | Jaquish et al. |
| 7,753,830 B1 | 7/2010 | Marsh et al. |
| 7,753,861 B1 | 7/2010 | Kahn et al. |
| 7,758,469 B2 | 7/2010 | Dyer et al. |
| 7,758,523 B2 | 7/2010 | Collings et al. |
| 7,761,300 B2 | 7/2010 | Klingler |
| 7,762,931 B2 | 7/2010 | Fisher et al. |
| 7,762,934 B1 | 7/2010 | Munson, Jr. et al. |
| 7,762,952 B2 | 7/2010 | Lee et al. |
| 7,764,990 B2 | 7/2010 | Martikka et al. |
| 7,765,348 B2 | 7/2010 | Dybsetter |
| 7,766,794 B2 | 8/2010 | Oliver et al. |
| 7,766,797 B2 | 8/2010 | Dalebout |
| 7,766,798 B2 | 8/2010 | Hamilton |
| 7,770,181 B2 | 8/2010 | Snover et al. |
| 7,771,319 B1 | 8/2010 | Lannon |
| 7,771,320 B2 | 8/2010 | Riley et al. |
| 7,771,325 B2 | 8/2010 | Baker |
| 7,771,329 B2 | 8/2010 | Dalebout et al. |
| 7,775,936 B2 | 8/2010 | Wilkinson |
| 7,775,943 B2 | 8/2010 | Vittone |
| 7,780,578 B2 | 8/2010 | Packham |
| 7,789,800 B1 | 9/2010 | Watterson et al. |
| 7,794,014 B2 | 9/2010 | Beall et al. |
| 7,794,363 B2 | 9/2010 | Wang |
| 7,795,824 B2 | 9/2010 | Shen et al. |
| 7,798,942 B2 | 9/2010 | Digiulio |
| 7,805,149 B2 | 9/2010 | Werner et al. |
| 7,806,780 B1 | 10/2010 | Plunkett |
| 7,806,805 B2 | 10/2010 | Barufka et al. |
| 7,806,806 B2 | 10/2010 | Jaquish |
| 7,806,815 B2 | 10/2010 | Fernandez |
| 7,809,153 B2 | 10/2010 | Bravomalo et al. |
| 7,811,200 B2 | 10/2010 | Yin-Liang Lai |
| 7,811,201 B2 | 10/2010 | Mikan et al. |
| 7,811,209 B2 | 10/2010 | Crawford et al. |
| 7,813,715 B2 | 10/2010 | McKillop et al. |
| 7,815,549 B2 | 10/2010 | Crawford et al. |
| 7,815,550 B2 | 10/2010 | Watterson et al. |
| 7,815,554 B2 | 10/2010 | Gibson et al. |
| 7,822,547 B2 | 10/2010 | Lindroos |
| 7,825,319 B2 | 11/2010 | Turner |

(56) References Cited

U.S. PATENT DOCUMENTS

| | | | |
|---|---|---|---|
| 7,827,000 B2 | 11/2010 | Stirling et al. |
| 7,830,570 B2 | 11/2010 | Morita et al. |
| 7,833,129 B2 | 11/2010 | Badarneh |
| 7,833,135 B2 | 11/2010 | Radow |
| 7,837,161 B2 | 11/2010 | Chase |
| 7,837,595 B2 | 11/2010 | Rice |
| 7,837,596 B2 | 11/2010 | Astilean |
| 7,837,599 B2 | 11/2010 | Kowalczewski et al. |
| 7,839,058 B1 * | 11/2010 | Churchill ............ H01L 41/1136 |
| | | 310/332 |
| 7,840,346 B2 | 11/2010 | Huhtala et al. |
| 7,841,967 B1 | 11/2010 | Kahn |
| 7,846,067 B2 | 12/2010 | Hanoun |
| 7,846,070 B2 | 12/2010 | Oglesby et al. |
| 7,846,080 B2 | 12/2010 | Boren |
| 7,854,669 B2 | 12/2010 | Marty et al. |
| 7,857,731 B2 | 12/2010 | Hickman et al. |
| 7,857,732 B2 | 12/2010 | Nielson |
| 7,862,476 B2 | 1/2011 | Radow |
| 7,862,478 B2 | 1/2011 | Watterson et al. |
| 7,862,483 B2 | 1/2011 | Hendrickson et al. |
| 7,867,088 B2 | 1/2011 | Prum |
| 7,871,355 B2 | 1/2011 | Yeh |
| 7,871,357 B2 | 1/2011 | Gibson et al. |
| 7,874,957 B2 | 1/2011 | Hurwitz et al. |
| 7,878,950 B1 | 2/2011 | Bastian |
| 7,883,448 B2 | 2/2011 | Wang |
| 7,887,465 B2 | 2/2011 | Uffelman |
| 7,892,148 B1 | 2/2011 | Stauffer et al. |
| 7,892,149 B2 | 2/2011 | Wu |
| 7,892,150 B1 | 2/2011 | Colley |
| 7,894,177 B2 | 2/2011 | Rothkopf |
| 7,894,849 B2 | 2/2011 | Kass et al. |
| 7,896,782 B2 | 3/2011 | Tamari |
| 7,901,292 B1 | 3/2011 | Uhlir et al. |
| 7,901,323 B2 | 3/2011 | Olason et al. |
| 7,901,325 B2 | 3/2011 | Henderson |
| 7,908,981 B2 | 3/2011 | Agee |
| 7,909,741 B2 | 3/2011 | Kim et al. |
| 7,913,297 B2 | 3/2011 | Wyld |
| 7,914,420 B2 | 3/2011 | Daly et al. |
| 7,914,421 B2 | 3/2011 | Weier et al. |
| 7,914,425 B2 | 3/2011 | Hanoun |
| 7,914,468 B2 | 3/2011 | Shalon et al. |
| 7,917,148 B2 | 3/2011 | Rosenberg |
| 7,918,732 B2 | 4/2011 | Van Noland |
| 7,919,950 B2 | 4/2011 | Uno et al. |
| 7,922,635 B2 | 4/2011 | Lull et al. |
| 7,927,253 B2 | 4/2011 | Vincent |
| 7,927,258 B2 | 4/2011 | Irving et al. |
| 7,931,563 B2 | 4/2011 | Shaw et al. |
| 7,934,983 B1 | 5/2011 | Eisner |
| 7,938,751 B2 | 5/2011 | Nicolas et al. |
| 7,938,752 B1 | 5/2011 | Wang |
| 7,938,755 B1 | 5/2011 | Dyer et al. |
| 7,942,783 B2 | 5/2011 | Ochi |
| 7,942,788 B2 | 5/2011 | Wu |
| 7,946,959 B2 | 5/2011 | Shum et al. |
| 7,946,961 B2 | 5/2011 | Blum et al. |
| 7,946,968 B2 | 5/2011 | Kjellberg |
| 7,949,295 B2 | 5/2011 | Kumar et al. |
| 7,950,297 B2 | 5/2011 | Moore et al. |
| 7,951,046 B1 | 5/2011 | Barber, Jr. |
| 7,953,549 B2 | 5/2011 | Graham et al. |
| 7,955,219 B2 | 6/2011 | Birrell et al. |
| 7,959,124 B2 | 6/2011 | Phifer et al. |
| 7,959,567 B2 | 6/2011 | Stivoric et al. |
| 7,963,889 B2 | 6/2011 | Badarneh et al. |
| 7,967,728 B2 | 6/2011 | Zavadsky |
| 7,968,574 B2 | 6/2011 | Hangauer, Jr. |
| 7,972,245 B2 | 7/2011 | Temple et al. |
| 7,972,247 B2 | 7/2011 | Daikeler |
| 7,972,249 B1 | 7/2011 | Napalan |
| 7,973,231 B2 | 7/2011 | Bowen |
| 7,974,889 B2 | 7/2011 | Raimbeault |
| 7,976,437 B1 | 7/2011 | Von Detten |
| 7,976,518 B2 | 7/2011 | Shaughnessy et al. |
| 7,978,081 B2 | 7/2011 | Shears et al. |
| 7,980,996 B2 | 7/2011 | Hickman |
| 7,981,000 B2 | 7/2011 | Watterson et al. |
| 7,985,164 B2 | 7/2011 | Ashby |
| 7,988,598 B2 | 8/2011 | Trzecieski |
| 7,988,599 B2 | 8/2011 | Ainsworth et al. |
| 7,988,600 B2 | 8/2011 | Rodgers, Jr. |
| 8,001,472 B2 | 8/2011 | Gilley et al. |
| 8,002,671 B1 | 8/2011 | Vigilia |
| 8,002,674 B2 | 8/2011 | Piaget et al. |
| 8,002,684 B2 | 8/2011 | Laurent |
| 8,007,409 B2 | 8/2011 | Elllis |
| RE42,698 E | 9/2011 | Kuo et al. |
| 8,011,242 B2 | 9/2011 | O'neill et al. |
| 8,012,064 B2 | 9/2011 | Martens |
| 8,012,067 B2 | 9/2011 | Joannou |
| 8,012,068 B1 | 9/2011 | Malcolm |
| 8,012,073 B2 | 9/2011 | Barnett |
| 8,021,270 B2 | 9/2011 | Eredita |
| 8,021,277 B2 | 9/2011 | Baudhuin |
| 8,025,607 B2 | 9/2011 | Ranky et al. |
| 8,025,612 B1 | 9/2011 | Buzzanco |
| 8,028,443 B2 | 10/2011 | Case, Jr. |
| 8,029,415 B2 | 10/2011 | Ashby et al. |
| 8,033,959 B2 | 10/2011 | Oleson et al. |
| 8,034,294 B1 | 10/2011 | Goldberg |
| 8,037,017 B2 | 10/2011 | Samn |
| 8,038,577 B2 | 10/2011 | McIntosh |
| 8,040,758 B1 | 10/2011 | Dickinson |
| 8,043,173 B2 | 10/2011 | Menalagha et al. |
| 8,046,803 B1 | 10/2011 | Lee |
| 8,047,965 B2 | 11/2011 | Shea |
| 8,047,966 B2 | 11/2011 | Dorogusker et al. |
| 8,047,970 B2 | 11/2011 | Nalley |
| 8,052,580 B2 | 11/2011 | Saalasti et al. |
| 8,052,584 B2 | 11/2011 | Keiser |
| 8,055,469 B2 | 11/2011 | Kulach et al. |
| 8,056,687 B2 | 11/2011 | Golden et al. |
| 8,057,360 B2 | 11/2011 | Shea |
| 8,057,368 B1 | 11/2011 | Lyszczarz |
| 8,062,182 B2 | 11/2011 | Somers |
| 8,062,192 B1 | 11/2011 | Arstein |
| 8,062,196 B1 | 11/2011 | Khubani |
| 8,065,185 B2 | 11/2011 | Foladare et al. |
| 8,066,514 B2 | 11/2011 | Clarke |
| 8,070,655 B1 | 12/2011 | Napolitano |
| 8,075,453 B1 | 12/2011 | Wilkinson |
| 8,078,426 B2 | 12/2011 | Pipinich et al. |
| 8,079,939 B1 | 12/2011 | Wang |
| 8,082,029 B2 | 12/2011 | Honda |
| 8,083,643 B2 | 12/2011 | Ng et al. |
| 8,083,693 B1 | 12/2011 | McKeon et al. |
| 8,086,421 B2 | 12/2011 | Case, Jr. et al. |
| 8,088,043 B2 | 1/2012 | Andren et al. |
| 8,088,044 B2 | 1/2012 | Tchao et al. |
| 8,092,381 B2 | 1/2012 | Edwards |
| 8,101,843 B2 | 1/2012 | Turner |
| 8,103,379 B2 | 1/2012 | Biba et al. |
| 8,103,517 B2 | 1/2012 | Hinnebusch |
| 8,104,411 B2 | 1/2012 | Fenton |
| 8,105,207 B1 | 1/2012 | Lannon |
| 8,105,213 B2 | 1/2012 | Stewart et al. |
| 8,106,563 B2 | 1/2012 | Ritchey |
| 8,109,858 B2 | 2/2012 | Redmann |
| 8,112,281 B2 | 2/2012 | Yeung et al. |
| 8,113,990 B2 | 2/2012 | Kolman et al. |
| 8,113,991 B2 | 2/2012 | Kutliroff |
| 8,113,994 B2 | 2/2012 | Piaget et al. |
| 8,116,841 B2 | 2/2012 | Bly et al. |
| 8,121,785 B2 | 2/2012 | Swisher et al. |
| 8,123,527 B2 | 2/2012 | Holljes |
| 8,128,533 B2 | 3/2012 | Nakagawa et al. |
| 8,141,276 B2 | 3/2012 | Ellis |
| 8,142,298 B2 | 3/2012 | King et al. |
| 8,142,370 B2 | 3/2012 | Weinberg et al. |
| 8,147,385 B2 | 4/2012 | Crawford et al. |
| 8,152,693 B2 | 4/2012 | Nurmela et al. |

(56) References Cited

U.S. PATENT DOCUMENTS

| | | |
|---|---|---|
| 8,152,695 B2 | 4/2012 | Riley et al. |
| 8,157,706 B2 | 4/2012 | Ainsworth et al. |
| 8,157,731 B2 | 4/2012 | Teller et al. |
| 8,162,804 B2 | 4/2012 | Tagliabue |
| 8,162,857 B2 | 4/2012 | Lanfermann et al. |
| 8,165,893 B1 | 4/2012 | Goldberg et al. |
| 8,167,776 B2 | 5/2012 | Lannon |
| 8,172,723 B1 | 5/2012 | Yanev et al. |
| 8,172,729 B2 | 5/2012 | Ellis |
| 8,172,882 B2 | 5/2012 | Klyce et al. |
| 8,176,101 B2 | 5/2012 | Rosenberg |
| 8,177,688 B2 | 5/2012 | Burnfield et al. |
| 8,182,399 B2 | 5/2012 | Davis et al. |
| 8,188,700 B2 | 5/2012 | Tseng et al. |
| 8,188,868 B2 | 5/2012 | Case, Jr. |
| 8,192,332 B2 | 6/2012 | Baker et al. |
| 8,200,323 B2 | 6/2012 | Dibenedetto et al. |
| 8,213,908 B2 | 7/2012 | Sangster et al. |
| 8,221,290 B2 | 7/2012 | Vincent et al. |
| 8,221,292 B2 | 7/2012 | Barker et al. |
| 8,221,295 B2 | 7/2012 | Wilkins |
| 8,224,429 B2 | 7/2012 | Prstojevich et al. |
| 8,225,024 B2 | 7/2012 | Dybsetter |
| 8,231,506 B2 | 7/2012 | Molyneux et al. |
| 8,235,724 B2 | 8/2012 | Gilley et al. |
| 8,240,430 B2 | 8/2012 | Downey |
| 8,241,118 B2 | 8/2012 | Camhi |
| 8,241,186 B2 | 8/2012 | Brodess et al. |
| 8,241,187 B2 | 8/2012 | Moon et al. |
| 8,249,686 B2 | 8/2012 | Libbus et al. |
| 8,251,874 B2 | 8/2012 | Ashby et al. |
| 8,253,586 B1 | 8/2012 | Matak |
| 8,257,228 B2 | 9/2012 | Quatrochi et al. |
| 8,260,667 B2 | 9/2012 | Graham et al. |
| 8,260,858 B2 | 9/2012 | Belz et al. |
| 8,269,093 B2 | 9/2012 | Naik et al. |
| 8,272,996 B2 | 9/2012 | Weier |
| 8,275,143 B2 | 9/2012 | Johnson |
| 8,275,265 B2 | 9/2012 | Kobyakov et al. |
| 8,276,434 B2 | 10/2012 | Senoo |
| 8,280,259 B2 | 10/2012 | George et al. |
| 8,287,434 B2 | 10/2012 | Zavadsky et al. |
| 8,296,172 B2 | 10/2012 | Marci et al. |
| 8,298,123 B2 | 10/2012 | Hickman |
| 8,306,635 B2 | 11/2012 | Pryor |
| 8,308,794 B2 | 11/2012 | Martinson et al. |
| 8,314,840 B1 | 11/2012 | Funk |
| 8,315,823 B2 | 11/2012 | Berme et al. |
| 8,320,578 B2 | 11/2012 | Kahn et al. |
| 8,321,004 B2 | 11/2012 | Moon et al. |
| 8,323,157 B2 | 12/2012 | Campanaro et al. |
| 8,327,723 B2 | 12/2012 | Roudergues et al. |
| 8,332,544 B1 | 12/2012 | Ralls et al. |
| 8,333,681 B2 | 12/2012 | Schmidt |
| 8,337,335 B2 | 12/2012 | Dugan |
| 8,341,557 B2 | 12/2012 | Pisula et al. |
| 8,343,016 B1 | 1/2013 | Astilean |
| 8,348,840 B2 | 1/2013 | Heit et al. |
| 8,360,785 B2 | 1/2013 | Park et al. |
| 8,360,904 B2 | 1/2013 | Oleson et al. |
| 8,360,936 B2 | 1/2013 | Dibenedetto et al. |
| 8,363,913 B2 | 1/2013 | Boushey et al. |
| 8,364,250 B2 | 1/2013 | Moon et al. |
| 8,364,389 B2 | 1/2013 | Dorogusker et al. |
| 8,368,329 B1 | 2/2013 | Depew et al. |
| 8,369,936 B2 | 2/2013 | Farringdon et al. |
| 8,370,087 B2 | 2/2013 | Zhu et al. |
| 8,371,990 B2 | 2/2013 | Shea |
| 8,374,688 B2 | 2/2013 | Libbus et al. |
| 8,376,910 B2 | 2/2013 | Cheung et al. |
| 8,378,647 B2 | 2/2013 | Yonezawa et al. |
| 8,384,551 B2 | 2/2013 | Ross et al. |
| 8,387,470 B2 | 3/2013 | Tuulari et al. |
| 8,394,005 B2 | 3/2013 | Solow et al. |
| 8,395,366 B2 | 3/2013 | Uno |
| 8,398,546 B2 | 3/2013 | Pacione et al. |
| 8,403,845 B2 | 3/2013 | Stivoric et al. |
| 8,407,623 B2 | 3/2013 | Kerr et al. |
| 8,412,317 B2 | 4/2013 | Mazar |
| 8,419,593 B2 | 4/2013 | Ainsworth et al. |
| 8,429,223 B2 | 4/2013 | Gilley et al. |
| 8,430,770 B2 | 4/2013 | Dugan |
| 8,435,160 B1 | 5/2013 | Clum |
| 8,437,824 B2 | 5/2013 | Moon et al. |
| 8,446,275 B2 | 5/2013 | Utter, II |
| 8,449,620 B2 | 5/2013 | Hakansson et al. |
| 8,452,259 B2 | 5/2013 | Ellis et al. |
| 8,454,437 B2 | 6/2013 | Dugan |
| 8,459,479 B2 | 6/2013 | Yourist |
| 8,460,001 B1 | 6/2013 | Chuang |
| 8,460,189 B2 | 6/2013 | Libbus et al. |
| 8,475,338 B2 | 7/2013 | Greenhill et al. |
| 8,475,346 B2 | 7/2013 | Gerschefske et al. |
| 8,475,367 B1 | 7/2013 | Yuen et al. |
| 8,475,370 B2 | 7/2013 | McCombie et al. |
| 8,480,541 B1 | 7/2013 | Brunts |
| 8,485,944 B2 | 7/2013 | Drazan |
| 8,485,945 B2 | 7/2013 | Leonhard |
| 8,485,982 B2 | 7/2013 | Gavish et al. |
| 8,485,996 B2 | 7/2013 | Bluman |
| 8,487,759 B2 | 7/2013 | Hill |
| 8,491,446 B2 | 7/2013 | BlumanHinds et al. |
| 8,491,572 B2 | 7/2013 | Martinson et al. |
| 8,493,822 B2 | 7/2013 | Lee et al. |
| 8,503,086 B2 | 8/2013 | French et al. |
| 8,505,597 B2 | 8/2013 | Sharperson |
| 8,506,370 B2 | 8/2013 | Homsi |
| 8,506,457 B2 | 8/2013 | Baudhuin |
| 8,506,458 B2 | 8/2013 | Dugan |
| 8,512,210 B2 | 8/2013 | Shauli |
| 8,515,930 B2 | 8/2013 | Hong |
| 8,516,723 B2 | 8/2013 | Ferrigan et al. |
| 8,517,896 B2 | 8/2013 | Robinette et al. |
| 8,517,899 B2 | 8/2013 | Zhou |
| 8,523,789 B2 | 9/2013 | Keiser |
| 8,527,038 B2 | 9/2013 | Moon et al. |
| 8,529,409 B1 | 9/2013 | Lesea-Ames |
| 8,531,386 B1 | 9/2013 | Kerr et al. |
| 8,533,007 B2 | 9/2013 | Egami et al. |
| 8,533,620 B2 | 9/2013 | Hoffman et al. |
| 8,535,247 B2 | 9/2013 | Williams |
| 8,538,333 B2 | 9/2013 | Jain et al. |
| 8,538,723 B2 | 9/2013 | Chang |
| 8,540,560 B2 | 9/2013 | Crowley et al. |
| 8,540,641 B2 | 9/2013 | Kroll et al. |
| 8,543,185 B2 | 9/2013 | Yuen et al. |
| 8,545,417 B2 | 10/2013 | Banet et al. |
| 8,550,962 B2 | 10/2013 | Piaget et al. |
| 8,554,214 B2 | 10/2013 | Sweeney et al. |
| 8,554,802 B1 | 10/2013 | Barden et al. |
| 8,556,778 B1 | 10/2013 | Dugan |
| 8,560,951 B1 | 10/2013 | Snyder et al. |
| 8,562,489 B2 | 10/2013 | Burton et al. |
| 8,568,278 B2 | 10/2013 | Riley et al. |
| 8,571,880 B2 | 10/2013 | Goldberg |
| 8,572,576 B2 | 10/2013 | Elvanoglu et al. |
| 8,573,982 B1 | 11/2013 | Chuang |
| 8,579,767 B2 | 11/2013 | Ellis et al. |
| 8,584,520 B2 | 11/2013 | Kokkoneva et al. |
| 8,591,411 B2 | 11/2013 | Banet et al. |
| 8,594,772 B2 | 11/2013 | Eggenberger et al. |
| RE44,650 E | 12/2013 | Anderson |
| 8,597,093 B2 | 12/2013 | Engelberg et al. |
| 8,602,951 B2 | 12/2013 | Morris |
| 8,602,997 B2 | 12/2013 | Banet et al. |
| 8,605,048 B2 | 12/2013 | Ye et al. |
| 8,608,624 B2 | 12/2013 | Shabodyash et al. |
| 8,610,593 B2 | 12/2013 | Van Acht et al. |
| 8,613,689 B2 | 12/2013 | Dyer et al. |
| 8,614,595 B2 | 12/2013 | Acatrinei |
| 8,614,902 B2 | 12/2013 | Pansier et al. |
| 8,617,008 B2 | 12/2013 | Marty et al. |
| 8,622,873 B2 | 1/2014 | Mcgown |
| 8,628,333 B2 | 1/2014 | Prinzel, III et al. |

(56) References Cited

U.S. PATENT DOCUMENTS

| | | |
|---|---|---|
| 8,628,453 B2 | 1/2014 | Balakrishnan et al. |
| 8,639,020 B1 | 1/2014 | Kutliroff et al. |
| 8,647,240 B2 | 2/2014 | Heidecke |
| 8,649,890 B2 | 2/2014 | Martin |
| 8,652,010 B2 | 2/2014 | Ellis et al. |
| 8,654,198 B2 | 2/2014 | Pryor |
| 8,655,004 B2 | 2/2014 | Prest et al. |
| 8,657,724 B2 | 2/2014 | Yang |
| 8,662,901 B2 | 3/2014 | Tzao et al. |
| 8,663,106 B2 | 3/2014 | Stivoric et al. |
| 8,667,194 B2 | 3/2014 | Dybsetter et al. |
| 8,670,222 B2 | 3/2014 | Rothkopf |
| 8,672,852 B2 | 3/2014 | Gavish |
| 8,676,170 B2 | 3/2014 | Porrati et al. |
| 8,676,541 B2 | 3/2014 | Schrock et al. |
| 8,678,979 B2 | 3/2014 | Stark et al. |
| 8,684,925 B2 | 4/2014 | Manicka et al. |
| 8,690,578 B1 | 4/2014 | Nusbaum et al. |
| 8,690,735 B2 | 4/2014 | Watterson et al. |
| 8,690,738 B1 | 4/2014 | Astilean |
| 8,701,567 B1 | 4/2014 | Esfandiari et al. |
| 8,702,430 B2 | 4/2014 | Dibenedetto et al. |
| 8,702,567 B2 | 4/2014 | Hu |
| 8,704,068 B2 | 4/2014 | Bowen |
| 8,706,530 B2 | 4/2014 | Ohnemus et al. |
| 8,708,842 B2 | 4/2014 | Ganuza |
| 8,708,870 B2 | 4/2014 | Nalley |
| 8,712,510 B2 | 4/2014 | Quy |
| 8,718,752 B2 | 5/2014 | Libbus et al. |
| 8,719,202 B1 | 5/2014 | Maeng |
| 8,727,947 B2 | 5/2014 | Tagliabue |
| 8,734,157 B1 | 5/2014 | Hummel, III |
| 8,734,296 B1 | 5/2014 | Brumback et al. |
| 8,734,301 B2 | 5/2014 | Remelius |
| 8,734,302 B2 | 5/2014 | Hsieh |
| 8,738,732 B2 | 5/2014 | Karidi |
| 8,740,751 B2 | 6/2014 | Shum |
| 8,740,756 B2 | 6/2014 | Shabodyash et al. |
| 8,740,802 B2 | 6/2014 | Banet et al. |
| 8,740,807 B2 | 6/2014 | Banet et al. |
| 8,744,803 B2 | 6/2014 | Park et al. |
| 8,745,104 B1 | 6/2014 | Rosenberg |
| 8,745,496 B2 | 6/2014 | Gilley et al. |
| 8,747,330 B2 | 6/2014 | Banet et al. |
| 8,758,201 B2 | 6/2014 | Ashby et al. |
| 8,762,101 B2 | 6/2014 | Yuen et al. |
| 8,762,167 B2 | 6/2014 | Blander et al. |
| 8,762,313 B2 | 6/2014 | Lahav et al. |
| 8,764,609 B1 | 7/2014 | Elahmadie |
| 8,764,651 B2 | 7/2014 | Tran |
| 8,768,769 B2 | 7/2014 | Foladare et al. |
| 8,770,742 B2 | 7/2014 | Howell et al. |
| 8,771,206 B2 | 7/2014 | Gettelman et al. |
| 8,775,454 B2 | 7/2014 | Geer |
| 8,776,264 B2 | 7/2014 | Kiernan |
| 8,777,815 B2 | 7/2014 | Case, Jr. et al. |
| 8,777,820 B2 | 7/2014 | Lo |
| 8,781,568 B2 | 7/2014 | Dugan |
| 8,783,326 B1 | 7/2014 | Vaninger et al. |
| 8,784,271 B2 | 7/2014 | Brumback et al. |
| 8,784,273 B2 | 7/2014 | Dugan |
| 8,784,274 B1 | 7/2014 | Chuang |
| 8,790,220 B2 | 7/2014 | Karvonen |
| 8,790,222 B2 | 7/2014 | Burger |
| 8,790,259 B2 | 7/2014 | Katra et al. |
| 8,795,138 B1 | 8/2014 | Yeh et al. |
| 8,799,200 B2 | 8/2014 | Lahav |
| 8,801,581 B2 | 8/2014 | Lai et al. |
| 8,805,844 B2 | 8/2014 | Schorzman et al. |
| 8,805,941 B2 | 8/2014 | Barak et al. |
| 8,814,754 B2 | 8/2014 | Weast et al. |
| 8,821,350 B2 | 9/2014 | Maertz |
| 8,821,351 B2 | 9/2014 | Abuelsaad et al. |
| 8,824,697 B2 | 9/2014 | Christoph |
| 8,825,445 B2 | 9/2014 | Hoffman et al. |
| 8,827,870 B2 | 9/2014 | Dyer et al. |
| 8,831,407 B2 | 9/2014 | Meschter et al. |
| 8,831,538 B2 | 9/2014 | Yuen |
| 8,838,471 B1 | 9/2014 | Shum et al. |
| 8,845,497 B2 | 9/2014 | Turner |
| 8,847,988 B2 | 9/2014 | Geisner et al. |
| 8,851,565 B2 | 10/2014 | Hontz et al. |
| 8,861,860 B2 | 10/2014 | Gupta |
| 8,864,587 B2 | 10/2014 | Framel et al. |
| 8,864,627 B2 | 10/2014 | Bayerlein et al. |
| 8,868,448 B2 | 10/2014 | Freishtat et al. |
| 8,870,791 B2 | 10/2014 | Sabatino |
| 8,876,661 B2 | 11/2014 | Lu |
| 8,882,637 B2 | 11/2014 | Ainsworth et al. |
| 8,882,666 B1 | 11/2014 | Goldberg et al. |
| 8,888,583 B2 | 11/2014 | Dugan et al. |
| 8,888,660 B1 | 11/2014 | Oteman |
| 8,888,700 B2 | 11/2014 | Banet et al. |
| 8,894,551 B2 | 11/2014 | Kerdjoudj |
| 8,897,868 B2 | 11/2014 | Mazar et al. |
| 8,900,099 B1 | 12/2014 | Boyette |
| 8,902,714 B2 | 12/2014 | Gossweiler, III et al. |
| 8,903,671 B2 | 12/2014 | Park et al. |
| 8,908,894 B2 | 12/2014 | Amento et al. |
| 8,915,823 B2 | 12/2014 | McKirdy et al. |
| 8,918,465 B2 | 12/2014 | Barak |
| 8,918,543 B2 | 12/2014 | Karstens |
| 8,920,291 B2 | 12/2014 | Chen et al. |
| 8,920,332 B2 | 12/2014 | Hong et al. |
| 8,920,343 B2 | 12/2014 | Sabatino |
| 8,926,475 B2 | 1/2015 | Lin et al. |
| 8,926,479 B2 | 1/2015 | Chen et al. |
| 8,939,831 B2 | 1/2015 | Dugan |
| 8,943,002 B2 | 1/2015 | Zelenko et al. |
| 8,944,958 B1 | 2/2015 | Brumback et al. |
| 8,944,968 B2 | 2/2015 | Baudhuin |
| 8,945,328 B2 | 2/2015 | Longinotti-Buitoni et al. |
| 8,947,226 B2 | 2/2015 | Dugan |
| 8,951,106 B2 | 2/2015 | Crowley |
| 8,951,164 B2 | 2/2015 | Morris et al. |
| 8,951,168 B2 | 2/2015 | Baudhuin |
| 8,954,135 B2 | 2/2015 | Yuen et al. |
| 8,954,290 B2 | 2/2015 | Yuen et al. |
| 8,956,268 B2 | 2/2015 | Huang et al. |
| 8,956,290 B2 | 2/2015 | Gilley et al. |
| 8,956,303 B2 | 2/2015 | Hong et al. |
| 8,956,715 B2 | 2/2015 | Kim |
| 8,958,631 B2 | 2/2015 | Kutliroff et al. |
| 8,961,371 B2 | 2/2015 | Sultan et al. |
| 8,961,413 B2 | 2/2015 | Teller et al. |
| 8,961,414 B2 | 2/2015 | Teller et al. |
| 8,965,348 B1 | 2/2015 | Cronin |
| 8,965,498 B2 | 2/2015 | Katra et al. |
| 8,965,541 B2 | 2/2015 | Martinez et al. |
| 8,965,732 B2 | 2/2015 | Robinette et al. |
| 8,968,161 B2 | 3/2015 | Shapiro et al. |
| 8,968,163 B1 | 3/2015 | Vidmar |
| 8,972,199 B2 | 3/2015 | Liang |
| 8,976,007 B2 | 3/2015 | Dugan |
| 8,977,194 B2 | 3/2015 | Jain et al. |
| 8,979,709 B2 | 3/2015 | Toback et al. |
| 8,979,765 B2 | 3/2015 | Banet et al. |
| 8,986,165 B2 | 3/2015 | Ashby |
| 8,992,383 B2 | 3/2015 | Bilang |
| 8,992,387 B2 | 3/2015 | Watterson et al. |
| 9,005,085 B2 | 4/2015 | Astilean |
| 9,005,129 B2 | 4/2015 | Venkatraman et al. |
| 9,011,291 B2 | 4/2015 | Birrell |
| 9,011,292 B2 | 4/2015 | Weast et al. |
| 9,011,293 B2 | 4/2015 | Shavit et al. |
| 9,011,301 B2 | 4/2015 | Balandis et al. |
| 9,015,952 B2 | 4/2015 | Magosaki |
| 9,017,230 B1 | 4/2015 | Pitts |
| 9,026,927 B2 | 5/2015 | Brumback et al. |
| 9,028,368 B2 | 5/2015 | Ashby et al. |
| 9,028,441 B2 | 5/2015 | Kuhn |
| 9,031,812 B2 | 5/2015 | Roberts et al. |
| 9,037,578 B2 | 5/2015 | Brust et al. |
| 9,038,218 B1 | 5/2015 | Heil et al. |

(56) References Cited

U.S. PATENT DOCUMENTS

| | | |
|---|---|---|
| 9,039,578 B2 | 5/2015 | Dalebout |
| 9,039,581 B2 | 5/2015 | Chia et al. |
| 9,039,614 B2 | 5/2015 | Yuen et al. |
| 9,042,596 B2 | 5/2015 | Connor |
| 9,050,491 B2 | 6/2015 | Gordon et al. |
| 9,050,498 B2 | 6/2015 | Lu et al. |
| 9,052,798 B1 | 6/2015 | Klassen et al. |
| 9,055,868 B2 | 6/2015 | Islam |
| 9,064,342 B2 | 6/2015 | Yuen et al. |
| 9,069,380 B2 | 6/2015 | Rahman et al. |
| 9,072,930 B2 | 7/2015 | Ashby et al. |
| 9,072,932 B2 | 7/2015 | Piaget et al. |
| 9,083,826 B2 | 7/2015 | Lu et al. |
| 9,084,912 B2 | 7/2015 | Jaquish et al. |
| 9,089,732 B2 | 7/2015 | Andon et al. |
| 9,089,733 B2 | 7/2015 | Fisbein et al. |
| 9,095,740 B2 | 8/2015 | Wu |
| 9,107,586 B2 | 8/2015 | Tran |
| 9,108,079 B2 | 8/2015 | Solow et al. |
| 9,114,275 B2 | 8/2015 | Lu et al. |
| 9,114,276 B2 | 8/2015 | Bayerlein et al. |
| 9,119,983 B2 | 9/2015 | Rhea |
| 9,123,317 B2 | 9/2015 | Watterson et al. |
| 9,123,380 B2 | 9/2015 | Holtz et al. |
| 9,128,981 B1 | 9/2015 | Geer |
| 9,132,051 B2 | 9/2015 | Heil |
| 9,135,347 B2 | 9/2015 | Damman et al. |
| 9,137,309 B2 | 9/2015 | Ananny et al. |
| 9,138,614 B2 | 9/2015 | Lu et al. |
| 9,138,615 B2 | 9/2015 | Olson et al. |
| 9,141,087 B2 | 9/2015 | Brown et al. |
| 9,143,881 B2 | 9/2015 | Fan et al. |
| 9,144,703 B2 | 9/2015 | Dalebout et al. |
| 9,144,709 B2 | 9/2015 | Reich |
| 9,146,147 B1 | 9/2015 | Bakhsh |
| 9,162,102 B1 | 10/2015 | Eder et al. |
| 9,162,106 B1 | 10/2015 | Scheiman |
| 9,162,142 B2 | 10/2015 | Shum et al. |
| 9,168,001 B2 | 10/2015 | Stivoric et al. |
| 9,168,414 B2 | 10/2015 | Liu et al. |
| 9,173,593 B2 | 11/2015 | Banet et al. |
| 9,173,594 B2 | 11/2015 | Banet et al. |
| 9,174,084 B2 | 11/2015 | Morris et al. |
| 9,174,085 B2 | 11/2015 | Foley |
| 9,178,635 B2 | 11/2015 | Ben-Shlomo |
| 9,183,498 B2 | 11/2015 | Landers |
| 9,186,537 B2 | 11/2015 | Arnold et al. |
| 9,186,549 B2 | 11/2015 | Watterson et al. |
| 9,186,552 B1 | 11/2015 | Deal |
| 9,189,021 B2 | 11/2015 | Jerauld |
| 9,192,800 B1 | 11/2015 | Meyer et al. |
| 9,192,816 B2 | 11/2015 | Molyneux et al. |
| 9,199,115 B2 | 12/2015 | Yim et al. |
| 9,199,123 B2 | 12/2015 | Solow |
| 9,201,405 B2 | 12/2015 | Clarkson et al. |
| 9,201,458 B2 | 12/2015 | Hunt et al. |
| 9,205,301 B2 | 12/2015 | Cohen |
| 9,208,764 B2 | 12/2015 | Ghosh et al. |
| 9,211,440 B2 | 12/2015 | Lagree |
| 9,213,803 B2 | 12/2015 | Rolley |
| 9,220,940 B2 | 12/2015 | Al Kuwari |
| 9,221,545 B2 | 12/2015 | Popescu et al. |
| 9,223,936 B2 | 12/2015 | Aragones et al. |
| 9,224,291 B2 | 12/2015 | Moll-Carrillo et al. |
| 9,226,692 B2 | 1/2016 | Haas |
| 9,229,476 B2 | 1/2016 | Yanev et al. |
| 9,230,064 B2 | 1/2016 | Yanev et al. |
| 9,233,269 B2 | 1/2016 | Lannon |
| 9,241,635 B2 | 1/2016 | Yuen et al. |
| 9,245,428 B2 | 1/2016 | Weddle et al. |
| 9,247,543 B2 | 1/2016 | Berlin et al. |
| 9,253,168 B2 | 2/2016 | Panther |
| 9,254,099 B2 | 2/2016 | Connor |
| 9,256,910 B2 | 2/2016 | Goldberg |
| 9,257,054 B2 | 2/2016 | Coza et al. |
| 9,258,670 B2 | 2/2016 | Goyal et al. |
| 9,259,633 B2 | 2/2016 | Meyers |
| 9,262,064 B2 | 2/2016 | Yanev et al. |
| 9,269,119 B2 | 2/2016 | Warner |
| 9,272,183 B2 | 3/2016 | Quy |
| 9,272,186 B2 | 3/2016 | Reich |
| 9,275,617 B2 | 3/2016 | Regnier |
| 9,279,734 B2 | 3/2016 | Walker |
| 9,283,429 B2 | 3/2016 | Aragones et al. |
| 9,288,298 B2 | 3/2016 | Choudhary et al. |
| 9,289,063 B2 | 3/2016 | Baugh et al. |
| 9,295,422 B2 | 3/2016 | Tai |
| 9,295,894 B2 | 3/2016 | Papadopolous |
| 9,305,141 B2 | 4/2016 | Fabrizio |
| 9,308,415 B2 | 4/2016 | Crawford et al. |
| 9,311,802 B1 | 4/2016 | Chin et al. |
| 9,317,662 B2 | 4/2016 | Bangera et al. |
| 9,318,030 B2 | 4/2016 | Harris et al. |
| 9,329,053 B2 | 5/2016 | Lakovic et al. |
| 9,332,363 B2 | 5/2016 | Jain et al. |
| 9,333,388 B2 | 5/2016 | Lee et al. |
| 9,339,209 B2 | 5/2016 | Banet et al. |
| 9,339,681 B1 | 5/2016 | Nalley |
| 9,339,683 B2 | 5/2016 | Dilli et al. |
| 9,339,691 B2 | 5/2016 | Brammer |
| 9,339,692 B2 | 5/2016 | Hashish |
| 9,345,947 B2 | 5/2016 | Harris et al. |
| 9,349,280 B2 | 5/2016 | Baldwin et al. |
| 9,350,598 B2 | 5/2016 | Barak et al. |
| 9,352,185 B2 | 5/2016 | Hendrickson et al. |
| 9,352,186 B2 | 5/2016 | Watterson |
| 9,352,187 B2 | 5/2016 | Piaget et al. |
| 9,357,551 B2 | 5/2016 | Gutman |
| 9,357,921 B2 | 6/2016 | Chang et al. |
| 9,358,422 B2 | 6/2016 | Brontman |
| 9,358,426 B2 | 6/2016 | Aragones et al. |
| 9,364,158 B2 | 6/2016 | Banet et al. |
| 9,364,706 B2 | 6/2016 | Lo |
| 9,364,708 B2 | 6/2016 | Luger et al. |
| 9,364,714 B2 | 6/2016 | Koduri et al. |
| 9,367,668 B2 | 6/2016 | Flynt et al. |
| 9,370,679 B2 | 6/2016 | Lagree et al. |
| 9,370,687 B2 | 6/2016 | Hao |
| 9,374,279 B2 | 6/2016 | Yuen et al. |
| 9,375,629 B2 | 6/2016 | Schieffer et al. |
| 9,377,314 B2 | 6/2016 | Tseng et al. |
| 9,378,336 B2 | 6/2016 | Ohnemus et al. |
| 9,381,420 B2 | 7/2016 | Burroughs |
| 9,381,445 B2 | 7/2016 | Ventura et al. |
| 9,385,810 B2 | 7/2016 | Hazani |
| 9,387,387 B2 | 7/2016 | Dalebout |
| 9,389,057 B2 | 7/2016 | Meschter et al. |
| 9,389,718 B1 | 7/2016 | Letourneur |
| 9,389,754 B2 | 7/2016 | Reese et al. |
| 9,390,229 B1 | 7/2016 | Kahn et al. |
| 9,392,941 B2 | 7/2016 | Powch et al. |
| 9,395,754 B2 | 7/2016 | Cronin |
| 9,401,078 B2 | 7/2016 | Barrett |
| 9,403,048 B2 | 8/2016 | Balandis et al. |
| 9,403,053 B2 | 8/2016 | Kaiser et al. |
| 9,405,892 B2 | 8/2016 | Baldwin et al. |
| 9,409,050 B2 | 8/2016 | Mintz |
| 9,409,052 B2 | 8/2016 | Werner |
| 9,411,936 B2 | 8/2016 | Landrum et al. |
| 9,411,940 B2 | 8/2016 | Burroughs et al. |
| 9,415,257 B2 | 8/2016 | Habing |
| 9,420,083 B2 | 8/2016 | Roberts et al. |
| 9,420,542 B2 | 8/2016 | Henia |
| 9,421,422 B2 | 8/2016 | Yuen et al. |
| 9,421,448 B2 | 8/2016 | Tropper et al. |
| 9,422,018 B2 | 8/2016 | Pelot et al. |
| 9,430,043 B1 | 8/2016 | Amento et al. |
| 9,430,920 B2 | 8/2016 | Munro et al. |
| 9,439,574 B2 | 9/2016 | McCombie et al. |
| 9,440,134 B2 | 9/2016 | Nicora |
| 9,442,100 B2 | 9/2016 | Connor |
| 9,446,288 B1 | 9/2016 | Pazan |
| 9,451,897 B2 | 9/2016 | Mazar et al. |
| 9,452,315 B1 | 9/2016 | Murray et al. |

(56) References Cited

U.S. PATENT DOCUMENTS

| | | |
|---|---|---|
| 9,452,320 B2 | 9/2016 | Yang |
| 9,455,784 B2 | 9/2016 | Cune et al. |
| 9,457,224 B2 | 10/2016 | Giannelli et al. |
| 9,457,256 B2 | 10/2016 | Aragones et al. |
| 9,460,421 B2 | 10/2016 | Lai et al. |
| 9,462,844 B2 | 10/2016 | Schrock et al. |
| 9,463,349 B1 | 10/2016 | Chang |
| 9,463,572 B2 | 10/2016 | Parente |
| 9,468,382 B2 | 10/2016 | Hanoun |
| 9,468,793 B2 | 10/2016 | Salmon |
| 9,468,794 B2 | 10/2016 | Barton |
| 9,473,593 B2 | 10/2016 | Wallace |
| 9,474,925 B1 | 10/2016 | Hsiung |
| 9,474,935 B2 | 10/2016 | Abbondanza et al. |
| 9,477,303 B2 | 10/2016 | Fleischmann et al. |
| 9,480,874 B2 | 11/2016 | Cutler |
| 9,486,070 B2 | 11/2016 | Labrosse et al. |
| 9,486,382 B1 | 11/2016 | Boss |
| 9,486,658 B2 | 11/2016 | Alexander |
| 9,491,562 B2 | 11/2016 | Cronin |
| 9,495,015 B1 | 11/2016 | Kahn et al. |
| 9,495,860 B2 | 11/2016 | Lett |
| 9,498,066 B2 | 11/2016 | Christianson et al. |
| 9,498,671 B1 | 11/2016 | Softky |
| 9,498,704 B1 | 11/2016 | Cohen et al. |
| 9,500,464 B2 | 11/2016 | Coza |
| 9,504,414 B2 | 11/2016 | Coza et al. |
| 9,505,241 B2 | 11/2016 | Lyon |
| 9,509,269 B1 | 11/2016 | Rosenberg |
| 9,511,259 B2 | 12/2016 | Mountain |
| 9,517,378 B2 | 12/2016 | Ashby et al. |
| 9,517,406 B2 | 12/2016 | Shum et al. |
| 9,529,385 B2 | 12/2016 | Connor |
| 9,529,437 B2 | 12/2016 | Kahn et al. |
| 9,532,002 B2 | 12/2016 | Glass et al. |
| 9,532,734 B2 | 1/2017 | Hoffman et al. |
| 9,533,228 B2 | 1/2017 | Dugan |
| 9,535,505 B2 | 1/2017 | Erkkila et al. |
| 9,536,449 B2 | 1/2017 | Connor |
| 9,539,458 B1 | 1/2017 | Ross |
| 9,540,071 B2 | 1/2017 | Jordan et al. |
| 9,540,174 B2 | 1/2017 | Josserond et al. |
| 9,545,535 B2 | 1/2017 | Lagree |
| 9,545,541 B2 | 1/2017 | Aragones et al. |
| 9,549,585 B2 | 1/2017 | Amos et al. |
| 9,560,917 B2 | 2/2017 | Roslund, Jr. |
| 9,563,336 B2 | 2/2017 | Barak et al. |
| 9,563,700 B2 | 2/2017 | Garmark et al. |
| 9,573,017 B2 | 2/2017 | Chang |
| 9,579,534 B2 | 2/2017 | Sutkowski et al. |
| 9,579,544 B2 | 2/2017 | Watterson |
| 9,582,071 B2 | 2/2017 | Baldwin et al. |
| 9,582,976 B2 | 2/2017 | Chin et al. |
| 9,585,563 B2 | 3/2017 | Mensinger et al. |
| 9,586,090 B2 | 3/2017 | Watterson et al. |
| 9,589,482 B2 | 3/2017 | Baldwin et al. |
| 9,594,433 B2 | 3/2017 | Baldwin et al. |
| 9,597,540 B2 | 3/2017 | Arnold |
| 9,599,981 B2 | 3/2017 | Crabtree |
| 9,600,079 B2 | 3/2017 | Baldwin et al. |
| 9,602,210 B2 | 3/2017 | Berlin et al. |
| 9,604,096 B2 | 3/2017 | Arnold et al. |
| 9,604,099 B2 | 3/2017 | Taylor |
| 9,610,475 B1 | 4/2017 | DeKnock et al. |
| 9,610,506 B2 | 4/2017 | Dugan |
| 9,615,215 B2 | 4/2017 | Yuen et al. |
| 9,615,785 B2 | 4/2017 | Rocker et al. |
| 9,616,281 B2 | 4/2017 | Hsiung |
| 9,621,959 B2 | 4/2017 | Mountain |
| 9,622,537 B2 | 4/2017 | Amos et al. |
| 9,623,286 B1 | 4/2017 | Chen |
| 9,628,286 B1 | 4/2017 | Nguyen et al. |
| 9,632,746 B2 | 4/2017 | Keipert et al. |
| 9,636,543 B2 | 5/2017 | Dyer et al. |
| 9,636,567 B2 | 5/2017 | Brammer et al. |
| 9,642,764 B2 | 5/2017 | Kuehne et al. |
| 9,646,137 B2 | 5/2017 | Gilley et al. |
| 9,646,481 B2 | 5/2017 | Messenger et al. |
| 9,647,758 B2 | 5/2017 | Hazani |
| 9,655,053 B2 | 5/2017 | Park et al. |
| 9,658,066 B2 | 5/2017 | Yuen et al. |
| 9,661,355 B2 | 5/2017 | Ho |
| 9,661,781 B2 | 5/2017 | Anolik et al. |
| 9,669,261 B2 | 6/2017 | Eder |
| 9,672,196 B2 | 6/2017 | Shachar et al. |
| 9,672,754 B2 | 6/2017 | Yuen et al. |
| 9,673,904 B2 | 6/2017 | Palanisamy et al. |
| 9,678,626 B2 | 6/2017 | Whang |
| 9,681,313 B2 | 6/2017 | Malach |
| 9,682,306 B2 | 6/2017 | Lin et al. |
| 9,687,689 B2 | 6/2017 | Lin |
| 9,692,844 B2 | 6/2017 | Messenger et al. |
| RE46,481 E | 7/2017 | Sako et al. |
| 9,694,234 B2 | 7/2017 | Dalebout et al. |
| 9,694,247 B2 | 7/2017 | Nurnberg |
| 9,697,740 B2 | 7/2017 | Zhang et al. |
| 9,700,780 B2 | 7/2017 | Riley et al. |
| 9,700,802 B2 | 7/2017 | Dugan |
| 9,701,530 B2 | 7/2017 | Kline |
| 9,707,441 B2 | 7/2017 | Yang |
| 9,707,447 B1 | 7/2017 | Lopez Babodilla |
| 9,710,711 B2 | 7/2017 | Dibenedetto et al. |
| 9,712,629 B2 | 7/2017 | Molettiere et al. |
| 9,713,739 B2 | 7/2017 | Dalmia |
| 9,715,774 B2 | 7/2017 | Baldwin et al. |
| 9,719,797 B2 | 8/2017 | Fino et al. |
| 9,720,443 B2 | 8/2017 | Malhotra |
| 9,723,393 B2 | 8/2017 | Nguyen et al. |
| 9,724,563 B2 | 8/2017 | Schmidt |
| 9,724,589 B2 | 8/2017 | Baudhuin |
| 9,728,059 B2 | 8/2017 | Arnold et al. |
| 9,729,921 B2 | 8/2017 | Kim et al. |
| 9,729,989 B2 | 8/2017 | Marten |
| 9,730,025 B2 | 8/2017 | Yuen et al. |
| 9,730,228 B2 | 8/2017 | Harel |
| 9,730,619 B2 | 8/2017 | Messenger et al. |
| 9,731,158 B1 | 8/2017 | Lo |
| 9,734,184 B1 | 8/2017 | Lagace et al. |
| 9,737,261 B2 | 8/2017 | Coza et al. |
| 9,737,747 B1 | 8/2017 | Walsh et al. |
| 9,743,861 B2 | 8/2017 | Giedwoyn et al. |
| 9,756,895 B2 | 9/2017 | Rice et al. |
| 9,757,605 B2 | 9/2017 | Olson et al. |
| 9,757,611 B1 | 9/2017 | Colburn |
| 9,763,581 B2 | 9/2017 | Bonutti et al. |
| 9,764,184 B2 | 9/2017 | Kueker et al. |
| 9,767,212 B2 | 9/2017 | Lavi et al. |
| 9,769,522 B2 | 9/2017 | Richardson |
| 9,772,612 B2 | 9/2017 | McCarthy, III et al. |
| 9,775,123 B2 | 9/2017 | Harel |
| 9,776,039 B1 | 10/2017 | Xu |
| 9,776,042 B2 | 10/2017 | Prokhorov |
| 9,778,280 B2 | 10/2017 | Yuen et al. |
| 9,782,125 B2 | 10/2017 | Berner, Jr. et al. |
| 9,782,625 B1 | 10/2017 | Blum et al. |
| 9,789,362 B1 | 10/2017 | Su et al. |
| 9,792,361 B1 | 10/2017 | Geer |
| 9,795,827 B2 | 10/2017 | Wiener et al. |
| 9,795,828 B2 | 10/2017 | Andrade |
| 9,797,920 B2 | 10/2017 | Kahn et al. |
| 9,798,309 B2 | 10/2017 | Tirpak |
| 9,801,547 B2 | 10/2017 | Yuen et al. |
| 9,802,081 B2 | 10/2017 | Ridgel et al. |
| 9,808,202 B2 | 11/2017 | Wu et al. |
| 9,808,673 B2 | 11/2017 | Robinson |
| 9,811,639 B2 | 11/2017 | Aragones et al. |
| 9,814,920 B1 | 11/2017 | Monterrey |
| 9,814,927 B2 | 11/2017 | Forystek |
| 9,814,928 B2 | 11/2017 | Taylor |
| 9,814,929 B2 | 11/2017 | Moser |
| 9,814,930 B2 | 11/2017 | Manzke et al. |
| 9,818,285 B2 | 11/2017 | Clarke et al. |
| 9,819,561 B2 | 11/2017 | Freishtat et al. |
| 9,819,754 B2 | 11/2017 | Park et al. |

(56) References Cited

U.S. PATENT DOCUMENTS

| | | |
|---|---|---|
| 9,821,191 B2 | 11/2017 | Abbondanza |
| 9,821,212 B2 | 11/2017 | Kolman et al. |
| 9,824,110 B2 | 11/2017 | Giudici et al. |
| 9,824,578 B2 | 11/2017 | Burton et al. |
| 9,827,458 B2 | 11/2017 | Dalton |
| 9,829,068 B2 | 11/2017 | Marchetti |
| 9,829,327 B2 | 11/2017 | Nagy et al. |
| 9,833,141 B2 | 12/2017 | Kampman et al. |
| 9,833,658 B2 | 12/2017 | Wiener et al. |
| 9,838,736 B2 | 12/2017 | Smith et al. |
| 9,841,077 B2 | 12/2017 | Modrezejewski et al. |
| 9,849,330 B2 | 12/2017 | Lagree |
| 9,849,333 B2 | 12/2017 | Fung |
| 9,849,361 B2 | 12/2017 | Coza et al. |
| 9,852,271 B2 | 12/2017 | Aragones et al. |
| 9,858,307 B2 | 1/2018 | Sultan et al. |
| 9,861,300 B2 | 1/2018 | Gettelman et al. |
| 9,864,844 B2 | 1/2018 | Durham et al. |
| 9,866,596 B2 | 1/2018 | Das et al. |
| 9,880,805 B1 | 1/2018 | Guralnick |
| 9,881,326 B2 | 1/2018 | Gilley et al. |
| 9,882,736 B2 | 1/2018 | Lett |
| 9,882,992 B2 | 1/2018 | Baldwin et al. |
| 9,886,309 B2 | 2/2018 | Alles et al. |
| 9,886,871 B1 | 2/2018 | Rauhala et al. |
| 9,889,334 B2 | 2/2018 | Ashby et al. |
| 9,892,417 B2 | 2/2018 | Shachar et al. |
| 9,901,767 B2 | 2/2018 | Kuo |
| 9,901,772 B2 | 2/2018 | Crowley et al. |
| 9,901,780 B2 | 2/2018 | DeLuca et al. |
| 9,901,805 B2 | 2/2018 | Hughes, Jr. |
| 9,906,572 B2 | 2/2018 | Wang et al. |
| 9,907,396 B1 | 3/2018 | Labrosse et al. |
| 9,910,498 B2 | 3/2018 | Kutliroff et al. |
| 9,914,003 B2 | 3/2018 | Kuehne et al. |
| 9,914,011 B2 | 3/2018 | Downey et al. |
| 9,914,014 B2 | 3/2018 | Lagree et al. |
| 9,919,198 B2 | 3/2018 | Romeo et al. |
| 9,921,726 B1 | 3/2018 | Sculley et al. |
| 9,937,375 B2 | 4/2018 | Zhu |
| 9,940,161 B1 | 4/2018 | Kahn et al. |
| 9,940,682 B2 | 4/2018 | Hoffman et al. |
| 9,943,159 B1 | 4/2018 | Novikova |
| 9,943,719 B2 | 4/2018 | Smith et al. |
| 9,943,722 B2 | 4/2018 | Dalebout |
| 9,946,857 B2 | 4/2018 | Beals |
| 9,948,349 B2 | 4/2018 | Malach |
| 9,948,477 B2 | 4/2018 | Marten |
| 9,950,209 B2 | 4/2018 | Yim et al. |
| 9,956,450 B2 | 5/2018 | Bayerlein et al. |
| 9,959,902 B2 | 5/2018 | McNamee |
| 9,960,980 B2 | 5/2018 | Wilson |
| 9,962,081 B2 | 5/2018 | Mensinger et al. |
| 9,962,305 B2 | 5/2018 | Yamada et al. |
| 9,962,576 B2 | 5/2018 | Anderson |
| 9,965,059 B2 | 5/2018 | Myers et al. |
| 9,967,614 B2 | 5/2018 | McCarthy, III |
| 9,968,821 B2 | 5/2018 | Finlayson et al. |
| 9,968,823 B2 | 5/2018 | Cutler |
| 9,974,997 B2 | 5/2018 | Cei |
| 9,977,874 B2 | 5/2018 | Aragones et al. |
| 9,983,011 B2 | 5/2018 | Mountain |
| 9,986,315 B2 | 5/2018 | Oleson et al. |
| 9,987,513 B2 | 6/2018 | Yim et al. |
| 9,987,517 B1 | 6/2018 | Kuo |
| 9,989,507 B2 | 6/2018 | Benn |
| 9,993,680 B2 | 6/2018 | Gordon |
| 9,996,066 B2 | 6/2018 | Beals |
| 10,004,656 B2 | 6/2018 | Whalen et al. |
| 10,004,940 B2 | 6/2018 | Badarneh |
| 10,008,090 B2 | 6/2018 | Yuen et al. |
| 10,013,986 B1 | 7/2018 | Bhaya et al. |
| 10,015,216 B2 | 7/2018 | Wang et al. |
| 10,016,655 B2 | 7/2018 | Lagree |
| 10,021,188 B2 | 7/2018 | Oleson et al. |
| 10,022,589 B2 | 7/2018 | Case, Jr. et al. |
| 10,022,590 B2 | 7/2018 | Foley et al. |
| 10,029,172 B2 | 7/2018 | Galasso et al. |
| 10,035,010 B1 | 7/2018 | Wagstaff |
| 10,037,053 B2 | 7/2018 | Malhotra |
| 10,038,952 B2 | 7/2018 | Labrosse et al. |
| 2001/0001303 A1 | 5/2001 | Ohsuga et al. |
| 2001/0008053 A1 | 7/2001 | Belli |
| 2001/0024998 A1 | 9/2001 | Novak |
| 2001/0027266 A1 | 10/2001 | Hautala |
| 2001/0028350 A1 | 10/2001 | Matsuoka et al. |
| 2001/0049320 A1 | 12/2001 | Cohen |
| 2001/0049470 A1 | 12/2001 | Mault et al. |
| 2001/0051564 A1 | 12/2001 | Iund |
| 2001/0053883 A1 | 12/2001 | Yoshimura et al. |
| 2002/0004439 A1 | 1/2002 | Galbraith et al. |
| 2002/0013717 A1 | 1/2002 | Ando |
| 2002/0016235 A1 | 2/2002 | Ashby et al. |
| 2002/0019298 A1 | 2/2002 | Eschenbach |
| 2002/0022551 A1 | 2/2002 | Watterson et al. |
| 2002/0022555 A1 | 2/2002 | Nesci |
| 2002/0024521 A1 | 2/2002 | Goden |
| 2002/0025888 A1 | 2/2002 | Germanton |
| 2002/0026130 A1 | 2/2002 | West |
| 2002/0026292 A1 | 2/2002 | Isami |
| 2002/0031756 A1 | 3/2002 | Holtz |
| 2002/0039952 A1 | 4/2002 | Clem |
| 2002/0042328 A1 | 4/2002 | Yoo |
| 2002/0042912 A1 | 4/2002 | Iijima |
| 2002/0043909 A1 | 4/2002 | Nielsen |
| 2002/0045519 A1 | 4/2002 | Watterson |
| 2002/0047867 A1 | 4/2002 | Mault |
| 2002/0054244 A1 | 5/2002 | Holtz |
| 2002/0055418 A1 | 5/2002 | Pyles et al. |
| 2002/0055419 A1 | 5/2002 | Hinnebusch |
| 2002/0055420 A1 | 5/2002 | Stearns et al. |
| 2002/0055422 A1 | 5/2002 | Airmet |
| 2002/0055857 A1 | 5/2002 | Mault |
| 2002/0060335 A1 | 5/2002 | Edgar |
| 2002/0062236 A1 | 5/2002 | Murashita |
| 2002/0066735 A1 | 6/2002 | Hewlitt et al. |
| 2002/0068887 A1 | 6/2002 | Kikumoto |
| 2002/0068991 A1 | 6/2002 | Fitzsimmons, Jr. |
| 2002/0070954 A1 | 6/2002 | Lang |
| 2002/0077219 A1 | 6/2002 | Cohen |
| 2002/0077221 A1 | 6/2002 | Dalebout et al. |
| 2002/0083122 A1 | 6/2002 | Lemchen |
| 2002/0086779 A1 | 7/2002 | Wilkinson |
| 2002/0088337 A1 | 7/2002 | Devecka |
| 2002/0091043 A1 | 7/2002 | Rexach |
| 2002/0091796 A1 | 7/2002 | Higginson |
| 2002/0094914 A1 | 7/2002 | Maresh et al. |
| 2002/0106617 A1 | 8/2002 | Hersh |
| 2002/0107058 A1 | 8/2002 | Namba et al. |
| 2002/0109710 A1 | 8/2002 | Holtz et al. |
| 2002/0111541 A1 | 8/2002 | Bibl et al. |
| 2002/0116266 A1 | 8/2002 | Marshall |
| 2002/0128119 A1 | 9/2002 | Arai |
| 2002/0128127 A1 | 9/2002 | Chen |
| 2002/0138023 A1 | 9/2002 | Kume et al. |
| 2002/0142887 A1 | 10/2002 | O'Malley |
| 2002/0147078 A1 | 10/2002 | Wu |
| 2002/0151413 A1 | 10/2002 | Dalebout |
| 2002/0155416 A1 | 10/2002 | Barton |
| 2002/0156351 A1 | 10/2002 | Sagel |
| 2002/0156387 A1 | 10/2002 | Dardik |
| 2002/0160883 A1 | 10/2002 | Dugan |
| 2002/0164929 A1 | 11/2002 | Pinson |
| 2002/0169634 A1 | 11/2002 | Nishi |
| 2002/0171070 A1 | 11/2002 | Shim |
| 2002/0173407 A1 | 11/2002 | Bowman |
| 2002/0194604 A1 | 12/2002 | Sanchez et al. |
| 2002/0198084 A1 | 12/2002 | Stearns et al. |
| 2002/0198776 A1 | 12/2002 | Nara |
| 2003/0004424 A1 | 1/2003 | Birnbaum |
| 2003/0013072 A1 | 1/2003 | Thomas |
| 2003/0021273 A1 | 1/2003 | Fouquet |
| 2003/0032524 A1 | 2/2003 | Lamar et al. |
| 2003/0032535 A1 | 2/2003 | Wang |

(56) References Cited

U.S. PATENT DOCUMENTS

| | | |
|---|---|---|
| 2003/0033600 A1 | 2/2003 | Cliff et al. |
| 2003/0040348 A1 | 2/2003 | Martens |
| 2003/0041076 A1 | 2/2003 | Lucovsky |
| 2003/0043986 A1 | 3/2003 | Creamer et al. |
| 2003/0043989 A1 | 3/2003 | Creamer et al. |
| 2003/0044021 A1 | 3/2003 | Wilkinson |
| 2003/0045406 A1 | 3/2003 | Stone |
| 2003/0060331 A1 | 3/2003 | Polk |
| 2003/0060344 A1 | 3/2003 | David |
| 2003/0063133 A1 | 4/2003 | Foote et al. |
| 2003/0065561 A1 | 4/2003 | Brown et al. |
| 2003/0069108 A1 | 4/2003 | Rubinstein |
| 2003/0073545 A1 | 4/2003 | Liu |
| 2003/0074985 A1 | 4/2003 | Liao |
| 2003/0088196 A1 | 5/2003 | Steve |
| 2003/0092532 A1 | 5/2003 | Giannelli et al. |
| 2003/0092540 A1 | 5/2003 | Gillen |
| 2003/0092542 A1 | 5/2003 | Bartholomew et al. |
| 2003/0096675 A1 | 5/2003 | Wang |
| 2003/0100406 A1 | 5/2003 | Millington |
| 2003/0104907 A1 | 6/2003 | Sankrithi |
| 2003/0104908 A1 | 6/2003 | Tung |
| 2003/0105390 A1 | 6/2003 | Alessandri |
| 2003/0115157 A1 | 6/2003 | Circenis |
| 2003/0119635 A1 | 6/2003 | Arbuckle |
| 2003/0125165 A1 | 7/2003 | Trevino |
| 2003/0126593 A1 | 7/2003 | Mault |
| 2003/0128186 A1 | 7/2003 | Laker |
| 2003/0134718 A1 | 7/2003 | Kim |
| 2003/0138761 A1 | 7/2003 | Pesnell |
| 2003/0139254 A1 | 7/2003 | Chang |
| 2003/0142951 A1 | 7/2003 | Tsurugai |
| 2003/0148853 A1 | 8/2003 | Alessandri |
| 2003/0148857 A1 | 8/2003 | Yu |
| 2003/0149344 A1 | 8/2003 | Nizan |
| 2003/0153434 A1 | 8/2003 | Dalebout |
| 2003/0153436 A1 | 8/2003 | Ho |
| 2003/0158014 A1 | 8/2003 | Valentin-Sivico |
| 2003/0163287 A1 | 8/2003 | Vock et al. |
| 2003/0165802 A1 | 9/2003 | Murphy |
| 2003/0166434 A1 | 9/2003 | Lopez-Santillana et al. |
| 2003/0171189 A1 | 9/2003 | Kaufman |
| 2003/0171190 A1 | 9/2003 | Rice |
| 2003/0171192 A1 | 9/2003 | Wu |
| 2003/0176815 A1 | 9/2003 | Baba et al. |
| 2003/0181289 A1 | 9/2003 | Oscar Moavro |
| 2003/0181293 A1 | 9/2003 | Baatz |
| 2003/0183027 A1 | 10/2003 | Koch |
| 2003/0195089 A1 | 10/2003 | Schroeder |
| 2003/0207237 A1 | 11/2003 | Glezerman |
| 2003/0208113 A1 | 11/2003 | Mault et al. |
| 2003/0211449 A1 | 11/2003 | Seiller |
| 2003/0211916 A1 | 11/2003 | Capuano |
| 2003/0212536 A1 | 11/2003 | Wang |
| 2003/0214530 A1 | 11/2003 | Wang |
| 2003/0216228 A1 | 11/2003 | Rast |
| 2003/0220143 A1 | 11/2003 | Shteyn et al. |
| 2003/0222419 A1 | 12/2003 | Geary |
| 2003/0224337 A1 | 12/2003 | Shum et al. |
| 2003/0227473 A1 | 12/2003 | Shih |
| 2003/0232707 A1 | 12/2003 | Dalebout et al. |
| 2003/0236153 A1 | 12/2003 | Pan et al. |
| 2004/0005958 A1 | 1/2004 | Kamen et al. |
| 2004/0005959 A1 | 1/2004 | Takizawa |
| 2004/0005961 A1 | 1/2004 | Iund |
| 2004/0008220 A1 | 1/2004 | Snyder et al. |
| 2004/0010420 A1 | 1/2004 | Rooks |
| 2004/0012335 A1 | 1/2004 | Shon et al. |
| 2004/0014014 A1 | 1/2004 | Hess |
| 2004/0014567 A1 | 1/2004 | Mendel |
| 2004/0014571 A1 | 1/2004 | Haynes |
| 2004/0018917 A1 | 1/2004 | Corbalis |
| 2004/0018918 A1 | 1/2004 | Reyes |
| 2004/0019654 A1 | 1/2004 | Powers |
| 2004/0023759 A1 | 2/2004 | Duncan et al. |
| 2004/0023761 A1 | 2/2004 | Emery |
| 2004/0023762 A1 | 2/2004 | Lull |
| 2004/0023766 A1 | 2/2004 | Slone |
| 2004/0023778 A1 | 2/2004 | Kusumoto et al. |
| 2004/0025754 A1 | 2/2004 | Dye |
| 2004/0027368 A1 | 2/2004 | Snyder et al. |
| 2004/0029645 A1 | 2/2004 | Chen |
| 2004/0030762 A1 | 2/2004 | Silverthorne |
| 2004/0033865 A1 | 2/2004 | Wu |
| 2004/0043873 A1 | 3/2004 | Wilkinson et al. |
| 2004/0046692 A1 | 3/2004 | Robson |
| 2004/0051392 A1 | 3/2004 | Badarneh |
| 2004/0053748 A1 | 3/2004 | Lo et al. |
| 2004/0054350 A1 | 3/2004 | Shaughnessy |
| 2004/0063549 A1 | 4/2004 | Kuo |
| 2004/0067821 A1 | 4/2004 | Kehrbaum |
| 2004/0067833 A1 | 4/2004 | Talish |
| 2004/0072652 A1 | 4/2004 | Alessandri et al. |
| 2004/0077975 A1 | 4/2004 | Zimmerman |
| 2004/0078208 A1 | 4/2004 | Burwell |
| 2004/0082444 A1 | 4/2004 | Golesh |
| 2004/0092367 A1 | 5/2004 | Corbalis |
| 2004/0095516 A1 | 5/2004 | Rohlicek |
| 2004/0097331 A1 | 5/2004 | Zillig |
| 2004/0100484 A1 | 5/2004 | Barrett |
| 2004/0102292 A1 | 5/2004 | Pyles et al. |
| 2004/0102931 A1 | 5/2004 | Ellis |
| 2004/0103146 A1 | 5/2004 | Park |
| 2004/0103432 A1 | 5/2004 | Barrett |
| 2004/0114768 A1 | 6/2004 | Luo |
| 2004/0116837 A1 | 6/2004 | Yamaguchi |
| 2004/0116899 A1 | 6/2004 | Shaughnessy |
| 2004/0117072 A1 | 6/2004 | Takeda |
| 2004/0117214 A1 | 6/2004 | Shea |
| 2004/0127285 A1 | 7/2004 | Kavana |
| 2004/0127334 A1 | 7/2004 | Heppert |
| 2004/0127335 A1 | 7/2004 | Watterson |
| 2004/0127336 A1 | 7/2004 | Lapcevic |
| 2004/0132586 A1 | 7/2004 | Leighton et al. |
| 2004/0132587 A1 | 7/2004 | Leighton et al. |
| 2004/0136750 A1 | 7/2004 | Yoshioka et al. |
| 2004/0138030 A1 | 7/2004 | Wang |
| 2004/0142800 A1 | 7/2004 | Gerschefske |
| 2004/0144626 A1 | 7/2004 | Saeki |
| 2004/0152566 A1 | 8/2004 | Yeh |
| 2004/0155622 A1 | 8/2004 | Mayhew et al. |
| 2004/0157546 A1 | 8/2004 | Fantaay |
| 2004/0160336 A1 | 8/2004 | Hoch |
| 2004/0162188 A1 | 8/2004 | Watterson |
| 2004/0162189 A1 | 8/2004 | Hickman |
| 2004/0162191 A1 | 8/2004 | Ercanbrack |
| 2004/0163574 A1 | 8/2004 | Schoenbach |
| 2004/0166999 A1 | 8/2004 | Dodge |
| 2004/0171464 A1 | 9/2004 | Ashby et al. |
| 2004/0171465 A1 | 9/2004 | Hald |
| 2004/0176215 A1 | 9/2004 | Gramaccioni |
| 2004/0176217 A1 | 9/2004 | Watterson |
| 2004/0177531 A1 | 9/2004 | Dibenedetto et al. |
| 2004/0180719 A1 | 9/2004 | Feldman |
| 2004/0181972 A1 | 9/2004 | Csorba |
| 2004/0192514 A1 | 9/2004 | Piaget et al. |
| 2004/0198555 A1 | 10/2004 | Anderson |
| 2004/0198559 A1 | 10/2004 | Grossi |
| 2004/0198571 A1 | 10/2004 | Howell et al. |
| 2004/0208943 A1 | 10/2004 | Miketin |
| 2004/0210661 A1 | 10/2004 | Thompson |
| 2004/0214693 A1 | 10/2004 | Piaget et al. |
| 2004/0215958 A1 | 10/2004 | Ellis |
| 2004/0220017 A1 | 11/2004 | Gordon |
| 2004/0224740 A1 | 11/2004 | Ball et al. |
| 2004/0224825 A1 | 11/2004 | Giannelli et al. |
| 2004/0224827 A1 | 11/2004 | Ashley |
| 2004/0225239 A1 | 11/2004 | Yamamoto |
| 2004/0225532 A1 | 11/2004 | Gadiyak |
| 2004/0229730 A1 | 11/2004 | Ainsworth et al. |
| 2004/0230138 A1 | 11/2004 | Inoue et al. |
| 2004/0242378 A1 | 12/2004 | Pan |
| 2004/0242379 A1 | 12/2004 | Juva |
| 2004/0242380 A1 | 12/2004 | Kuivala |

(56) References Cited

U.S. PATENT DOCUMENTS

| | | |
|---|---|---|
| 2004/0242388 A1 | 12/2004 | Kusminsky |
| 2004/0248699 A1 | 12/2004 | Colley |
| 2004/0248713 A1 | 12/2004 | Campanaro |
| 2004/0254020 A1 | 12/2004 | Dragusin |
| 2004/0256524 A1 | 12/2004 | Beck et al. |
| 2004/0259689 A1 | 12/2004 | Wilkins et al. |
| 2004/0266587 A1 | 12/2004 | Miller |
| 2005/0003338 A1 | 1/2005 | Norcott et al. |
| 2005/0003931 A1 | 1/2005 | Mills et al. |
| 2005/0003933 A1 | 1/2005 | Kau |
| 2005/0008992 A1 | 1/2005 | Westergaard et al. |
| 2005/0009668 A1 | 1/2005 | Savettiere |
| 2005/0012622 A1 | 1/2005 | Sutton |
| 2005/0013433 A1 | 1/2005 | Ghassabian |
| 2005/0014571 A1 | 1/2005 | Varner |
| 2005/0015281 A1 | 1/2005 | Clark et al. |
| 2005/0020887 A1 | 1/2005 | Goldberg |
| 2005/0023292 A1 | 2/2005 | Market et al. |
| 2005/0026750 A1 | 2/2005 | Oglesby et al. |
| 2005/0026811 A1 | 2/2005 | Mjalli |
| 2005/0032610 A1 | 2/2005 | Nelson |
| 2005/0032611 A1 | 2/2005 | Webber |
| 2005/0037898 A1 | 2/2005 | Chang |
| 2005/0037904 A1 | 2/2005 | Chang |
| 2005/0038698 A1 | 2/2005 | Lukose |
| 2005/0038699 A1 | 2/2005 | Lillibridge |
| 2005/0043145 A1 | 2/2005 | Anderson et al. |
| 2005/0043146 A1 | 2/2005 | Lo et al. |
| 2005/0043155 A1 | 2/2005 | Yannitte |
| 2005/0044210 A1 | 2/2005 | Ku |
| 2005/0048461 A1 | 3/2005 | Lahteenmaki |
| 2005/0049117 A1 | 3/2005 | Rodgers |
| 2005/0049121 A1 | 3/2005 | Dalebout |
| 2005/0054492 A1 | 3/2005 | Neff |
| 2005/0054940 A1 | 3/2005 | Almen |
| 2005/0060238 A1 | 3/2005 | Gravina et al. |
| 2005/0062841 A1 | 3/2005 | Rivera-Cintron |
| 2005/0064994 A1 | 3/2005 | Matsumoto |
| 2005/0071462 A1 | 3/2005 | Bodin et al. |
| 2005/0071463 A1 | 3/2005 | Bodin et al. |
| 2005/0075213 A1 | 4/2005 | Arick |
| 2005/0075222 A1 | 4/2005 | Adley |
| 2005/0075903 A1 | 4/2005 | Piccionelli |
| 2005/0079905 A1 | 4/2005 | Martens |
| 2005/0090770 A1 | 4/2005 | Chen |
| 2005/0096187 A1 | 5/2005 | Hsu |
| 2005/0096189 A1 | 5/2005 | Chen |
| 2005/0102172 A1 | 5/2005 | Sirmans, Jr. |
| 2005/0107216 A1 | 5/2005 | Lee et al. |
| 2005/0107220 A1 | 5/2005 | Wang |
| 2005/0107226 A1 | 5/2005 | Monda |
| 2005/0107723 A1 | 5/2005 | Wehman et al. |
| 2005/0107726 A1 | 5/2005 | Oyen |
| 2005/0112601 A1 | 5/2005 | Hassibi |
| 2005/0113158 A1 | 5/2005 | Sterchi et al. |
| 2005/0113652 A1 | 5/2005 | Stark et al. |
| 2005/0113723 A1 | 5/2005 | Ueyama |
| 2005/0124463 A1 | 6/2005 | Yeo et al. |
| 2005/0124471 A1 | 6/2005 | Wilkinson |
| 2005/0129903 A1 | 6/2005 | Carr |
| 2005/0130807 A1 | 6/2005 | Cutler |
| 2005/0131319 A1 | 6/2005 | Der Meer |
| 2005/0132838 A1 | 6/2005 | Lin |
| 2005/0143226 A1 | 6/2005 | Heidecke |
| 2005/0143228 A1 | 6/2005 | Lee |
| 2005/0148398 A1 | 7/2005 | Lochtefeld et al. |
| 2005/0148439 A1 | 7/2005 | Wu |
| 2005/0148440 A1 | 7/2005 | Denton |
| 2005/0148442 A1 | 7/2005 | Watterson |
| 2005/0148443 A1 | 7/2005 | Watterson |
| 2005/0159273 A1 | 7/2005 | Chen |
| 2005/0159277 A1 | 7/2005 | Mcvay |
| 2005/0159278 A1 | 7/2005 | Mcvay |
| 2005/0159712 A1 | 7/2005 | Andersen |
| 2005/0160141 A1 | 7/2005 | Galley |
| 2005/0164832 A1 | 7/2005 | Maschke |
| 2005/0164838 A1 | 7/2005 | Watterson |
| 2005/0164839 A1 | 7/2005 | Watterson |
| 2005/0167907 A1 | 8/2005 | Curkendall et al. |
| 2005/0170935 A1 | 8/2005 | Manser |
| 2005/0170936 A1 | 8/2005 | Quinn |
| 2005/0172311 A1 | 8/2005 | Hjelt et al. |
| 2005/0181347 A1 | 8/2005 | Barnes et al. |
| 2005/0181911 A1 | 8/2005 | Porth |
| 2005/0187704 A1 | 8/2005 | Peters |
| 2005/0192162 A1 | 9/2005 | Pan |
| 2005/0195094 A1 | 9/2005 | White |
| 2005/0196737 A1 | 9/2005 | Mann |
| 2005/0202862 A1 | 9/2005 | Shuman et al. |
| 2005/0202934 A1 | 9/2005 | Olrik et al. |
| 2005/0209050 A1 | 9/2005 | Bartels |
| 2005/0209051 A1 | 9/2005 | Santomassimo et al. |
| 2005/0209052 A1 | 9/2005 | Ashby |
| 2005/0209056 A1 | 9/2005 | Daly |
| 2005/0209060 A1 | 9/2005 | Lull |
| 2005/0209061 A1 | 9/2005 | Crawford et al. |
| 2005/0209062 A1 | 9/2005 | Anderson et al. |
| 2005/0209887 A1 | 9/2005 | Pollner |
| 2005/0210169 A1 | 9/2005 | Chou |
| 2005/0212202 A1 | 9/2005 | Meyer |
| 2005/0213442 A1 | 9/2005 | Sako |
| 2005/0215335 A1 | 9/2005 | Marquardt |
| 2005/0215397 A1 | 9/2005 | Watterson |
| 2005/0227811 A1 | 10/2005 | Shum et al. |
| 2005/0227820 A1 | 10/2005 | Dyer et al. |
| 2005/0228245 A1 | 10/2005 | Quy |
| 2005/0228883 A1 | 10/2005 | Brown |
| 2005/0233859 A1 | 10/2005 | Takai |
| 2005/0233861 A1 | 10/2005 | Hickman |
| 2005/0233866 A1 | 10/2005 | Miyamaru et al. |
| 2005/0233871 A1 | 10/2005 | Anders |
| 2005/0238182 A1 | 10/2005 | Shih et al. |
| 2005/0239600 A1 | 10/2005 | Liang |
| 2005/0239601 A1 | 10/2005 | Thomas |
| 2005/0239607 A1 | 10/2005 | Chang |
| 2005/0240444 A1 | 10/2005 | Wooten |
| 2005/0245370 A1 | 11/2005 | Boland |
| 2005/0245431 A1 | 11/2005 | Demmer et al. |
| 2005/0250622 A1 | 11/2005 | Chang |
| 2005/0261609 A1 | 11/2005 | Collings et al. |
| 2005/0266961 A1 | 12/2005 | Shum et al. |
| 2005/0269601 A1 | 12/2005 | Tsubaki |
| 2005/0272561 A1 | 12/2005 | Cammerata |
| 2005/0272562 A1 | 12/2005 | Alessandri et al. |
| 2005/0272564 A1 | 12/2005 | Pyles et al. |
| 2005/0272577 A1 | 12/2005 | Olson |
| 2005/0274188 A1 | 12/2005 | Cabanis et al. |
| 2005/0277520 A1 | 12/2005 | Van Waes |
| 2005/0281963 A1 | 12/2005 | Cook |
| 2005/0283911 A1 | 12/2005 | Roussy |
| 2005/0288155 A1 | 12/2005 | Yang |
| 2005/0288954 A1 | 12/2005 | McCarthy et al. |
| 2006/0003869 A1 | 1/2006 | Huang et al. |
| 2006/0003872 A1 | 1/2006 | Chiles et al. |
| 2006/0004265 A1 | 1/2006 | Pulkkinen et al. |
| 2006/0006005 A1 | 1/2006 | Dumornay |
| 2006/0009332 A1 | 1/2006 | Jones |
| 2006/0013351 A1 | 1/2006 | Crider |
| 2006/0019224 A1 | 1/2006 | Behar et al. |
| 2006/0019804 A1 | 1/2006 | Young |
| 2006/0020174 A1 | 1/2006 | Matsumura |
| 2006/0020556 A1 | 1/2006 | Hamnen |
| 2006/0020990 A1 | 1/2006 | McEneaney |
| 2006/0034161 A1 | 2/2006 | Muller |
| 2006/0035755 A1 | 2/2006 | Dalebout |
| 2006/0035757 A1 | 2/2006 | Flick et al. |
| 2006/0035758 A1 | 2/2006 | Rogozinski |
| 2006/0035768 A1 | 2/2006 | Kowallis |
| 2006/0035774 A1 | 2/2006 | Marks |
| 2006/0040244 A1 | 2/2006 | Kain |
| 2006/0040246 A1 | 2/2006 | Ding et al. |
| 2006/0040793 A1 | 2/2006 | Martens |
| 2006/0040797 A1 | 2/2006 | Chang |
| 2006/0040798 A1 | 2/2006 | Weier et al. |

(56) References Cited

U.S. PATENT DOCUMENTS

| | | |
|---|---|---|
| 2006/0046807 A1 | 3/2006 | Sanchez |
| 2006/0046898 A1 | 3/2006 | Harvey |
| 2006/0046905 A1 | 3/2006 | Doody, Jr. |
| 2006/0047447 A1 | 3/2006 | Brady et al. |
| 2006/0052220 A1 | 3/2006 | Jackson et al. |
| 2006/0053586 A1 | 3/2006 | Chase |
| 2006/0053587 A1 | 3/2006 | Chase |
| 2006/0058155 A1 | 3/2006 | Kumar |
| 2006/0058158 A1 | 3/2006 | McAvoy |
| 2006/0058162 A1 | 3/2006 | Vieno et al. |
| 2006/0063644 A1 | 3/2006 | Yang |
| 2006/0063980 A1 | 3/2006 | Hwang et al. |
| 2006/0068978 A1 | 3/2006 | Moon |
| 2006/0069102 A1 | 3/2006 | Leban et al. |
| 2006/0075544 A1 | 4/2006 | Kriesel |
| 2006/0079800 A1 | 4/2006 | Martikka et al. |
| 2006/0084551 A1 | 4/2006 | Volpe, Jr. |
| 2006/0084851 A1 | 4/2006 | Lee et al. |
| 2006/0089238 A1 | 4/2006 | Huang et al. |
| 2006/0094569 A1 | 5/2006 | Day |
| 2006/0094570 A1 | 5/2006 | Schneider |
| 2006/0097453 A1 | 5/2006 | Feldman |
| 2006/0100069 A1 | 5/2006 | Dibble et al. |
| 2006/0100546 A1 | 5/2006 | Silk |
| 2006/0104047 A1 | 5/2006 | Guzman |
| 2006/0105888 A1 | 5/2006 | Piane, Jr. |
| 2006/0111944 A1 | 5/2006 | Sirmans, Jr. |
| 2006/0116558 A1 | 6/2006 | Jang |
| 2006/0122034 A1 | 6/2006 | Chen |
| 2006/0122035 A1 | 6/2006 | Felix |
| 2006/0122038 A1 | 6/2006 | Chou Lin |
| 2006/0122044 A1 | 6/2006 | Ho |
| 2006/0122468 A1 | 6/2006 | Tavor |
| 2006/0122474 A1 | 6/2006 | Teller et al. |
| 2006/0123814 A1 | 6/2006 | Choi et al. |
| 2006/0128534 A1 | 6/2006 | Roque |
| 2006/0129432 A1 | 6/2006 | Choi et al. |
| 2006/0132070 A1 | 6/2006 | Heydt et al. |
| 2006/0135274 A1 | 6/2006 | Henry |
| 2006/0135322 A1 | 6/2006 | Rocker |
| 2006/0142665 A1 | 6/2006 | Garay et al. |
| 2006/0148622 A1 | 7/2006 | Chen |
| 2006/0151303 A1 | 7/2006 | Motoda |
| 2006/0155576 A1 | 7/2006 | Deluz |
| 2006/0160639 A1 | 7/2006 | Klein |
| 2006/0160665 A1 | 7/2006 | Tai |
| 2006/0160666 A1 | 7/2006 | Wang |
| 2006/0160667 A1 | 7/2006 | Oglesby et al. |
| 2006/0161455 A1 | 7/2006 | Anastasia |
| 2006/0161621 A1 | 7/2006 | Rosenberg |
| 2006/0161656 A1 | 7/2006 | Sorvisto |
| 2006/0161850 A1 | 7/2006 | Seaberg |
| 2006/0166737 A1 | 7/2006 | Bentley |
| 2006/0166790 A1 | 7/2006 | Wang |
| 2006/0166791 A1 | 7/2006 | Liao |
| 2006/0166799 A1 | 7/2006 | Boland et al. |
| 2006/0172862 A1 | 8/2006 | Badarneh et al. |
| 2006/0173556 A1 | 8/2006 | Rosenberg |
| 2006/0173828 A1 | 8/2006 | Rosenberg |
| 2006/0179044 A1 | 8/2006 | Rosenberg |
| 2006/0179056 A1 | 8/2006 | Rosenberg |
| 2006/0183602 A1 | 8/2006 | Astilean |
| 2006/0183980 A1 | 8/2006 | Yang |
| 2006/0184427 A1 | 8/2006 | Singh |
| 2006/0186197 A1 | 8/2006 | Rosenberg |
| 2006/0189439 A1 | 8/2006 | Baudhuin |
| 2006/0189440 A1 | 8/2006 | Gravagne |
| 2006/0189462 A1 | 8/2006 | Pearson et al. |
| 2006/0189854 A1 | 8/2006 | Webb et al. |
| 2006/0194679 A1 | 8/2006 | Hatcher |
| 2006/0195361 A1 | 8/2006 | Rosenberg |
| 2006/0198613 A1 | 9/2006 | Lee |
| 2006/0199155 A1 | 9/2006 | Mosher |
| 2006/0199706 A1 | 9/2006 | Wehrell |
| 2006/0203972 A1 | 9/2006 | Hays |
| 2006/0205349 A1 | 9/2006 | Passier et al. |
| 2006/0205564 A1 | 9/2006 | Peterson |
| 2006/0205568 A1 | 9/2006 | Huang |
| 2006/0205569 A1 | 9/2006 | Watterson |
| 2006/0205571 A1 | 9/2006 | Krull |
| 2006/0217231 A1 | 9/2006 | Parks et al. |
| 2006/0217236 A1 | 9/2006 | Watterson |
| 2006/0217245 A1 | 9/2006 | Golesh et al. |
| 2006/0218253 A1 | 9/2006 | Hays |
| 2006/0223635 A1 | 10/2006 | Rosenberg |
| 2006/0223637 A1 | 10/2006 | Rosenberg |
| 2006/0223674 A1 | 10/2006 | Korkie |
| 2006/0223680 A1 | 10/2006 | Chang |
| 2006/0223681 A1 | 10/2006 | Loane |
| 2006/0224051 A1 | 10/2006 | Teller et al. |
| 2006/0228683 A1 | 10/2006 | Jianping |
| 2006/0229058 A1 | 10/2006 | Rosenberg |
| 2006/0229163 A1 | 10/2006 | Waters |
| 2006/0229164 A1 | 10/2006 | Einav |
| 2006/0229170 A1 | 10/2006 | Ozawa et al. |
| 2006/0232147 A1 | 10/2006 | Cheng |
| 2006/0234832 A1 | 10/2006 | Toyama et al. |
| 2006/0234840 A1 | 10/2006 | Watson |
| 2006/0240947 A1 | 10/2006 | Qu |
| 2006/0240951 A1 | 10/2006 | Wang |
| 2006/0240959 A1 | 10/2006 | Huang |
| 2006/0244187 A1 | 11/2006 | Downey |
| 2006/0247095 A1 | 11/2006 | Rummerfield |
| 2006/0247098 A1 | 11/2006 | Raniere |
| 2006/0247109 A1 | 11/2006 | Powell |
| 2006/0248965 A1* | 11/2006 | Wyatt ................ A61B 5/0002 73/862.391 |
| 2006/0250524 A1 | 11/2006 | Roche |
| 2006/0251638 A1 | 11/2006 | Guenzler-Pukall |
| 2006/0252600 A1 | 11/2006 | Grogan |
| 2006/0252602 A1 | 11/2006 | Brown |
| 2006/0252608 A1 | 11/2006 | Kang et al. |
| 2006/0253010 A1 | 11/2006 | Brady et al. |
| 2006/0253210 A1 | 11/2006 | Rosenberg |
| 2006/0256007 A1 | 11/2006 | Rosenberg |
| 2006/0256008 A1 | 11/2006 | Rosenberg |
| 2006/0258513 A1 | 11/2006 | Routley |
| 2006/0258515 A1 | 11/2006 | Kang et al. |
| 2006/0259275 A1 | 11/2006 | Maschke |
| 2006/0259574 A1 | 11/2006 | Rosenberg |
| 2006/0262752 A1 | 11/2006 | Moore et al. |
| 2006/0264299 A1 | 11/2006 | Farinelli et al. |
| 2006/0264306 A1 | 11/2006 | Tischler |
| 2006/0264730 A1 | 11/2006 | Stivoric et al. |
| 2006/0265469 A1 | 11/2006 | Estrade |
| 2006/0269251 A1 | 11/2006 | Hsu |
| 2006/0270522 A1 | 11/2006 | Yonehana et al. |
| 2006/0271286 A1 | 11/2006 | Rosenberg |
| 2006/0276306 A1 | 12/2006 | Pan et al. |
| 2006/0279294 A1 | 12/2006 | Cehelnik |
| 2006/0281603 A1 | 12/2006 | Hickman |
| 2006/0281605 A1 | 12/2006 | Lo |
| 2006/0283050 A1 | 12/2006 | Carnes et al. |
| 2006/0287089 A1 | 12/2006 | Addington et al. |
| 2006/0287147 A1 | 12/2006 | Kriesel |
| 2006/0287161 A1 | 12/2006 | Dalebout |
| 2006/0287163 A1 | 12/2006 | Wang |
| 2006/0288846 A1 | 12/2006 | Logan |
| 2006/0293608 A1 | 12/2006 | Rothman et al. |
| 2006/0293617 A1 | 12/2006 | Einav et al. |
| 2007/0000154 A1 | 1/2007 | Dibenedetto |
| 2007/0004561 A1 | 1/2007 | Yoo |
| 2007/0004562 A1 | 1/2007 | Pan et al. |
| 2007/0004565 A1 | 1/2007 | Gebhardt |
| 2007/0004569 A1 | 1/2007 | Cao |
| 2007/0004736 A1 | 1/2007 | Kubo |
| 2007/0005395 A1 | 1/2007 | Singh |
| 2007/0006489 A1 | 1/2007 | Case, Jr. et al. |
| 2007/0010383 A1 | 1/2007 | Pertegaz-Esteban |
| 2007/0011027 A1 | 1/2007 | Melendez |
| 2007/0011391 A1 | 1/2007 | Kim et al. |
| 2007/0011920 A1 | 1/2007 | DiBenedetto et al. |
| 2007/0013655 A1 | 1/2007 | Rosenberg et al. |
| 2007/0014422 A1 | 1/2007 | Wesemann et al. |

(56) References Cited

U.S. PATENT DOCUMENTS

| | | |
|---|---|---|
| 2007/0015635 A1 | 1/2007 | Donner |
| 2007/0015636 A1 | 1/2007 | Molter |
| 2007/0015752 A1 | 1/2007 | Hangauer, Jr. |
| 2007/0016444 A1 | 1/2007 | Holkkola |
| 2007/0016930 A1 | 1/2007 | Wesemann et al. |
| 2007/0026958 A1 | 2/2007 | Barasch et al. |
| 2007/0026999 A1 | 2/2007 | Merolle et al. |
| 2007/0027000 A1 | 2/2007 | Shirai et al. |
| 2007/0027002 A1 | 2/2007 | Clark et al. |
| 2007/0027003 A1 | 2/2007 | Clark |
| 2007/0028749 A1 | 2/2007 | Basson |
| 2007/0032345 A1 | 2/2007 | Padmanabhan |
| 2007/0032351 A1 | 2/2007 | Reyes |
| 2007/0032353 A1 | 2/2007 | Wilkins et al. |
| 2007/0032481 A1 | 2/2007 | Dvorak |
| 2007/0033012 A1 | 2/2007 | Rosenberg |
| 2007/0033068 A1 | 2/2007 | Rao |
| 2007/0033069 A1 | 2/2007 | Rao |
| 2007/0037667 A1 | 2/2007 | Gordon |
| 2007/0038038 A1 | 2/2007 | Stivoric et al. |
| 2007/0038137 A1 | 2/2007 | Arand et al. |
| 2007/0038153 A1 | 2/2007 | Basson |
| 2007/0042866 A1 | 2/2007 | Skilken |
| 2007/0042868 A1 | 2/2007 | Fisher |
| 2007/0049384 A1 | 3/2007 | King et al. |
| 2007/0049461 A1 | 3/2007 | Kim et al. |
| 2007/0049462 A1 | 3/2007 | Asukai et al. |
| 2007/0049464 A1 | 3/2007 | Chou |
| 2007/0049465 A1 | 3/2007 | Wu |
| 2007/0049466 A1 | 3/2007 | Hubbard |
| 2007/0049470 A1 | 3/2007 | Pyles et al. |
| 2007/0051369 A1 | 3/2007 | Choi et al. |
| 2007/0054778 A1 | 3/2007 | Blanarovich |
| 2007/0054790 A1 | 3/2007 | Dodge et al. |
| 2007/0060408 A1 | 3/2007 | Schultz et al. |
| 2007/0060446 A1 | 3/2007 | Asukai et al. |
| 2007/0060449 A1 | 3/2007 | Lo |
| 2007/0060450 A1 | 3/2007 | Lo |
| 2007/0060451 A1 | 3/2007 | Lucas |
| 2007/0060898 A1 | 3/2007 | Shaughnessy |
| 2007/0061314 A1 | 3/2007 | Rosenberg |
| 2007/0063033 A1 | 3/2007 | Silverbrook et al. |
| 2007/0066448 A1 | 3/2007 | Pan et al. |
| 2007/0072156 A1 | 3/2007 | Kaufman et al. |
| 2007/0072748 A1 | 3/2007 | Lee |
| 2007/0072752 A1 | 3/2007 | Koch |
| 2007/0074617 A1 | 4/2007 | Vergo |
| 2007/0075127 A1 | 4/2007 | Rosenberg |
| 2007/0079691 A1 | 4/2007 | Turner |
| 2007/0083095 A1 | 4/2007 | Rippo et al. |
| 2007/0083323 A1 | 4/2007 | Rosenberg |
| 2007/0083975 A1 | 4/2007 | Senegal |
| 2007/0087908 A1 | 4/2007 | Pan et al. |
| 2007/0093360 A1 | 4/2007 | Neff |
| 2007/0093369 A1 | 4/2007 | Bocchicchio |
| 2007/0100595 A1 | 5/2007 | Earles |
| 2007/0100666 A1 | 5/2007 | Stivoric et al. |
| 2007/0106484 A1 | 5/2007 | Sweatman et al. |
| 2007/0109491 A1 | 5/2007 | Howell et al. |
| 2007/0111753 A1 | 5/2007 | Vock |
| 2007/0111858 A1 | 5/2007 | Dugan |
| 2007/0111866 A1 | 5/2007 | McVay et al. |
| 2007/0117680 A1 | 5/2007 | Neff |
| 2007/0117683 A1 | 5/2007 | Ercanbrack et al. |
| 2007/0117693 A1 | 5/2007 | Ilioi |
| 2007/0122786 A1 | 5/2007 | Relan et al. |
| 2007/0123389 A1 | 5/2007 | Martin |
| 2007/0123390 A1 | 5/2007 | Mathis |
| 2007/0123395 A1 | 5/2007 | Ellis |
| 2007/0123396 A1 | 5/2007 | Ellis |
| 2007/0124762 A1 | 5/2007 | Chickering et al. |
| 2007/0129220 A1 | 6/2007 | Bardha |
| 2007/0129907 A1 | 6/2007 | Demon |
| 2007/0131409 A1 | 6/2007 | Asahi |
| 2007/0135264 A1 | 6/2007 | Rosenberg |
| 2007/0135738 A1 | 6/2007 | Bonutti |
| 2007/0136093 A1 | 6/2007 | Rankin et al. |
| 2007/0137307 A1 | 6/2007 | Gruben |
| 2007/0137331 A1 | 6/2007 | Kachouh |
| 2007/0140403 A1 | 6/2007 | Yuguchi et al. |
| 2007/0142175 A1 | 6/2007 | Morgan |
| 2007/0142177 A1 | 6/2007 | Simms et al. |
| 2007/0142179 A1 | 6/2007 | Terao et al. |
| 2007/0142183 A1 | 6/2007 | Chang |
| 2007/0142187 A1 | 6/2007 | Kolomeir |
| 2007/0146347 A1 | 6/2007 | Rosenberg |
| 2007/0149362 A1 | 6/2007 | Lee et al. |
| 2007/0149363 A1 | 6/2007 | Wang |
| 2007/0149364 A1 | 6/2007 | Blau |
| 2007/0150188 A1 | 6/2007 | Rosenberg |
| 2007/0151489 A1 | 7/2007 | Byrne |
| 2007/0153639 A1 | 7/2007 | Lafever |
| 2007/0155277 A1 | 7/2007 | Amitai et al. |
| 2007/0155495 A1 | 7/2007 | Goo |
| 2007/0155589 A1 | 7/2007 | Feldman |
| 2007/0156335 A1 | 7/2007 | McBride et al. |
| 2007/0161459 A1 | 7/2007 | Watson |
| 2007/0161466 A1 | 7/2007 | Oglesby et al. |
| 2007/0161468 A1 | 7/2007 | Yanagisawa et al. |
| 2007/0167291 A1 | 7/2007 | Kuo |
| 2007/0167292 A1 | 7/2007 | Kuo |
| 2007/0167293 A1 | 7/2007 | Nally |
| 2007/0169381 A1 | 7/2007 | Gordon |
| 2007/0173355 A1 | 7/2007 | Klein |
| 2007/0176035 A1 | 8/2007 | Campbell |
| 2007/0179023 A1 | 8/2007 | Dyer |
| 2007/0179359 A1 | 8/2007 | Goodwin |
| 2007/0180737 A1 | 8/2007 | DiBenedetto et al. |
| 2007/0184953 A1 | 8/2007 | Luberski et al. |
| 2007/0189544 A1 | 8/2007 | Rosenberg |
| 2007/0190508 A1 | 8/2007 | Dalton |
| 2007/0191141 A1 | 8/2007 | Weber |
| 2007/0191190 A1 | 8/2007 | Kuo |
| 2007/0191197 A1 | 8/2007 | Vittone |
| 2007/0197193 A1 | 8/2007 | Zhou |
| 2007/0197274 A1 | 8/2007 | Dugan |
| 2007/0197345 A1 | 8/2007 | Wallace et al. |
| 2007/0197346 A1 | 8/2007 | Seliber |
| 2007/0197353 A1 | 8/2007 | Hundley |
| 2007/0197920 A1 | 8/2007 | Adams |
| 2007/0201727 A1 | 8/2007 | Birrell et al. |
| 2007/0202992 A1 | 8/2007 | Grasshoff |
| 2007/0203004 A1 | 8/2007 | Campanaro et al. |
| 2007/0204430 A1 | 9/2007 | Chase |
| 2007/0207733 A1 | 9/2007 | Wong et al. |
| 2007/0208392 A1 | 9/2007 | Kuschner et al. |
| 2007/0208530 A1 | 9/2007 | Vock |
| 2007/0213110 A1 | 9/2007 | Rosenberg |
| 2007/0213126 A1 | 9/2007 | Deutsch et al. |
| 2007/0213178 A1 | 9/2007 | Lemmela |
| 2007/0213183 A1 | 9/2007 | Menektchiev |
| 2007/0214630 A1 | 9/2007 | Kim |
| 2007/0218432 A1 | 9/2007 | Glass |
| 2007/0219057 A1 | 9/2007 | Fleishman |
| 2007/0219058 A1 | 9/2007 | Fleishman |
| 2007/0219059 A1 | 9/2007 | Schwartz |
| 2007/0219066 A1 | 9/2007 | Wang |
| 2007/0219068 A1 | 9/2007 | Korfmacher |
| 2007/0219074 A1 | 9/2007 | Pride |
| 2007/0219457 A1 | 9/2007 | Lo |
| 2007/0225118 A1 | 9/2007 | Giorno |
| 2007/0225119 A1 | 9/2007 | Schenk |
| 2007/0225120 A1 | 9/2007 | Schenk |
| 2007/0225126 A1 | 9/2007 | Yoo |
| 2007/0225127 A1 | 9/2007 | Pan et al. |
| 2007/0225622 A1 | 9/2007 | Huang et al. |
| 2007/0232450 A1 | 10/2007 | Hanoun |
| 2007/0232452 A1 | 10/2007 | Hanoun |
| 2007/0232453 A1 | 10/2007 | Hanoun |
| 2007/0232455 A1 | 10/2007 | Hanoun |
| 2007/0232461 A1 | 10/2007 | Jenkins et al. |
| 2007/0232463 A1 | 10/2007 | Wu |
| 2007/0233743 A1 | 10/2007 | Rosenberg |
| 2007/0239479 A1 | 10/2007 | Arrasvuori |

(56) References Cited

U.S. PATENT DOCUMENTS

| | | |
|---|---|---|
| 2007/0243974 A1 | 10/2007 | Li |
| 2007/0245258 A1 | 10/2007 | Ginggen et al. |
| 2007/0245612 A1 | 10/2007 | Tresenfeld |
| 2007/0247320 A1 | 10/2007 | Morahan |
| 2007/0249467 A1 | 10/2007 | Hong et al. |
| 2007/0249468 A1 | 10/2007 | Chen |
| 2007/0254778 A1 | 11/2007 | Ashby |
| 2007/0260482 A1 | 11/2007 | Nurmela |
| 2007/0265146 A1 | 11/2007 | Kowalczewski |
| 2007/0270294 A1 | 11/2007 | Sheets |
| 2007/0270663 A1 | 11/2007 | Ng et al. |
| 2007/0270667 A1 | 11/2007 | Coppi et al. |
| 2007/0270721 A1 | 11/2007 | Ananny et al. |
| 2007/0270726 A1 | 11/2007 | Chou |
| 2007/0271065 A1 | 11/2007 | Gupta et al. |
| 2007/0271116 A1 | 11/2007 | Wysocki et al. |
| 2007/0271387 A1 | 11/2007 | Lydon et al. |
| 2007/0272011 A1 | 11/2007 | Chapa, Jr. |
| 2007/0275825 A1 | 11/2007 | O'brien |
| 2007/0275826 A1 | 11/2007 | Niemimaki et al. |
| 2007/0275830 A1 | 11/2007 | Lee |
| 2007/0276870 A1 | 11/2007 | Rosenberg et al. |
| 2007/0281831 A1 | 12/2007 | Wang |
| 2007/0283853 A1 | 12/2007 | Sun |
| 2007/0284495 A1 | 12/2007 | Charles |
| 2007/0287141 A1 | 12/2007 | Milner |
| 2007/0287597 A1 | 12/2007 | Cameron |
| 2007/0287601 A1 | 12/2007 | Burck et al. |
| 2007/0287930 A1 | 12/2007 | Sutton |
| 2007/0288204 A1 | 12/2007 | Gienke et al. |
| 2007/0288251 A1 | 12/2007 | Ebrom et al. |
| 2007/0288331 A1 | 12/2007 | Ebrom et al. |
| 2007/0288476 A1 | 12/2007 | Flanagan, III |
| 2007/0288969 A1 | 12/2007 | Prum et al. |
| 2007/0293781 A1 | 12/2007 | Sims et al. |
| 2007/0296313 A1 | 12/2007 | Wang |
| 2007/0298405 A1 | 12/2007 | Ebrom et al. |
| 2007/0298935 A1 | 12/2007 | Badarneh |
| 2007/0298937 A1 | 12/2007 | Shah |
| 2008/0001772 A1 | 1/2008 | Saito |
| 2008/0001866 A1 | 1/2008 | Martin |
| 2008/0004162 A1 | 1/2008 | Chen |
| 2008/0005276 A1 | 1/2008 | Frederick |
| 2008/0009275 A1 | 1/2008 | Werner |
| 2008/0015061 A1 | 1/2008 | Klein |
| 2008/0015087 A1 | 1/2008 | Negrin |
| 2008/0015088 A1 | 1/2008 | Del Monaco |
| 2008/0015089 A1 | 1/2008 | Hurwitz |
| 2008/0015094 A1 | 1/2008 | Casagrande |
| 2008/0018211 A1 | 1/2008 | Dye |
| 2008/0020898 A1 | 1/2008 | Pyles et al. |
| 2008/0020902 A1 | 1/2008 | Arnold |
| 2008/0020907 A1 | 1/2008 | Lin |
| 2008/0026658 A1 | 1/2008 | Kriesel |
| 2008/0026838 A1 | 1/2008 | Dunstan et al. |
| 2008/0027673 A1 | 1/2008 | Trumm |
| 2008/0032864 A1 | 2/2008 | Hakki |
| 2008/0032865 A1 | 2/2008 | Wu |
| 2008/0032870 A1 | 2/2008 | Wu |
| 2008/0032871 A1 | 2/2008 | Yeh |
| 2008/0037375 A1 | 2/2008 | Ellner |
| 2008/0039301 A1 | 2/2008 | Halbridge |
| 2008/0045384 A1 | 2/2008 | Matsubara |
| 2008/0046246 A1 | 2/2008 | Hakki |
| 2008/0051256 A1 | 2/2008 | Ashby et al. |
| 2008/0051258 A1 | 2/2008 | Schmehl et al. |
| 2008/0051261 A1 | 2/2008 | Lewis |
| 2008/0051919 A1 | 2/2008 | Sakai et al. |
| 2008/0051993 A1 | 2/2008 | Graham |
| 2008/0057889 A1 | 3/2008 | Jan |
| 2008/0058169 A1 | 3/2008 | Fox |
| 2008/0058170 A1 | 3/2008 | Giannascoli et al. |
| 2008/0059064 A1 | 3/2008 | Werner |
| 2008/0062818 A1 | 3/2008 | Plancon et al. |
| 2008/0064571 A1 | 3/2008 | Lee |
| 2008/0067302 A1 | 3/2008 | Olivera |
| 2008/0068559 A1 | 3/2008 | Plancon et al. |
| 2008/0070756 A1 | 3/2008 | Chu |
| 2008/0076637 A1 | 3/2008 | Gilley et al. |
| 2008/0076969 A1 | 3/2008 | Kraft |
| 2008/0076972 A1 | 3/2008 | Dorogusker et al. |
| 2008/0077489 A1 | 3/2008 | Gilley et al. |
| 2008/0077619 A1 | 3/2008 | Gilley et al. |
| 2008/0082311 A1 | 4/2008 | Meijer et al. |
| 2008/0086318 A1 | 4/2008 | Gilley et al. |
| 2008/0089551 A1 | 4/2008 | Heather et al. |
| 2008/0090703 A1 | 4/2008 | Rosenberg |
| 2008/0096726 A1 | 4/2008 | Riley et al. |
| 2008/0096745 A1 | 4/2008 | Perry |
| 2008/0097633 A1 | 4/2008 | Jochelson et al. |
| 2008/0098797 A1 | 5/2008 | Considine |
| 2008/0103023 A1 | 5/2008 | Chung |
| 2008/0103024 A1 | 5/2008 | Habing |
| 2008/0103030 A1 | 5/2008 | Watson et al. |
| 2008/0103034 A1 | 5/2008 | Mihara et al. |
| 2008/0108481 A1 | 5/2008 | Limma |
| 2008/0108917 A1 | 5/2008 | Watson |
| 2008/0109121 A1 | 5/2008 | Takeda |
| 2008/0109243 A1 | 5/2008 | Ebrom et al. |
| 2008/0109295 A1 | 5/2008 | McConochie et al. |
| 2008/0109310 A1 | 5/2008 | Ebrom et al. |
| 2008/0109841 A1 | 5/2008 | Healther et al. |
| 2008/0109851 A1 | 5/2008 | Healther et al. |
| 2008/0119332 A1 | 5/2008 | Roman |
| 2008/0119333 A1 | 5/2008 | Bowser |
| 2008/0119337 A1 | 5/2008 | Wilkins |
| 2008/0120436 A1 | 5/2008 | Cowgill et al. |
| 2008/0129825 A1 | 6/2008 | DeAngelis |
| 2008/0132386 A1 | 6/2008 | Helie |
| 2008/0132798 A1 | 6/2008 | Hong et al. |
| 2008/0139370 A1 | 6/2008 | Charnitski |
| 2008/0141135 A1 | 6/2008 | Mason et al. |
| 2008/0146334 A1 | 6/2008 | Kil |
| 2008/0146336 A1 | 6/2008 | Feldman |
| 2008/0146416 A1 | 6/2008 | Mueller et al. |
| 2008/0146890 A1 | 6/2008 | LeBoeuf et al. |
| 2008/0146892 A1 | 6/2008 | LeBoeuf et al. |
| 2008/0147502 A1 | 6/2008 | Baker |
| 2008/0153670 A1 | 6/2008 | Mckirdy |
| 2008/0153671 A1 | 6/2008 | Ogg et al. |
| 2008/0153682 A1 | 6/2008 | Chen et al. |
| 2008/0155077 A1 | 6/2008 | James |
| 2008/0161168 A1 | 7/2008 | Hsiao |
| 2008/0161170 A1 | 7/2008 | Lumpee |
| 2008/0161653 A1 | 7/2008 | Lin et al. |
| 2008/0167535 A1 | 7/2008 | Stivoric et al. |
| 2008/0167536 A1 | 7/2008 | Teller |
| 2008/0167958 A1 | 7/2008 | Balmadur |
| 2008/0171636 A1 | 7/2008 | Usui et al. |
| 2008/0171640 A1 | 7/2008 | Chang |
| 2008/0171922 A1 | 7/2008 | Teller |
| 2008/0171945 A1 | 7/2008 | Dotter |
| 2008/0172328 A1 | 7/2008 | Ajilian |
| 2008/0176655 A1 | 7/2008 | James |
| 2008/0176713 A1 | 7/2008 | Olivera Brizzio |
| 2008/0176717 A1 | 7/2008 | Wang |
| 2008/0176718 A1 | 7/2008 | Wang |
| 2008/0176721 A1 | 7/2008 | Boren |
| 2008/0179214 A1 | 7/2008 | Hall |
| 2008/0182685 A1 | 7/2008 | Marty et al. |
| 2008/0182724 A1 | 7/2008 | Guthrie |
| 2008/0183049 A1 | 7/2008 | Karkanias et al. |
| 2008/0183052 A1 | 7/2008 | Teller |
| 2008/0187689 A1 | 8/2008 | Dierkens et al. |
| 2008/0188354 A1 | 8/2008 | Pauws et al. |
| 2008/0188362 A1 | 8/2008 | Chen |
| 2008/0189733 A1 | 8/2008 | Apostolopoulos |
| 2008/0190745 A1 | 8/2008 | Taniguchi et al. |
| 2008/0191864 A1 | 8/2008 | Wolfson |
| 2008/0195258 A1 | 8/2008 | Schendel |
| 2008/0200287 A1 | 8/2008 | Marty et al. |
| 2008/0200310 A1 | 8/2008 | Tagliabue |
| 2008/0200312 A1 | 8/2008 | Tagliabue |
| 2008/0200314 A1 | 8/2008 | Dalebout et al. |

(56) References Cited

U.S. PATENT DOCUMENTS

| | | |
|---|---|---|
| 2008/0200778 A1 | 8/2008 | Taskinen |
| 2008/0204225 A1 | 8/2008 | Kitchen |
| 2008/0207401 A1 | 8/2008 | Harding et al. |
| 2008/0207402 A1 | 8/2008 | Fisher et al. |
| 2008/0207407 A1 | 8/2008 | Yeh |
| 2008/0214358 A1 | 9/2008 | Ogg et al. |
| 2008/0214359 A1 | 9/2008 | Niva et al. |
| 2008/0214903 A1 | 9/2008 | Orbach |
| 2008/0214971 A1 | 9/2008 | Talish |
| 2008/0216717 A1 | 9/2008 | Jones |
| 2008/0218307 A1 | 9/2008 | Schoettle |
| 2008/0220941 A1 | 9/2008 | Shaw |
| 2008/0224988 A1 | 9/2008 | Whang |
| 2008/0228110 A1 | 9/2008 | Berme |
| 2008/0229875 A1 | 9/2008 | Ray |
| 2008/0234023 A1 | 9/2008 | Mullahkhel et al. |
| 2008/0234110 A1 | 9/2008 | Webber et al. |
| 2008/0234111 A1 | 9/2008 | Packham |
| 2008/0234113 A1 | 9/2008 | Einav |
| 2008/0242510 A1 | 10/2008 | Topel |
| 2008/0242511 A1 | 10/2008 | Munoz et al. |
| 2008/0242512 A1 | 10/2008 | Kim |
| 2008/0242513 A1 | 10/2008 | Skilken et al. |
| 2008/0244870 A1 | 10/2008 | Chase |
| 2008/0245944 A1 | 10/2008 | Chase |
| 2008/0248926 A1 | 10/2008 | Cole et al. |
| 2008/0248935 A1 | 10/2008 | Solow |
| 2008/0249736 A1 | 10/2008 | Prstojevich |
| 2008/0250729 A1 | 10/2008 | Kriesel |
| 2008/0253378 A1 | 10/2008 | Curry |
| 2008/0254420 A1 | 10/2008 | Nerenberg |
| 2008/0254947 A1 | 10/2008 | Mackay |
| 2008/0255430 A1 | 10/2008 | Alexandersson et al. |
| 2008/0255794 A1 | 10/2008 | Levine |
| 2008/0261636 A1 | 10/2008 | Lau et al. |
| 2008/0261774 A1 | 10/2008 | Fisher |
| 2008/0261776 A1 | 10/2008 | Skiba |
| 2008/0262381 A1 | 10/2008 | Kolen |
| 2008/0262392 A1 | 10/2008 | Ananny et al. |
| 2008/0267444 A1 | 10/2008 | Simons-Nikolova et al. |
| 2008/0269016 A1 | 10/2008 | Ungari et al. |
| 2008/0269017 A1 | 10/2008 | Ungari |
| 2008/0273008 A1 | 11/2008 | Chang |
| 2008/0279896 A1 | 11/2008 | Heinen et al. |
| 2008/0280732 A1 | 11/2008 | Jones |
| 2008/0280733 A1 | 11/2008 | Dickie et al. |
| 2008/0280734 A1 | 11/2008 | Dickie et al. |
| 2008/0280735 A1 | 11/2008 | Dickie |
| 2008/0287262 A1 | 11/2008 | Chou |
| 2008/0293023 A1 | 11/2008 | Diehl |
| 2008/0295129 A1 | 11/2008 | Laut |
| 2008/0296883 A1 | 12/2008 | Burkhardtsmaier |
| 2008/0300109 A1 | 12/2008 | Karkanias et al. |
| 2008/0300110 A1 | 12/2008 | Smith et al. |
| 2008/0300114 A1 | 12/2008 | Dalebout |
| 2008/0300115 A1 | 12/2008 | Erlandson |
| 2008/0300116 A1 | 12/2008 | Eder |
| 2008/0300914 A1 | 12/2008 | Karkanias et al. |
| 2008/0305934 A1 | 12/2008 | Medina |
| 2008/0305936 A1 | 12/2008 | Cao |
| 2008/0306762 A1 | 12/2008 | James |
| 2008/0312039 A1 | 12/2008 | Bucay-Bissu |
| 2008/0312041 A1 | 12/2008 | Schwabe et al. |
| 2008/0312047 A1 | 12/2008 | Feng |
| 2008/0315371 A1 | 12/2008 | Tang et al. |
| 2008/0318737 A1 | 12/2008 | Chu |
| 2008/0319787 A1 | 12/2008 | Stivoric |
| 2008/0319796 A1 | 12/2008 | Stivoric |
| 2008/0319855 A1 | 12/2008 | Stivoric |
| 2009/0001831 A1 | 1/2009 | Cho et al. |
| 2009/0005224 A1 | 1/2009 | Davis et al. |
| 2009/0011907 A1 | 1/2009 | Radow |
| 2009/0017991 A1 | 1/2009 | Hung |
| 2009/0023553 A1 | 1/2009 | Shim |
| 2009/0023554 A1 | 1/2009 | Shim |
| 2009/0023556 A1 | 1/2009 | Daly |
| 2009/0024233 A1 | 1/2009 | Shirai et al. |
| 2009/0027925 A1 | 1/2009 | Kanouda et al. |
| 2009/0028005 A1 | 1/2009 | You et al. |
| 2009/0029831 A1 | 1/2009 | Weier |
| 2009/0036276 A1 | 2/2009 | Loach |
| 2009/0040231 A1 | 2/2009 | Sano et al. |
| 2009/0040301 A1 | 2/2009 | Sandler et al. |
| 2009/0041298 A1 | 2/2009 | Sandler et al. |
| 2009/0042174 A1 | 2/2009 | Aries |
| 2009/0042696 A1 | 2/2009 | Wang |
| 2009/0042698 A1 | 2/2009 | Wang |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0048073 A1 | 2/2009 | Roimicher |
| 2009/0048079 A1 | 2/2009 | Nalley |
| 2009/0048493 A1 | 2/2009 | James et al. |
| 2009/0048939 A1 | 2/2009 | Williams |
| 2009/0049092 A1 | 2/2009 | Capio et al. |
| 2009/0053682 A1 | 2/2009 | Stern |
| 2009/0054207 A1 | 2/2009 | Lin et al. |
| 2009/0054214 A1 | 2/2009 | Kadar |
| 2009/0054751 A1 | 2/2009 | Babashan et al. |
| 2009/0061870 A1 | 3/2009 | Finkelstein et al. |
| 2009/0062072 A1 | 3/2009 | Packham |
| 2009/0062598 A1 | 3/2009 | Haisma et al. |
| 2009/0069156 A1 | 3/2009 | Veli-Pekka Kurunmäki et al. |
| 2009/0069159 A1 | 3/2009 | Wang |
| 2009/0069722 A1 | 3/2009 | Flaction et al. |
| 2009/0075781 A1 | 3/2009 | Schwarzberg et al. |
| 2009/0075784 A1 | 3/2009 | Hoggan |
| 2009/0076335 A1 | 3/2009 | Schwarzberg et al. |
| 2009/0076903 A1 | 3/2009 | Schwarzberg et al. |
| 2009/0080808 A1 | 3/2009 | Hagen |
| 2009/0082176 A1 | 3/2009 | Watterson et al. |
| 2009/0082880 A1 | 3/2009 | Saunders |
| 2009/0085873 A1 | 4/2009 | Betts et al. |
| 2009/0088248 A1 | 4/2009 | Stevens |
| 2009/0088299 A1 | 4/2009 | Chen |
| 2009/0088301 A1 | 4/2009 | Alling |
| 2009/0093341 A1 | 4/2009 | James |
| 2009/0093347 A1 | 4/2009 | Wang |
| 2009/0098980 A1 | 4/2009 | Waters |
| 2009/0098981 A1 | 4/2009 | Del Giorno |
| 2009/0100718 A1 | 4/2009 | Gerber |
| 2009/0105047 A1 | 4/2009 | Guidi et al. |
| 2009/0105052 A1 | 4/2009 | Dalebout et al. |
| 2009/0105548 A1 | 4/2009 | Bart |
| 2009/0105560 A1 | 4/2009 | Solomon |
| 2009/0109346 A1 | 4/2009 | Viarani et al. |
| 2009/0111656 A1 | 4/2009 | Sullivan |
| 2009/0111658 A1 | 4/2009 | Juan |
| 2009/0111664 A1 | 4/2009 | Kau |
| 2009/0111665 A1 | 4/2009 | Wang |
| 2009/0111666 A1 | 4/2009 | Wang |
| 2009/0111670 A1 | 4/2009 | Williams |
| 2009/0117890 A1 | 5/2009 | Jacobsen et al. |
| 2009/0118098 A1 | 5/2009 | Yeh |
| 2009/0118099 A1 | 5/2009 | Fisher |
| 2009/0118103 A1 | 5/2009 | Ellis |
| 2009/0124460 A1 | 5/2009 | Chen |
| 2009/0124463 A1 | 5/2009 | Lin |
| 2009/0124464 A1 | 5/2009 | Kastelic |
| 2009/0124465 A1 | 5/2009 | Wang |
| 2009/0124466 A1 | 5/2009 | Zhang |
| 2009/0128342 A1 | 5/2009 | Cohen |
| 2009/0128516 A1 | 5/2009 | Rimon et al. |
| 2009/0137367 A1 | 5/2009 | Hendrickson et al. |
| 2009/0144080 A1 | 6/2009 | Gray et al. |
| 2009/0144084 A1 | 6/2009 | Neumaier |
| 2009/0144639 A1 | 6/2009 | Nims et al. |
| 2009/0149299 A1 | 6/2009 | Tchao et al. |
| 2009/0149721 A1 | 6/2009 | Yang |
| 2009/0150178 A1 | 6/2009 | Sutton et al. |
| 2009/0156363 A1 | 6/2009 | Guidi et al. |
| 2009/0156364 A1 | 6/2009 | Simeoni |
| 2009/0158871 A1 | 6/2009 | Chuo |
| 2009/0163262 A1 | 6/2009 | Kang |

(56) References Cited

U.S. PATENT DOCUMENTS

| | | |
|---|---|---|
| 2009/0163323 A1 | 6/2009 | Bocchicchio |
| 2009/0163326 A1 | 6/2009 | Wang |
| 2009/0163327 A1 | 6/2009 | Huang et al. |
| 2009/0163334 A1 | 6/2009 | Gibson et al. |
| 2009/0170663 A1 | 7/2009 | Cox et al. |
| 2009/0170667 A1 | 7/2009 | Irving et al. |
| 2009/0170672 A1 | 7/2009 | Mcmullen |
| 2009/0171229 A1 | 7/2009 | Saldarelli |
| 2009/0174558 A1 | 7/2009 | White |
| 2009/0176526 A1 | 7/2009 | Altman |
| 2009/0176581 A1 | 7/2009 | Barnes et al. |
| 2009/0176625 A1 | 7/2009 | Giannelli et al. |
| 2009/0176628 A1 | 7/2009 | Radding et al. |
| 2009/0177068 A1 | 7/2009 | Stivoric et al. |
| 2009/0180646 A1 | 7/2009 | Vulfson et al. |
| 2009/0181826 A1 | 7/2009 | Turner |
| 2009/0181829 A1 | 7/2009 | Wu |
| 2009/0181830 A1 | 7/2009 | Wu et al. |
| 2009/0181831 A1 | 7/2009 | Kuo |
| 2009/0181833 A1 | 7/2009 | Cassidy |
| 2009/0191988 A1 | 7/2009 | Klein |
| 2009/0192391 A1 | 7/2009 | Lovitt et al. |
| 2009/0192871 A1 | 7/2009 | Deacon et al. |
| 2009/0193344 A1 | 7/2009 | Smyers |
| 2009/0195350 A1 | 8/2009 | Tsern et al. |
| 2009/0197739 A1 | 8/2009 | Hashimoto |
| 2009/0197740 A1 | 8/2009 | Julskjaer et al. |
| 2009/0204422 A1 | 8/2009 | James |
| 2009/0204668 A1 | 8/2009 | Huang |
| 2009/0205482 A1 | 8/2009 | Shirai et al. |
| 2009/0209393 A1 | 8/2009 | Crater et al. |
| 2009/0210078 A1 | 8/2009 | Crowley |
| 2009/0216629 A1 | 8/2009 | James |
| 2009/0217178 A1 | 8/2009 | Niyogi et al. |
| 2009/0221404 A1 | 9/2009 | Dorogusker et al. |
| 2009/0221405 A1 | 9/2009 | Wang |
| 2009/0221407 A1 | 9/2009 | Hauk |
| 2009/0227424 A1 | 9/2009 | Hirata et al. |
| 2009/0227429 A1 | 9/2009 | Baudhuin |
| 2009/0227432 A1 | 9/2009 | Pacheco |
| 2009/0232420 A1 | 9/2009 | Eisenberg et al. |
| 2009/0233769 A1 | 9/2009 | Pryor |
| 2009/0233771 A1 | 9/2009 | Quatrochi et al. |
| 2009/0238400 A1 | 9/2009 | Im |
| 2009/0239714 A1 | 9/2009 | Sellers |
| 2009/0246746 A1 | 10/2009 | Roerdink |
| 2009/0247366 A1 | 10/2009 | Frumer |
| 2009/0253109 A1 | 10/2009 | Anvari |
| 2009/0253554 A1 | 10/2009 | Mcintosh |
| 2009/0257323 A1 | 10/2009 | Soltani |
| 2009/0258710 A1 | 10/2009 | Quatrochi et al. |
| 2009/0258758 A1 | 10/2009 | Hickman |
| 2009/0258763 A1 | 10/2009 | Richter |
| 2009/0262088 A1 | 10/2009 | Moll-Carrillo et al. |
| 2009/0263772 A1 | 10/2009 | Root |
| 2009/0264258 A1 | 10/2009 | Lo |
| 2009/0264260 A1 | 10/2009 | Piaget et al. |
| 2009/0265649 A1 | 10/2009 | Schlossberg et al. |
| 2009/0267783 A1 | 10/2009 | Vock et al. |
| 2009/0269728 A1 | 10/2009 | Verstegen et al. |
| 2009/0270226 A1 | 10/2009 | Watterson |
| 2009/0270743 A1 | 10/2009 | Dugan |
| 2009/0278707 A1 | 11/2009 | Biggins et al. |
| 2009/0280964 A1 | 11/2009 | Lin |
| 2009/0282080 A1 | 11/2009 | Schlossberg et al. |
| 2009/0286653 A1 | 11/2009 | Wiber |
| 2009/0286654 A1 | 11/2009 | Rice |
| 2009/0288887 A1 | 11/2009 | Chen |
| 2009/0292178 A1 | 11/2009 | Ellis et al. |
| 2009/0293319 A1 | 12/2009 | Avni |
| 2009/0298649 A1 | 12/2009 | Dyer et al. |
| 2009/0308179 A1* | 12/2009 | Wyatt ................ A61B 5/0002 73/862.391 |
| 2009/0309891 A1 | 12/2009 | Karkanias et al. |
| 2009/0312151 A1 | 12/2009 | Thieberger |
| 2009/0312158 A1 | 12/2009 | Trevino et al. |
| 2009/0312658 A1 | 12/2009 | Thieberger |
| 2010/0003647 A1 | 1/2010 | Brown et al. |
| 2010/0009809 A1 | 1/2010 | Carrington |
| 2010/0009810 A1 | 1/2010 | Trzecieski |
| 2010/0015585 A1 | 1/2010 | Baker |
| 2010/0016127 A1 | 1/2010 | Farnsworth et al. |
| 2010/0016742 A1 | 1/2010 | James |
| 2010/0017402 A1 | 1/2010 | Fleming et al. |
| 2010/0019593 A1 | 1/2010 | Ritchey |
| 2010/0022354 A1 | 1/2010 | Fisher |
| 2010/0024590 A1* | 2/2010 | O'Neill ................ G01L 3/242 74/594.1 |
| 2010/0031803 A1 | 2/2010 | Lozada et al. |
| 2010/0032533 A1 | 2/2010 | Chen et al. |
| 2010/0034665 A1 | 2/2010 | Zhong et al. |
| 2010/0035726 A1 | 2/2010 | Fisher et al. |
| 2010/0036736 A1 | 2/2010 | McGee et al. |
| 2010/0038149 A1 | 2/2010 | Corel |
| 2010/0041000 A1 | 2/2010 | Glass |
| 2010/0041516 A1 | 2/2010 | Kodama |
| 2010/0048358 A1 | 2/2010 | Tchao et al. |
| 2010/0050082 A1 | 2/2010 | Katz et al. |
| 2010/0056339 A1 | 3/2010 | Chen |
| 2010/0056340 A1 | 3/2010 | Ellis |
| 2010/0056876 A1 | 3/2010 | Ellis |
| 2010/0062818 A1 | 3/2010 | Haughay, Jr. et al. |
| 2010/0062904 A1 | 3/2010 | Crawford et al. |
| 2010/0062914 A1 | 3/2010 | Splane |
| 2010/0063426 A1 | 3/2010 | Planke |
| 2010/0064255 A1 | 3/2010 | Rottler et al. |
| 2010/0068684 A1 | 3/2010 | Sabel |
| 2010/0069202 A1 | 3/2010 | Olsen |
| 2010/0075812 A1 | 3/2010 | Piaget et al. |
| 2010/0076278 A1 | 3/2010 | van der Zande et al. |
| 2010/0077564 A1 | 4/2010 | Saier et al. |
| 2010/0079291 A1 | 4/2010 | Kroll et al. |
| 2010/0081116 A1 | 4/2010 | Barasch et al. |
| 2010/0081548 A1 | 4/2010 | Labedz |
| 2010/0087298 A1 | 4/2010 | Zaccherini |
| 2010/0087701 A1 | 4/2010 | Berka et al. |
| 2010/0088023 A1 | 4/2010 | Werner |
| 2010/0093492 A1 | 4/2010 | Watterson et al. |
| 2010/0093493 A1 | 4/2010 | Eldridge |
| 2010/0099437 A1 | 4/2010 | Moerdijk |
| 2010/0099541 A1 | 4/2010 | Patel |
| 2010/0099954 A1 | 4/2010 | Dickinson et al. |
| 2010/0105527 A1 | 4/2010 | Johnson |
| 2010/0112536 A1 | 5/2010 | Claassen et al. |
| 2010/0113222 A1 | 5/2010 | Radow |
| 2010/0113223 A1 | 5/2010 | Chiles et al. |
| 2010/0113948 A1 | 5/2010 | Yang et al. |
| 2010/0120585 A1 | 5/2010 | Quy et al. |
| 2010/0125026 A1 | 5/2010 | Zavadsky et al. |
| 2010/0125029 A1 | 5/2010 | Nielson et al. |
| 2010/0125183 A1 | 5/2010 | Vayalattu et al. |
| 2010/0130337 A1 | 5/2010 | Stewart |
| 2010/0137049 A1 | 6/2010 | Epstein |
| 2010/0137105 A1 | 6/2010 | McLaughlin |
| 2010/0137106 A1 | 6/2010 | Oshima et al. |
| 2010/0144501 A1 | 6/2010 | Berhanu |
| 2010/0146055 A1 | 6/2010 | Hannuksela |
| 2010/0152546 A1 | 6/2010 | Behan et al. |
| 2010/0156625 A1 | 6/2010 | Ruha |
| 2010/0156760 A1 | 6/2010 | Cheswick |
| 2010/0160013 A1 | 6/2010 | Sanders |
| 2010/0160014 A1 | 6/2010 | Galasso et al. |
| 2010/0160115 A1 | 6/2010 | Morris et al. |
| 2010/0164579 A1 | 7/2010 | Acatrinei |
| 2010/0167801 A1 | 7/2010 | Karkanias et al. |
| 2010/0167876 A1 | 7/2010 | Cheng |
| 2010/0167883 A1 | 7/2010 | Grind |
| 2010/0173276 A1 | 7/2010 | Vasin |
| 2010/0173755 A1 | 7/2010 | De Lazarraga |
| 2010/0175634 A1 | 7/2010 | Chang et al. |
| 2010/0179035 A1 | 7/2010 | Carnahan |
| 2010/0179883 A1 | 7/2010 | Devolites |
| 2010/0182436 A1 | 7/2010 | Boman et al. |
| 2010/0184565 A1 | 7/2010 | Avellino |

(56) References Cited

U.S. PATENT DOCUMENTS

| | | |
|---|---|---|
| 2010/0184568 A1 | 7/2010 | Schippers |
| 2010/0188405 A1 | 7/2010 | Haughay, Jr. et al. |
| 2010/0190610 A1 | 7/2010 | Pryor |
| 2010/0190615 A1 | 7/2010 | Baker et al. |
| 2010/0191462 A1 | 7/2010 | Kobuya et al. |
| 2010/0192715 A1 | 8/2010 | Vauchel et al. |
| 2010/0197462 A1 | 8/2010 | Piane, Jr. |
| 2010/0197465 A1 | 8/2010 | Stevenson |
| 2010/0204013 A1 | 8/2010 | Chen |
| 2010/0208038 A1 | 8/2010 | Kutliroff et al. |
| 2010/0208082 A1 | 8/2010 | Buchner et al. |
| 2010/0210418 A1 | 8/2010 | Park |
| 2010/0211439 A1 | 8/2010 | Marci et al. |
| 2010/0216536 A1 | 8/2010 | Gagner |
| 2010/0216599 A1 | 8/2010 | Watterson |
| 2010/0216600 A1 | 8/2010 | Noffsinger |
| 2010/0216603 A1 | 8/2010 | Somers |
| 2010/0216607 A1 | 8/2010 | Mueller |
| 2010/0217096 A1 | 8/2010 | Nanikashvili |
| 2010/0217099 A1 | 8/2010 | Leboeuf |
| 2010/0217102 A1 | 8/2010 | LeBoeuf et al. |
| 2010/0222165 A1 | 9/2010 | Nurnberg et al. |
| 2010/0222178 A1 | 9/2010 | Shea |
| 2010/0222179 A1 | 9/2010 | Temple et al. |
| 2010/0222182 A1 | 9/2010 | Park |
| 2010/0227542 A1 | 9/2010 | Goldmann |
| 2010/0227740 A1 | 9/2010 | Liu |
| 2010/0234184 A1 | 9/2010 | Le Page |
| 2010/0234693 A1 | 9/2010 | Srinivasan et al. |
| 2010/0235667 A1 | 9/2010 | Mucignat et al. |
| 2010/0240458 A1 | 9/2010 | Gaiba et al. |
| 2010/0240495 A1 | 9/2010 | Law |
| 2010/0240945 A1 | 9/2010 | Bikko |
| 2010/0241018 A1 | 9/2010 | Vogel |
| 2010/0243514 A1 | 9/2010 | Samain et al. |
| 2010/0247081 A1 | 9/2010 | Victoria Pons |
| 2010/0248899 A1 | 9/2010 | Bedell et al. |
| 2010/0248900 A1 | 9/2010 | Ashby |
| 2010/0248901 A1 | 9/2010 | Martens |
| 2010/0251454 A1 | 10/2010 | Kiernan |
| 2010/0255884 A1 | 10/2010 | Konkka et al. |
| 2010/0255955 A1 | 10/2010 | Hickman |
| 2010/0255959 A1 | 10/2010 | Dalebout et al. |
| 2010/0255965 A1 | 10/2010 | Chen |
| 2010/0259043 A1 | 10/2010 | Balsamo |
| 2010/0261580 A1 | 10/2010 | Lannon |
| 2010/0267524 A1 | 10/2010 | Stewart et al. |
| 2010/0271367 A1 | 10/2010 | Vaden et al. |
| 2010/0273610 A1 | 10/2010 | Johnson |
| 2010/0274100 A1 | 10/2010 | Behar |
| 2010/0279822 A1 | 11/2010 | Ford |
| 2010/0279823 A1 | 11/2010 | Waters |
| 2010/0281463 A1 | 11/2010 | Estrade |
| 2010/0283601 A1 | 11/2010 | Tai et al. |
| 2010/0285933 A1 | 11/2010 | Nalley |
| 2010/0289466 A1 | 11/2010 | Telefus |
| 2010/0289772 A1 | 11/2010 | Miller |
| 2010/0292050 A1* | 11/2010 | DiBenedetto ...... A63B 24/0062 482/9 |
| 2010/0292599 A1 | 11/2010 | Oleson et al. |
| 2010/0292600 A1 | 11/2010 | Dibenedetto et al. |
| 2010/0298098 A1 | 11/2010 | Ercan |
| 2010/0298655 A1 | 11/2010 | McCombie et al. |
| 2010/0298656 A1 | 11/2010 | McCombie et al. |
| 2010/0298661 A1 | 11/2010 | McCombie et al. |
| 2010/0300272 A1 | 12/2010 | Scherf |
| 2010/0302142 A1 | 12/2010 | French |
| 2010/0302250 A1 | 12/2010 | Hoebel |
| 2010/0304931 A1 | 12/2010 | Stumpf |
| 2010/0304932 A1 | 12/2010 | Kolman et al. |
| 2010/0311552 A1 | 12/2010 | Sumners |
| 2010/0312596 A1 | 12/2010 | Saffari et al. |
| 2010/0320956 A1 | 12/2010 | Lumsden et al. |
| 2010/0324387 A1 | 12/2010 | Moon |
| 2010/0327603 A1 | 12/2010 | Suaan |
| 2011/0003663 A1 | 1/2011 | Chiu et al. |
| 2011/0003664 A1 | 1/2011 | Richard |
| 2011/0009240 A1 | 1/2011 | Chiu et al. |
| 2011/0009249 A1 | 1/2011 | Campanaro et al. |
| 2011/0015039 A1 | 1/2011 | Shea |
| 2011/0015041 A1 | 1/2011 | Shea |
| 2011/0015468 A1 | 1/2011 | Aarts et al. |
| 2011/0021319 A1 | 1/2011 | Nissila et al. |
| 2011/0021323 A1 | 1/2011 | Wu |
| 2011/0021953 A1 | 1/2011 | Sanematsu et al. |
| 2011/0028277 A1 | 2/2011 | Merli |
| 2011/0028282 A1 | 2/2011 | Sbragia |
| 2011/0032105 A1 | 2/2011 | Hoffman et al. |
| 2011/0034300 A1 | 2/2011 | Hall |
| 2011/0039659 A1 | 2/2011 | Kim et al. |
| 2011/0046519 A1 | 2/2011 | Raheman |
| 2011/0053131 A1 | 3/2011 | Regnier |
| 2011/0054242 A1 | 3/2011 | Bender |
| 2011/0054270 A1 | 3/2011 | Derchak |
| 2011/0054272 A1 | 3/2011 | Derchak |
| 2011/0054359 A1* | 3/2011 | Sazonov ............... A43B 3/0005 600/595 |
| 2011/0054809 A1 | 3/2011 | Templeman |
| 2011/0056328 A1 | 3/2011 | Ko |
| 2011/0061515 A1 | 3/2011 | Turner |
| 2011/0061840 A1 | 3/2011 | Goldmann |
| 2011/0063114 A1 | 3/2011 | Ikoyan |
| 2011/0065371 A1 | 3/2011 | Leff |
| 2011/0065373 A1 | 3/2011 | Goldmann |
| 2011/0066056 A1 | 3/2011 | Huang |
| 2011/0067361 A1 | 3/2011 | Sloan |
| 2011/0072955 A1 | 3/2011 | Turner |
| 2011/0073743 A1 | 3/2011 | Shamie |
| 2011/0075835 A1 | 3/2011 | Hill |
| 2011/0077055 A1 | 3/2011 | Pakula et al. |
| 2011/0082006 A1 | 4/2011 | Ishii |
| 2011/0082007 A1 | 4/2011 | Birrell |
| 2011/0082010 A1 | 4/2011 | Dyer |
| 2011/0082013 A1 | 4/2011 | Bastian |
| 2011/0082015 A1 | 4/2011 | Dreissigacker et al. |
| 2011/0082397 A1 | 4/2011 | Alberts |
| 2011/0086707 A1 | 4/2011 | Loveland |
| 2011/0087076 A1 | 4/2011 | Brynelsen et al. |
| 2011/0087137 A1 | 4/2011 | Hanoun |
| 2011/0087445 A1 | 4/2011 | Sobolewski |
| 2011/0087446 A1* | 4/2011 | Redmond ............... A61B 5/221 702/44 |
| 2011/0090092 A1 | 4/2011 | Birrell et al. |
| 2011/0091842 A1 | 4/2011 | Dugan |
| 2011/0092779 A1 | 4/2011 | Chang et al. |
| 2011/0093100 A1 | 4/2011 | Ramsay |
| 2011/0096764 A1 | 4/2011 | Tunioli et al. |
| 2011/0098157 A1 | 4/2011 | Whalen et al. |
| 2011/0098615 A1 | 4/2011 | Whalen et al. |
| 2011/0105278 A1 | 5/2011 | Fabbri |
| 2011/0105279 A1 | 5/2011 | Herranen |
| 2011/0105920 A1 | 5/2011 | Haataja |
| 2011/0106597 A1 | 5/2011 | Ferdman et al. |
| 2011/0109283 A1 | 5/2011 | Kapels et al. |
| 2011/0112771 A1 | 5/2011 | French |
| 2011/0117529 A1 | 5/2011 | Barash |
| 2011/0118084 A1 | 5/2011 | Tsai et al. |
| 2011/0118086 A1 | 5/2011 | Radow |
| 2011/0118089 A1 | 5/2011 | Ellis |
| 2011/0124466 A1 | 5/2011 | Nishimura |
| 2011/0124469 A1 | 5/2011 | Uhlir |
| 2011/0124476 A1 | 5/2011 | Holley |
| 2011/0124978 A1 | 5/2011 | Williams |
| 2011/0125063 A1 | 5/2011 | Shalon et al. |
| 2011/0131005 A1 | 6/2011 | Ueshima et al. |
| 2011/0136627 A1 | 6/2011 | Williams |
| 2011/0140904 A1 | 6/2011 | Kashi |
| 2011/0143769 A1 | 6/2011 | Jones et al. |
| 2011/0143898 A1 | 6/2011 | Trees |
| 2011/0152032 A1 | 6/2011 | Barnett |
| 2011/0152033 A1 | 6/2011 | Yang |
| 2011/0152037 A1 | 6/2011 | Yeong-Haw Tsou |
| 2011/0152038 A1 | 6/2011 | Freitag |
| 2011/0152039 A1 | 6/2011 | Hendrickson et al. |

(56) References Cited

U.S. PATENT DOCUMENTS

| | | |
|---|---|---|
| 2011/0152635 A1 | 6/2011 | Morris et al. |
| 2011/0152696 A1 | 6/2011 | Ryan |
| 2011/0163939 A1 | 7/2011 | Tam et al. |
| 2011/0164044 A1 | 7/2011 | Huang |
| 2011/0164175 A1 | 7/2011 | Chung et al. |
| 2011/0165995 A1 | 7/2011 | Paulus |
| 2011/0165996 A1 | 7/2011 | Paulus |
| 2011/0165997 A1 | 7/2011 | Reich |
| 2011/0165998 A1 | 7/2011 | Lau et al. |
| 2011/0167447 A1 | 7/2011 | Wong |
| 2011/0172058 A1 | 7/2011 | Deaconu |
| 2011/0172059 A1 | 7/2011 | Watterson et al. |
| 2011/0172060 A1 | 7/2011 | Morales et al. |
| 2011/0175989 A1 | 7/2011 | Islam |
| 2011/0176943 A1 | 7/2011 | Tran et al. |
| 2011/0177919 A1 | 7/2011 | Tamari |
| 2011/0179068 A1 | 7/2011 | O'brien |
| 2011/0181420 A1 | 7/2011 | Mack et al. |
| 2011/0183307 A1 | 7/2011 | Shum et al. |
| 2011/0184225 A1 | 7/2011 | Whitall et al. |
| 2011/0184247 A1 | 7/2011 | Contant et al. |
| 2011/0188269 A1 | 8/2011 | Hosotani |
| 2011/0188668 A1 | 8/2011 | Donaldson |
| 2011/0191123 A1 | 8/2011 | Buzynski |
| 2011/0195819 A1 | 8/2011 | Shaw |
| 2011/0197157 A1 | 8/2011 | Hoffman et al. |
| 2011/0199393 A1 | 8/2011 | Nurse et al. |
| 2011/0199799 A1 | 8/2011 | Hui et al. |
| 2011/0201476 A1 | 8/2011 | Solomon |
| 2011/0201481 A1 | 8/2011 | Lo |
| 2011/0205164 A1 | 8/2011 | Hansen et al. |
| 2011/0214148 A1 | 9/2011 | Gossweiler, III et al. |
| 2011/0218086 A1 | 9/2011 | Boren |
| 2011/0221672 A1 | 9/2011 | Osterhout et al. |
| 2011/0222375 A1 | 9/2011 | Tsubata et al. |
| 2011/0224057 A1 | 9/2011 | Wu |
| 2011/0224498 A1 | 9/2011 | Banet et al. |
| 2011/0229862 A1 | 9/2011 | Parikh |
| 2011/0230732 A1 | 9/2011 | Edman et al. |
| 2011/0237396 A1 | 9/2011 | Lu |
| 2011/0237399 A1 | 9/2011 | Toback |
| 2011/0238217 A1 | 9/2011 | Kume |
| 2011/0245633 A1 | 10/2011 | Goldberg et al. |
| 2011/0247530 A1 | 10/2011 | Coffman |
| 2011/0251021 A1 | 10/2011 | Zavadsky et al. |
| 2011/0252597 A1 | 10/2011 | Burris et al. |
| 2011/0256988 A1 | 10/2011 | Weier |
| 2011/0257797 A1 | 10/2011 | Burris et al. |
| 2011/0263384 A1 | 10/2011 | Drazan |
| 2011/0263385 A1 | 10/2011 | Shea |
| 2011/0264305 A1 | 10/2011 | Choe |
| 2011/0267196 A1 | 11/2011 | Hu et al. |
| 2011/0269517 A1 | 11/2011 | Englert et al. |
| 2011/0269604 A1 | 11/2011 | Tseng |
| 2011/0270135 A1 | 11/2011 | Dooley |
| 2011/0275482 A1 | 11/2011 | Brodess et al. |
| 2011/0275489 A1 | 11/2011 | Apau |
| 2011/0275499 A1 | 11/2011 | Eschenbach |
| 2011/0276312 A1 | 11/2011 | Shalon et al. |
| 2011/0281691 A1 | 11/2011 | Ellis |
| 2011/0283188 A1 | 11/2011 | Farrenkopf et al. |
| 2011/0283231 A1 | 11/2011 | Richstein et al. |
| 2011/0295083 A1 | 12/2011 | Doelling et al. |
| 2011/0308919 A1 | 12/2011 | Hahn |
| 2011/0311955 A1 | 12/2011 | Forsten et al. |
| 2011/0312473 A1 | 12/2011 | Chu et al. |
| 2011/0319229 A1 | 12/2011 | Corbalis et al. |
| 2011/0320380 A1 | 12/2011 | Zahn et al. |
| 2012/0004074 A1 | 1/2012 | Schelzig |
| 2012/0004075 A1 | 1/2012 | Kissel et al. |
| 2012/0004076 A1 | 1/2012 | Fenster |
| 2012/0004080 A1 | 1/2012 | Webb |
| 2012/0010053 A1 | 1/2012 | Bayerlein et al. |
| 2012/0015778 A1 | 1/2012 | Lee et al. |
| 2012/0015779 A1 | 1/2012 | Powch et al. |
| 2012/0015784 A1 | 1/2012 | Reed |
| 2012/0020135 A1 | 1/2012 | McCune |
| 2012/0021873 A1 | 1/2012 | Brunner |
| 2012/0021875 A1 | 1/2012 | Karl |
| 2012/0024237 A1 | 2/2012 | Rice |
| 2012/0028761 A1 | 2/2012 | Dorogusker et al. |
| 2012/0029666 A1 | 2/2012 | Crowley et al. |
| 2012/0032896 A1 | 2/2012 | Vesely |
| 2012/0035487 A1 | 2/2012 | Werner et al. |
| 2012/0036557 A1 | 2/2012 | Li |
| 2012/0046144 A1 | 2/2012 | Lin et al. |
| 2012/0050818 A1 | 3/2012 | Watanabe |
| 2012/0055718 A1 | 3/2012 | Chen |
| 2012/0065031 A1 | 3/2012 | Buzzanco |
| 2012/0071301 A1 | 3/2012 | Kaylor et al. |
| 2012/0078127 A1 | 3/2012 | McDonald et al. |
| 2012/0079429 A1 | 3/2012 | Stathacopoulos et al. |
| 2012/0079529 A1 | 3/2012 | Harris et al. |
| 2012/0081531 A1 | 4/2012 | DeAngelis et al. |
| 2012/0083669 A1 | 4/2012 | Abujbara |
| 2012/0083705 A1 | 4/2012 | Yuen et al. |
| 2012/0084807 A1 | 4/2012 | Thompson et al. |
| 2012/0084811 A1 | 4/2012 | Thompson |
| 2012/0084812 A1 | 4/2012 | Thompson et al. |
| 2012/0088633 A1 | 4/2012 | Crafton |
| 2012/0088634 A1 | 4/2012 | Heidecke |
| 2012/0088640 A1 | 4/2012 | Wissink |
| 2012/0090446 A1 | 4/2012 | Moreno |
| 2012/0092327 A1 | 4/2012 | Adhikari |
| 2012/0096357 A1 | 4/2012 | Folgner et al. |
| 2012/0096405 A1 | 4/2012 | Seo |
| 2012/0105867 A1 | 5/2012 | Komatsu |
| 2012/0108914 A1 | 5/2012 | Bravomalo |
| 2012/0113029 A1 | 5/2012 | Ye et al. |
| 2012/0115695 A1 | 5/2012 | Watterson et al. |
| 2012/0116550 A1 | 5/2012 | Hoffman et al. |
| 2012/0116684 A1 | 5/2012 | Ingrassia et al. |
| 2012/0116806 A1 | 5/2012 | Stark et al. |
| 2012/0122063 A1 | 5/2012 | Chen et al. |
| 2012/0125559 A1 | 5/2012 | Fadell et al. |
| 2012/0129139 A1 | 5/2012 | Partovi |
| 2012/0132877 A1 | 5/2012 | Wang |
| 2012/0133192 A1 | 5/2012 | Simpson |
| 2012/0143358 A1 | 6/2012 | Adams et al. |
| 2012/0149996 A1 | 6/2012 | Stivoric et al. |
| 2012/0153015 A1 | 6/2012 | Gomez et al. |
| 2012/0157265 A1 | 6/2012 | Kao |
| 2012/0159563 A1 | 6/2012 | Gomez et al. |
| 2012/0165162 A1 | 6/2012 | Lu |
| 2012/0165703 A1 | 6/2012 | Bottum |
| 2012/0169603 A1 | 7/2012 | Peterson et al. |
| 2012/0174608 A1 | 7/2012 | Kumamoto et al. |
| 2012/0174833 A1 | 7/2012 | Early |
| 2012/0178590 A1 | 7/2012 | Lu |
| 2012/0178591 A1 | 7/2012 | Remelius |
| 2012/0179278 A1 | 7/2012 | Riley et al. |
| 2012/0187012 A1 | 7/2012 | TeVault et al. |
| 2012/0190502 A1 | 7/2012 | Paulus et al. |
| 2012/0190504 A1 | 7/2012 | Lee et al. |
| 2012/0202656 A1 | 8/2012 | Dorsay |
| 2012/0208153 A1 | 8/2012 | Bolla et al. |
| 2012/0212505 A1 | 8/2012 | Burroughs et al. |
| 2012/0214590 A1 | 8/2012 | Newhouse et al. |
| 2012/0217758 A1 | 8/2012 | Chen |
| 2012/0218184 A1 | 8/2012 | Wissmar |
| 2012/0225412 A1 | 9/2012 | Wagner |
| 2012/0228385 A1 | 9/2012 | Deluca |
| 2012/0230504 A1 | 9/2012 | Kuroda |
| 2012/0233002 A1 | 9/2012 | Abujbara |
| 2012/0237906 A9 | 9/2012 | Glass |
| 2012/0237911 A1 | 9/2012 | Watterson |
| 2012/0238800 A1 | 9/2012 | Naujokat et al. |
| 2012/0238851 A1 | 9/2012 | Kamen et al. |
| 2012/0242774 A1 | 9/2012 | Numano et al. |
| 2012/0248263 A1 | 10/2012 | Grotenhuis |
| 2012/0251983 A1 | 10/2012 | Golden |
| 2012/0252580 A1 | 10/2012 | Dugan |
| 2012/0253234 A1 | 10/2012 | Yang et al. |
| 2012/0253487 A1 | 10/2012 | Dugan |

(56) References Cited

U.S. PATENT DOCUMENTS

| | | |
|---|---|---|
| 2012/0253489 A1 | 10/2012 | Dugan |
| 2012/0258433 A1 | 10/2012 | Hope et al. |
| 2012/0263892 A1 | 10/2012 | Rodgers |
| 2012/0268592 A1 | 10/2012 | Aragones et al. |
| 2012/0270705 A1 | 10/2012 | Lo |
| 2012/0271121 A1 | 10/2012 | Della Torre et al. |
| 2012/0271143 A1 | 10/2012 | Aragones et al. |
| 2012/0277040 A1 | 11/2012 | Vincent et al. |
| 2012/0277891 A1 | 11/2012 | Aragones et al. |
| 2012/0285986 A1 | 11/2012 | Irvin |
| 2012/0290109 A1 | 11/2012 | Engelberg et al. |
| 2012/0293141 A1 | 11/2012 | Zhang et al. |
| 2012/0295764 A1 | 11/2012 | Brammer |
| 2012/0296455 A1 | 11/2012 | Ohnemus et al. |
| 2012/0298017 A1 | 11/2012 | Chen |
| 2012/0300515 A1 | 11/2012 | Carletti et al. |
| 2012/0302408 A1 | 11/2012 | Burger |
| 2012/0306643 A1 | 12/2012 | Dugan |
| 2012/0313776 A1 | 12/2012 | Utter, II |
| 2012/0315986 A1 | 12/2012 | Walling |
| 2012/0315987 A1 | 12/2012 | Walling |
| 2012/0316406 A1 | 12/2012 | Rahman et al. |
| 2012/0316455 A1 | 12/2012 | Rahman et al. |
| 2012/0316456 A1 | 12/2012 | Rahman et al. |
| 2012/0316458 A1 | 12/2012 | Rahman et al. |
| 2012/0317024 A1 | 12/2012 | Rahman et al. |
| 2012/0319604 A1 | 12/2012 | Walters |
| 2012/0322628 A1 | 12/2012 | Gautier |
| 2012/0323496 A1 | 12/2012 | Burroughs |
| 2012/0326873 A1 | 12/2012 | Utter, II |
| 2012/0329027 A1 | 12/2012 | Lewolt |
| 2012/0329611 A1 | 12/2012 | Bouchard |
| 2013/0002533 A1 | 1/2013 | Burroughs et al. |
| 2013/0004010 A1 | 1/2013 | Royer |
| 2013/0009993 A1 | 1/2013 | Horseman |
| 2013/0011818 A1 | 1/2013 | Shum et al. |
| 2013/0014155 A1 | 1/2013 | Clarke et al. |
| 2013/0015945 A1 | 1/2013 | Chang |
| 2013/0017888 A1 | 1/2013 | King et al. |
| 2013/0017929 A1 | 1/2013 | Hendrickson et al. |
| 2013/0018494 A1 | 1/2013 | Amini |
| 2013/0018668 A1 | 1/2013 | Goldberg et al. |
| 2013/0029807 A1 | 1/2013 | Amsel |
| 2013/0034671 A1 | 2/2013 | George |
| 2013/0035209 A1 | 2/2013 | Gilley et al. |
| 2013/0035612 A1 | 2/2013 | Mason et al. |
| 2013/0040271 A1 | 2/2013 | Rytky et al. |
| 2013/0040783 A1 | 2/2013 | Duda et al. |
| 2013/0041590 A1 | 2/2013 | Burich et al. |
| 2013/0041617 A1 | 2/2013 | Pease et al. |
| 2013/0044521 A1 | 2/2013 | Zhao et al. |
| 2013/0050973 A1 | 2/2013 | Rohrbach |
| 2013/0053218 A1 | 2/2013 | Barker |
| 2013/0053222 A1 | 2/2013 | Lo |
| 2013/0053717 A1 | 2/2013 | Vandine et al. |
| 2013/0053990 A1 | 2/2013 | Ackland |
| 2013/0065680 A1 | 3/2013 | Zavadsky |
| 2013/0073093 A1 | 3/2013 | Songkakul |
| 2013/0083003 A1 | 4/2013 | Perez et al. |
| 2013/0085038 A1 | 4/2013 | Fischer |
| 2013/0090565 A1 | 4/2013 | Quy |
| 2013/0092647 A1 | 4/2013 | Chen |
| 2013/0095959 A1 | 4/2013 | Marty |
| 2013/0095978 A1 | 4/2013 | Sauter |
| 2013/0097635 A1 | 4/2013 | Yerli |
| 2013/0105565 A1 | 5/2013 | Kamprath |
| 2013/0106684 A1 | 5/2013 | Weast et al. |
| 2013/0108995 A1 | 5/2013 | DePasqua et al. |
| 2013/0116091 A1 | 5/2013 | Fritz |
| 2013/0116092 A1 | 5/2013 | Martinez et al. |
| 2013/0116095 A1 | 5/2013 | Hsieh |
| 2013/0116514 A1 | 5/2013 | Kroner et al. |
| 2013/0123073 A1 | 5/2013 | Olson et al. |
| 2013/0127636 A1 | 5/2013 | Aryanpur et al. |
| 2013/0129217 A1 | 5/2013 | Gupta |
| 2013/0130868 A1 | 5/2013 | Hou |
| 2013/0130869 A1 | 5/2013 | Hou |
| 2013/0135115 A1 | 5/2013 | Johnson et al. |
| 2013/0137552 A1 | 5/2013 | Kemp et al. |
| 2013/0139736 A1 | 6/2013 | Flaherty |
| 2013/0141235 A1 | 6/2013 | Utter, II |
| 2013/0143721 A1 | 6/2013 | Dalebout |
| 2013/0144464 A1 | 6/2013 | Dorogusker et al. |
| 2013/0147411 A1 | 6/2013 | Pang et al. |
| 2013/0148861 A1 | 6/2013 | Ferlatte et al. |
| 2013/0150214 A1 | 6/2013 | Wu |
| 2013/0154441 A1* | 6/2013 | Redmond ............... G08G 1/02 310/319 |
| 2013/0158368 A1 | 6/2013 | Pacione et al. |
| 2013/0165195 A1 | 6/2013 | Watterson |
| 2013/0165297 A1 | 6/2013 | Daly |
| 2013/0172152 A1 | 7/2013 | Watterson |
| 2013/0173156 A1 | 7/2013 | Wither et al. |
| 2013/0174273 A1 | 7/2013 | Grab et al. |
| 2013/0177884 A1 | 7/2013 | Root |
| 2013/0178334 A1 | 7/2013 | Brammer |
| 2013/0182781 A1 | 7/2013 | Matsutani |
| 2013/0184843 A1 | 7/2013 | Ellis et al. |
| 2013/0185003 A1 | 7/2013 | Carbeck et al. |
| 2013/0190136 A1 | 7/2013 | Watterson |
| 2013/0190143 A1 | 7/2013 | Greenhill et al. |
| 2013/0190657 A1 | 7/2013 | Flaction et al. |
| 2013/0191034 A1 | 7/2013 | Weast et al. |
| 2013/0196821 A1 | 8/2013 | Watterson et al. |
| 2013/0196822 A1 | 8/2013 | Watterson et al. |
| 2013/0196826 A1 | 8/2013 | Colledge |
| 2013/0196827 A1 | 8/2013 | Chang |
| 2013/0203557 A1 | 8/2013 | Su |
| 2013/0203561 A1 | 8/2013 | Lee et al. |
| 2013/0208576 A1 | 8/2013 | Loree, IV et al. |
| 2013/0209972 A1 | 8/2013 | Carter et al. |
| 2013/0210578 A1 | 8/2013 | Birrell |
| 2013/0210581 A1 | 8/2013 | Watterson et al. |
| 2013/0210582 A1 | 8/2013 | Bkool |
| 2013/0211858 A1 | 8/2013 | Ohnemus et al. |
| 2013/0216982 A1 | 8/2013 | Bennett et al. |
| 2013/0216990 A1 | 8/2013 | Chu et al. |
| 2013/0228063 A1 | 9/2013 | Turner |
| 2013/0228422 A1 | 9/2013 | Mathieu |
| 2013/0231219 A1 | 9/2013 | Huang |
| 2013/0231226 A1 | 9/2013 | Bonutti |
| 2013/0231575 A1 | 9/2013 | Erkkila et al. |
| 2013/0233097 A1 | 9/2013 | Hayner |
| 2013/0237383 A1 | 9/2013 | Chen |
| 2013/0241696 A1 | 9/2013 | Fabrizio |
| 2013/0245966 A1 | 9/2013 | Burroughs et al. |
| 2013/0260965 A1 | 10/2013 | Chia et al. |
| 2013/0263418 A1 | 10/2013 | Johnson, Jr. |
| 2013/0267385 A1 | 10/2013 | Watterson et al. |
| 2013/0267386 A1 | 10/2013 | Her |
| 2013/0273509 A1 | 10/2013 | Mutti |
| 2013/0274040 A1 | 10/2013 | Coza et al. |
| 2013/0274067 A1 | 10/2013 | Watterson et al. |
| 2013/0274069 A1 | 10/2013 | Watterson et al. |
| 2013/0274071 A1 | 10/2013 | Wang |
| 2013/0274587 A1 | 10/2013 | Coza et al. |
| 2013/0274635 A1 | 10/2013 | Coza et al. |
| 2013/0274904 A1 | 10/2013 | Coza et al. |
| 2013/0280682 A1 | 10/2013 | Levine et al. |
| 2013/0282157 A1 | 10/2013 | Shin et al. |
| 2013/0282447 A1 | 10/2013 | Himanen et al. |
| 2013/0288223 A1 | 10/2013 | Watterson et al. |
| 2013/0289886 A1 | 10/2013 | Ricks |
| 2013/0289932 A1 | 10/2013 | Baechler |
| 2013/0290364 A1 | 10/2013 | Minvielle |
| 2013/0297642 A1 | 11/2013 | Minvielle |
| 2013/0298019 A1 | 11/2013 | Henderson |
| 2013/0303837 A1 | 11/2013 | Berka et al. |
| 2013/0310221 A1 | 11/2013 | Zuber |
| 2013/0310230 A1 | 11/2013 | Norris |
| 2013/0310658 A1 | 11/2013 | Ricks |
| 2013/0316830 A1 | 11/2013 | Sedzin et al. |
| 2013/0324368 A1 | 12/2013 | Aragones et al. |
| 2013/0325394 A1 | 12/2013 | Yuen et al. |

(56) References Cited

U.S. PATENT DOCUMENTS

| | | |
|---|---|---|
| 2013/0328416 A1 | 12/2013 | Whitworth et al. |
| 2013/0337974 A1 | 12/2013 | Yanev et al. |
| 2013/0337981 A1 | 12/2013 | Habing |
| 2013/0338802 A1 | 12/2013 | Winsper et al. |
| 2013/0345978 A1 | 12/2013 | Lush et al. |
| 2013/0346043 A1 | 12/2013 | Mewes et al. |
| 2014/0011645 A1 | 1/2014 | Johnson et al. |
| 2014/0026788 A1 | 1/2014 | Kallio, III et al. |
| 2014/0031174 A1 | 1/2014 | Huang |
| 2014/0031703 A1 | 1/2014 | Rayner et al. |
| 2014/0038781 A1 | 2/2014 | Foley |
| 2014/0039329 A1 | 2/2014 | Kampman et al. |
| 2014/0039840 A1 | 2/2014 | Yuen et al. |
| 2014/0045656 A1 | 2/2014 | Zhang |
| 2014/0052280 A1 | 2/2014 | Yuen et al. |
| 2014/0056461 A1 | 2/2014 | Afshar |
| 2014/0058806 A1 | 2/2014 | Guenette et al. |
| 2014/0063180 A1 | 3/2014 | Sharma |
| 2014/0066264 A1 | 3/2014 | Haddon |
| 2014/0069838 A1 | 3/2014 | Minvielle |
| 2014/0073488 A1 | 3/2014 | Wu |
| 2014/0074265 A1 | 3/2014 | Arginsky |
| 2014/0077494 A1 | 3/2014 | Sutkowski |
| 2014/0080678 A1 | 3/2014 | Wu |
| 2014/0085077 A1 | 3/2014 | Luna et al. |
| 2014/0087923 A1 | 3/2014 | Warren |
| 2014/0089836 A1 | 3/2014 | Damani et al. |
| 2014/0094941 A1 | 4/2014 | Ellis et al. |
| 2014/0099614 A1 | 4/2014 | Hu et al. |
| 2014/0100464 A1 | 4/2014 | Kaleal et al. |
| 2014/0102340 A1 | 4/2014 | Kooistra |
| 2014/0106322 A1 | 4/2014 | Durand |
| 2014/0113779 A1 | 4/2014 | Loach |
| 2014/0121066 A1 | 5/2014 | Huang et al. |
| 2014/0121471 A1 | 5/2014 | Walker |
| 2014/0125618 A1 | 5/2014 | Panther et al. |
| 2014/0129240 A1 | 5/2014 | Zhang |
| 2014/0134582 A1 | 5/2014 | Konishi |
| 2014/0135173 A1 | 5/2014 | Watterson |
| 2014/0135631 A1 | 5/2014 | Brumback et al. |
| 2014/0139450 A1 | 5/2014 | Levesque et al. |
| 2014/0141396 A1 | 5/2014 | Spratt |
| 2014/0142403 A1 | 5/2014 | Brumback et al. |
| 2014/0145935 A1 | 5/2014 | Sztuk |
| 2014/0147829 A1 | 5/2014 | Jerauld |
| 2014/0150042 A1 | 5/2014 | Pacor et al. |
| 2014/0156041 A1 | 6/2014 | Martin |
| 2014/0156084 A1 | 6/2014 | Rahman et al. |
| 2014/0156228 A1 | 6/2014 | Molettiere et al. |
| 2014/0156308 A1 | 6/2014 | Ohnemus et al. |
| 2014/0156645 A1 | 6/2014 | Brust et al. |
| 2014/0162230 A1 | 6/2014 | Akopian |
| 2014/0163429 A1 | 6/2014 | Tropper et al. |
| 2014/0164611 A1 | 6/2014 | Molettiere et al. |
| 2014/0171266 A1 | 6/2014 | Hawkins, III et al. |
| 2014/0171272 A1 | 6/2014 | Hawkins, III et al. |
| 2014/0172873 A1 | 6/2014 | Varoglu et al. |
| 2014/0173660 A1 | 6/2014 | Correa et al. |
| 2014/0180480 A1 | 6/2014 | Lee et al. |
| 2014/0187383 A1 | 7/2014 | Martin |
| 2014/0194260 A1 | 7/2014 | Campanaro et al. |
| 2014/0195103 A1* | 7/2014 | Nassef .............. B60L 11/007 701/31.5 |
| 2014/0197946 A1 | 7/2014 | Park et al. |
| 2014/0200691 A1 | 7/2014 | Lee et al. |
| 2014/0203943 A1 | 7/2014 | Kates |
| 2014/0205980 A1 | 7/2014 | Braier et al. |
| 2014/0206506 A1 | 7/2014 | Huang |
| 2014/0212857 A1 | 7/2014 | Sullivan et al. |
| 2014/0213416 A1 | 7/2014 | Wang |
| 2014/0214446 A1 | 7/2014 | Pera, Jr. |
| 2014/0220514 A1 | 8/2014 | Waldron et al. |
| 2014/0221160 A1 | 8/2014 | Hardy et al. |
| 2014/0221168 A1 | 8/2014 | Chen |
| 2014/0221784 A1 | 8/2014 | Pacione et al. |
| 2014/0221854 A1 | 8/2014 | Wai |
| 2014/0222173 A1 | 8/2014 | Giedwoyn et al. |
| 2014/0228118 A1 | 8/2014 | Hardy et al. |
| 2014/0228649 A1 | 8/2014 | Rayner et al. |
| 2014/0235411 A1 | 8/2014 | Dailey et al. |
| 2014/0249440 A1 | 9/2014 | Banet |
| 2014/0257535 A1 | 9/2014 | Morris et al. |
| 2014/0257537 A1 | 9/2014 | Stroupe et al. |
| 2014/0265072 A1 | 9/2014 | Chiu |
| 2014/0265690 A1 | 9/2014 | Henderson |
| 2014/0266939 A1 | 9/2014 | Baringer et al. |
| 2014/0270375 A1 | 9/2014 | Canavan et al. |
| 2014/0272894 A1 | 9/2014 | Grimes et al. |
| 2014/0273858 A1 | 9/2014 | Panther et al. |
| 2014/0274564 A1 | 9/2014 | Greenbaum |
| 2014/0274574 A1 | 9/2014 | Shorten et al. |
| 2014/0274579 A1 | 9/2014 | Olson |
| 2014/0275852 A1 | 9/2014 | Hong et al. |
| 2014/0275854 A1 | 9/2014 | Venkatraman et al. |
| 2014/0277637 A1 | 9/2014 | Ventura et al. |
| 2014/0278139 A1 | 9/2014 | Hong et al. |
| 2014/0278218 A1 | 9/2014 | Chang |
| 2014/0278220 A1 | 9/2014 | Yuen |
| 2014/0288390 A1 | 9/2014 | Hong et al. |
| 2014/0288438 A1 | 9/2014 | Venkatraman et al. |
| 2014/0288680 A1 | 9/2014 | Hoffman et al. |
| 2014/0308629 A1 | 10/2014 | Dugan |
| 2014/0309085 A1 | 10/2014 | Watterson et al. |
| 2014/0316192 A1 | 10/2014 | de Zambotti et al. |
| 2014/0335490 A1 | 11/2014 | Baarman et al. |
| 2014/0336796 A1 | 11/2014 | Agnew |
| 2014/0338120 A1 | 11/2014 | Baugh et al. |
| 2014/0349257 A1 | 11/2014 | Connor |
| 2014/0351150 A1 | 11/2014 | Ainsworth et al. |
| 2014/0358012 A1 | 12/2014 | Richards et al. |
| 2014/0358473 A1 | 12/2014 | Goel et al. |
| 2014/0360413 A1 | 12/2014 | Schenk |
| 2014/0363797 A1 | 12/2014 | Hu et al. |
| 2014/0363800 A1 | 12/2014 | Harris et al. |
| 2014/0371887 A1 | 12/2014 | Hoffman et al. |
| 2014/0380167 A1 | 12/2014 | Bloch et al. |
| 2015/0001048 A1 | 1/2015 | Koppes et al. |
| 2015/0003621 A1 | 1/2015 | Trammell |
| 2015/0004579 A1 | 1/2015 | Shelton |
| 2015/0004580 A1 | 1/2015 | Shum et al. |
| 2015/0011362 A1 | 1/2015 | Oh et al. |
| 2015/0016623 A1 | 1/2015 | Trammell |
| 2015/0018989 A1 | 1/2015 | Chen |
| 2015/0019135 A1 | 1/2015 | Kacyvenski et al. |
| 2015/0025660 A1 | 1/2015 | Prassler |
| 2015/0031964 A1 | 1/2015 | Bly et al. |
| 2015/0044648 A1 | 2/2015 | White et al. |
| 2015/0048807 A1 | 2/2015 | Fan et al. |
| 2015/0051051 A1 | 2/2015 | Liu et al. |
| 2015/0065273 A1 | 3/2015 | Lake |
| 2015/0065301 A1 | 3/2015 | Oteman |
| 2015/0079562 A1 | 3/2015 | Yeh et al. |
| 2015/0081209 A1 | 3/2015 | Yeh et al. |
| 2015/0081210 A1 | 3/2015 | Yeh et al. |
| 2015/0082408 A1 | 3/2015 | Yeh et al. |
| 2015/0087478 A1 | 3/2015 | Zhang et al. |
| 2015/0092972 A1 | 4/2015 | Lai et al. |
| 2015/0097700 A1 | 4/2015 | Holthouse |
| 2015/0099952 A1 | 4/2015 | Lain et al. |
| 2015/0105220 A1 | 4/2015 | Hong |
| 2015/0105881 A1 | 4/2015 | Guerrero et al. |
| 2015/0106868 A1 | 4/2015 | Lo |
| 2015/0118657 A1 | 4/2015 | Shrake et al. |
| 2015/0119197 A1 | 4/2015 | Liu |
| 2015/0126873 A1 | 5/2015 | Connor |
| 2015/0135284 A1 | 5/2015 | Bogard |
| 2015/0141202 A1 | 5/2015 | Ellis et al. |
| 2015/0151160 A1 | 6/2015 | Balakrishnan et al. |
| 2015/0154452 A1 | 6/2015 | Bentley et al. |
| 2015/0157918 A1 | 6/2015 | Tracy |
| 2015/0165269 A1 | 6/2015 | Herrala et al. |
| 2015/0168365 A1 | 6/2015 | Connor |
| 2015/0177083 A1 | 6/2015 | Redmond |
| 2015/0181314 A1 | 6/2015 | Swanson |

(56) References Cited

U.S. PATENT DOCUMENTS

| | | |
|---|---|---|
| 2015/0182782 A1 | 7/2015 | Cutler |
| 2015/0186609 A1 | 7/2015 | Utter, II |
| 2015/0190679 A1 | 7/2015 | Carbone |
| 2015/0192929 A1 | 7/2015 | Rihn et al. |
| 2015/0199494 A1 | 7/2015 | Koduri et al. |
| 2015/0201722 A1 | 7/2015 | Brouard |
| 2015/0202487 A1 | 7/2015 | Wu |
| 2015/0209610 A1 | 7/2015 | Dalebout et al. |
| 2015/0209617 A1 | 7/2015 | Hsiao |
| 2015/0214823 A1* | 7/2015 | Shastry ............... H02K 7/1876 320/107 |
| 2015/0224363 A1 | 8/2015 | Clark et al. |
| 2015/0238815 A1 | 8/2015 | Lee |
| 2015/0246751 A1 | 9/2015 | Spivack et al. |
| 2015/0248844 A1 | 9/2015 | Ellis et al. |
| 2015/0250304 A1 | 9/2015 | Dalebout |
| 2015/0250420 A1 | 9/2015 | Longinotti-Buitoni et al. |
| 2015/0251047 A1 | 9/2015 | Maaniitty |
| 2015/0251048 A1 | 9/2015 | Dalebout |
| 2015/0251055 A1 | 9/2015 | Ashby |
| 2015/0253210 A1 | 9/2015 | Ashby et al. |
| 2015/0255002 A1 | 9/2015 | Harris et al. |
| 2015/0258382 A1 | 9/2015 | Nolan et al. |
| 2015/0258384 A1 | 9/2015 | Suzuki |
| 2015/0262459 A1 | 9/2015 | Munro et al. |
| 2015/0265903 A1 | 9/2015 | Kolen et al. |
| 2015/0269354 A1 | 9/2015 | Klassen |
| 2015/0272262 A1 | 10/2015 | Escamilla |
| 2015/0272473 A1 | 10/2015 | Zafiroglu |
| 2015/0273272 A1 | 10/2015 | Wang |
| 2015/0288926 A1 | 10/2015 | Glass et al. |
| 2015/0290490 A1 | 10/2015 | Badarneh |
| 2015/0295397 A1 | 10/2015 | Lin et al. |
| 2015/0296020 A1 | 10/2015 | Granqvist et al. |
| 2015/0305961 A1 | 10/2015 | Broerman et al. |
| 2015/0306456 A1 | 10/2015 | Pasini et al. |
| 2015/0310062 A1 | 10/2015 | Wang et al. |
| 2015/0314184 A1 | 11/2015 | Moya Saez |
| 2015/0318015 A1 | 11/2015 | Bose et al. |
| 2015/0320588 A1 | 11/2015 | Connor |
| 2015/0324751 A1 | 11/2015 | Orenstein et al. |
| 2015/0327804 A1 | 11/2015 | Lefever et al. |
| 2015/0331449 A1 | 11/2015 | Ng |
| 2015/0335288 A1 | 11/2015 | Toth et al. |
| 2015/0335941 A1 | 11/2015 | Lo |
| 2015/0339946 A1 | 11/2015 | Pacione et al. |
| 2015/0342815 A1 | 12/2015 | Watson |
| 2015/0346994 A1 | 12/2015 | Chanyontpatanakul |
| 2015/0351690 A1 | 12/2015 | Toth et al. |
| 2015/0352396 A1 | 12/2015 | Dalebout |
| 2015/0352401 A1 | 12/2015 | Johnson |
| 2015/0352402 A1 | 12/2015 | Arnold et al. |
| 2015/0352404 A1 | 12/2015 | Schwenger |
| 2015/0360133 A1 | 12/2015 | MacCallum et al. |
| 2015/0364026 A1 | 12/2015 | Rubin et al. |
| 2015/0364058 A1 | 12/2015 | Lagree |
| 2015/0366746 A1 | 12/2015 | Ashby |
| 2015/0367158 A1 | 12/2015 | Pretz et al. |
| 2015/0367176 A1 | 12/2015 | Bejestan et al. |
| 2015/0369326 A1 | 12/2015 | Modrezejewski et al. |
| 2015/0370320 A1 | 12/2015 | Connor |
| 2015/0379239 A1 | 12/2015 | Basta et al. |
| 2015/0379891 A1 | 12/2015 | Wallace |
| 2015/0381736 A1 | 12/2015 | Seltzer |
| 2016/0008650 A1 | 1/2016 | Jue et al. |
| 2016/0012749 A1 | 1/2016 | Connor |
| 2016/0016035 A1 | 1/2016 | Hao |
| 2016/0018119 A1 | 1/2016 | Desmet et al. |
| 2016/0027325 A1 | 1/2016 | Malhotra |
| 2016/0038785 A1 | 2/2016 | Netter |
| 2016/0047446 A1 | 2/2016 | Hung |
| 2016/0051184 A1 | 2/2016 | Wisbey et al. |
| 2016/0058245 A1 | 3/2016 | Smith et al. |
| 2016/0059077 A1 | 3/2016 | Paul et al. |
| 2016/0059078 A1 | 3/2016 | Liao |
| 2016/0059079 A1 | 3/2016 | Liao |
| 2016/0061300 A1 | 3/2016 | Aoto et al. |
| 2016/0063615 A1 | 3/2016 | Watterson |
| 2016/0067537 A1 | 3/2016 | Bayerlein et al. |
| 2016/0071014 A1 | 3/2016 | Brand et al. |
| 2016/0074701 A1 | 3/2016 | Wiener |
| 2016/0074705 A1 | 3/2016 | Wiener |
| 2016/0077547 A1 | 3/2016 | Aimone et al. |
| 2016/0089569 A1 | 3/2016 | Blahnik |
| 2016/0096064 A1 | 4/2016 | Gattie |
| 2016/0107029 A1 | 4/2016 | Kim et al. |
| 2016/0112684 A1 | 4/2016 | Connor |
| 2016/0114211 A1 | 4/2016 | Schmidt |
| 2016/0121161 A1 | 5/2016 | Mountain |
| 2016/0136483 A1 | 5/2016 | Reich |
| 2016/0148535 A1 | 5/2016 | Ashby |
| 2016/0148536 A1 | 5/2016 | Ashby |
| 2016/0151603 A1 | 6/2016 | Shouldice et al. |
| 2016/0157740 A1 | 6/2016 | Kampman et al. |
| 2016/0166881 A1 | 6/2016 | Ridgel et al. |
| 2016/0171110 A1 | 6/2016 | Gao et al. |
| 2016/0175643 A1 | 6/2016 | Kueker et al. |
| 2016/0184625 A1 | 6/2016 | Chang |
| 2016/0184635 A1 | 6/2016 | Kwon |
| 2016/0193518 A1 | 7/2016 | Baxter |
| 2016/0206922 A1 | 7/2016 | Dalebout et al. |
| 2016/0211841 A1 | 7/2016 | Harrison |
| 2016/0232811 A9 | 8/2016 | Connor |
| 2016/0249365 A1 | 8/2016 | Harel |
| 2016/0250519 A1 | 9/2016 | Watterson |
| 2016/0253918 A1 | 9/2016 | Watterson |
| 2016/0256082 A1 | 9/2016 | Ely et al. |
| 2016/0256745 A1 | 9/2016 | Brammer |
| 2016/0263426 A1 | 9/2016 | Mueller et al. |
| 2016/0279462 A1 | 9/2016 | Sutherland |
| 2016/0279470 A1 | 9/2016 | Hampton |
| 2016/0287930 A1 | 10/2016 | Moser |
| 2016/0296053 A1 | 10/2016 | Bakhsh |
| 2016/0303421 A1 | 10/2016 | Tyger et al. |
| 2016/0317861 A1 | 11/2016 | Dalebout |
| 2016/0317866 A1 | 11/2016 | Fung |
| 2016/0321932 A1 | 11/2016 | Mitchell |
| 2016/0346598 A1 | 12/2016 | Manzke et al. |
| 2016/0346616 A1 | 12/2016 | Kirby et al. |
| 2016/0351070 A1 | 12/2016 | Aillon-Sohl |
| 2016/0367851 A1 | 12/2016 | Astilean et al. |
| 2016/0367857 A1 | 12/2016 | Aragones et al. |
| 2016/0371998 A1 | 12/2016 | Fazeel et al. |
| 2016/0375307 A1 | 12/2016 | Durham |
| 2016/0375308 A1 | 12/2016 | Anderson |
| 2017/0007886 A1 | 1/2017 | Alessandri |
| 2017/0011210 A1 | 1/2017 | Cheong et al. |
| 2017/0014661 A1 | 1/2017 | Lin |
| 2017/0020440 A1 | 1/2017 | Flitsch et al. |
| 2017/0036106 A1 | 2/2017 | Stechschulte et al. |
| 2017/0050069 A1 | 2/2017 | Ky |
| 2017/0050102 A1 | 2/2017 | Kelly |
| 2017/0056716 A1 | 3/2017 | Cutler |
| 2017/0056726 A1 | 3/2017 | Dalebout et al. |
| 2017/0063567 A1 | 3/2017 | Tanaka et al. |
| 2017/0065187 A1 | 3/2017 | Hsieh et al. |
| 2017/0065947 A1 | 3/2017 | Haney et al. |
| 2017/0068782 A1 | 3/2017 | Pillai et al. |
| 2017/0082983 A1 | 3/2017 | Katzer et al. |
| 2017/0093451 A1 | 3/2017 | Chen et al. |
| 2017/0097717 A1 | 4/2017 | Anisetti et al. |
| 2017/0100636 A1 | 4/2017 | Umetsu et al. |
| 2017/0104425 A1 | 4/2017 | Meloche |
| 2017/0113093 A1 | 4/2017 | Bellavista et al. |
| 2017/0120102 A1 | 5/2017 | Chen |
| 2017/0128783 A1 | 5/2017 | Hasegawa et al. |
| 2017/0128784 A1 | 5/2017 | Molins et al. |
| 2017/0136280 A1 | 5/2017 | Lee |
| 2017/0136288 A1 | 5/2017 | Huang |
| 2017/0136289 A1 | 5/2017 | Frank |
| 2017/0136291 A1 | 5/2017 | Huang |
| 2017/0136293 A1 | 5/2017 | Caccia |
| 2017/0136301 A1 | 5/2017 | Cameron |
| 2017/0136339 A1 | 5/2017 | Habiche |

(56) References Cited

U.S. PATENT DOCUMENTS

| | | |
|---|---|---|
| 2017/0144051 A1 | 5/2017 | Oleson et al. |
| 2017/0164876 A1 | 6/2017 | Hyde et al. |
| 2017/0165523 A1 | 6/2017 | Chou |
| 2017/0180535 A1 | 6/2017 | Esenwein et al. |
| 2017/0189745 A1 | 7/2017 | Hamilton et al. |
| 2017/0193578 A1 | 7/2017 | Watterson |
| 2017/0216660 A1 | 8/2017 | Lernihan |
| 2017/0225034 A1 | 8/2017 | Kass et al. |
| 2017/0235922 A1 | 8/2017 | Weast et al. |
| 2017/0252623 A1 | 9/2017 | Sharifi |
| 2017/0252641 A1 | 9/2017 | Morimura et al. |
| 2017/0266483 A1 | 9/2017 | Dalebout et al. |
| 2017/0266503 A1 | 9/2017 | Watterson et al. |
| 2017/0266532 A1 | 9/2017 | Watterson |
| 2017/0266533 A1 | 9/2017 | Dalebout |
| 2017/0266534 A1 | 9/2017 | Watterson |
| 2017/0266535 A1 | 9/2017 | Watterson |
| 2017/0270820 A1 | 9/2017 | Ashby |
| 2017/0274237 A1 | 9/2017 | Chang |
| 2017/0274242 A1 | 9/2017 | Corbalis |
| 2017/0311817 A9 | 11/2017 | Hsieh et al. |
| 2017/0326411 A1 | 11/2017 | Watterson |
| 2017/0333755 A1 | 11/2017 | Rider |
| 2017/0340917 A1 | 11/2017 | Chang |
| 2017/0354846 A1 | 12/2017 | Von Rueckmann |
| 2017/0364661 A1 | 12/2017 | Hamilton, II et al. |
| 2017/0365048 A1 | 12/2017 | Hamilton, II |
| 2017/0368442 A1 | 12/2017 | Baudhuin |
| 2018/0001135 A1 | 1/2018 | Powell |
| 2018/0008865 A9 | 1/2018 | Lannon et al. |
| 2018/0036572 A1 | 2/2018 | Hsu |
| 2018/0036585 A1 | 2/2018 | Powell |
| 2018/0056111 A1 | 3/2018 | Chiang et al. |
| 2018/0084817 A1 | 3/2018 | Capell et al. |
| 2018/0085630 A1 | 3/2018 | Capell et al. |
| 2018/0085654 A1 | 3/2018 | Black et al. |
| 2018/0089396 A1 | 3/2018 | Capell et al. |
| 2018/0092603 A1 | 4/2018 | Duan et al. |
| 2018/0099116 A1 | 4/2018 | Ashby |
| 2018/0099179 A1 | 4/2018 | Chatterton et al. |
| 2018/0099180 A1 | 4/2018 | Wilkinson |
| 2018/0099181 A1 | 4/2018 | Powell et al. |
| 2018/0099184 A1 | 4/2018 | Eder |
| 2018/0099205 A1 | 4/2018 | Watterson |
| 2018/0104533 A1 | 4/2018 | Powell et al. |
| 2018/0109838 A1 | 4/2018 | Garcia et al. |
| 2018/0111018 A1 | 4/2018 | Lee |
| 2018/0111034 A1 | 4/2018 | Watterson |
| 2018/0116599 A1 | 5/2018 | Bastide et al. |
| 2018/0117383 A1 | 5/2018 | Workman |
| 2018/0117385 A1 | 5/2018 | Watterson et al. |
| 2018/0117388 A1 | 5/2018 | Porter |
| 2018/0117419 A1 | 5/2018 | Jackson |
| 2018/0147440 A1 | 5/2018 | Lin |
| 2018/0154205 A1 | 6/2018 | Watterson |
| 2018/0154206 A1 | 6/2018 | Kim |

OTHER PUBLICATIONS

Taiwan Intellectual Property Office for Taiwan Invention Patent Application No. 104107623; Office Action and Search Report; dated Mar. 21, 2016; pp. 1-13.

* cited by examiner

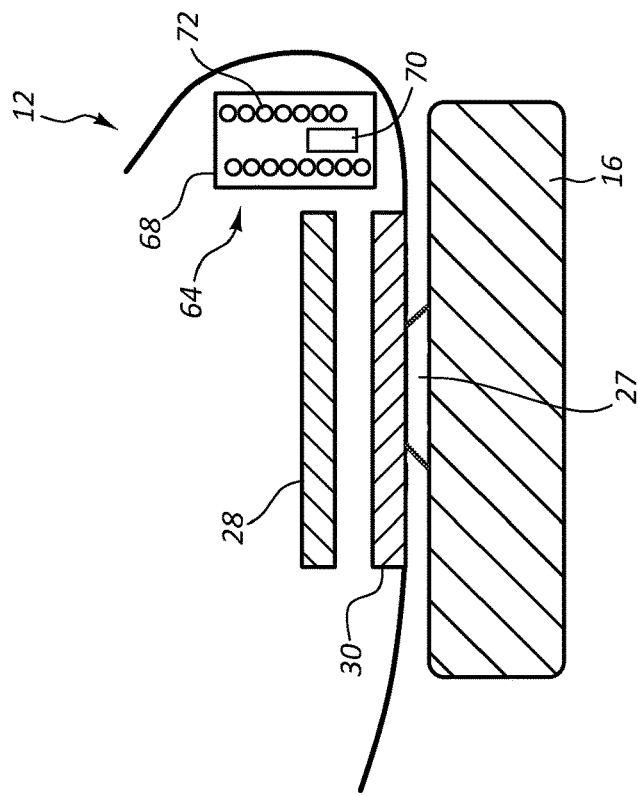
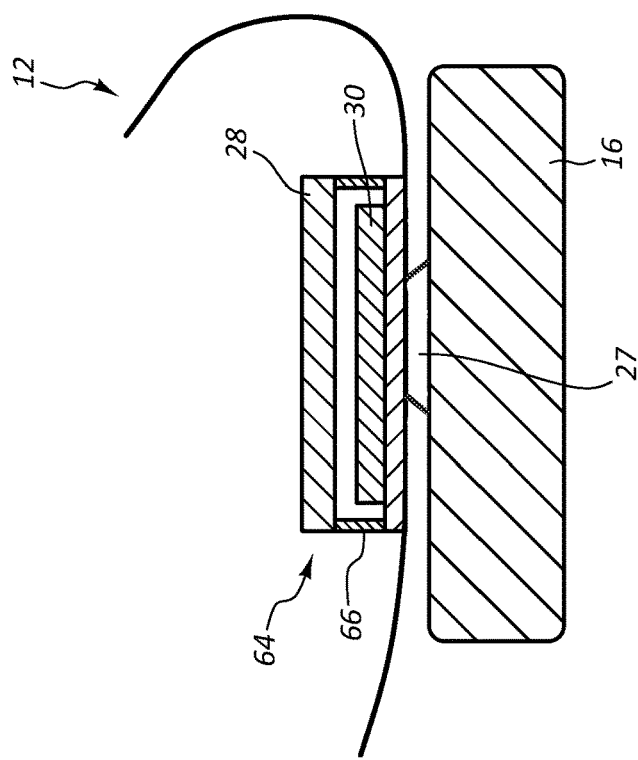
FIG. 7
FIG. 6

PRESSURE SENSOR TO QUANTIFY WORK

RELATED APPLICATIONS

This application claims priority to provisional Patent Application No. 61/950,606 titled "Pressure Sensor to Quantify Work" filed Mar. 10, 2014. This application is herein incorporated by reference for all that it discloses.

BACKGROUND

To propel a bicycle, a user sits on a seat and straddles a frame with his or her legs. A pair of pedals are connected to each other with a pair of crank arms that are connected to a gear assembly. The pedals are positioned to be engaged by the feet and to travel in a reciprocating motion powered by the user's feet. The gear assembly directs the energy exerted through the user's feet to an axle of one of the wheels of the bicycle, which causes the wheel to turn. Such rotation of the wheel propels the bicycle forward. The speed at which the bicycle travels is dependent on the amount of resistance on the bicycle and the amount of energy that the user exerts with his or her legs to rotate the wheel. The resistance on the bicycle generally includes the collective weight of the bicycle and the user as well as the slope of the terrain on which the bicycle is being propelled. In the case of a stationary bicycle, the resistance may be provided with a magnetic resistance mechanism, a pneumatic resistance mechanism, a hydraulic resistance mechanism, a gear type resistance mechanism, braking pads, tensioning elements, fan blades, another type of resistance mechanism, or combinations thereof.

One mechanism for measuring the amount of energy exerted by the user is disclosed in U.S. Patent Publication No. 2003/0074985 issued to Gordon Liao. In this reference, a sensor of the pedaling force of a power-assisting bike includes a transmission system provided with at least one pair of screw gears. One of the screw gears is activated by the pedaling force to rotate at an original location and the other driven by a screw gear engaging to rotate and shift along a shaft, with a resilience member fitted at an end side. An annular magnet is fitted around the end of the shaft of the resilience member and the screw gear, capable to shift together with the screw gear. A Hall sensor is provided on a fixed side of the annular magnet. Thus, the lateral force produced by the screw gears can detect an axially shifting distance of the screw gear and give out a voltage signal to control a motor to output motive power for the bike. Another type of mechanism for measuring the amount of energy exerted by the user is described in U.S. Pat. No. 8,011,242 issued to George David O'Neill. Each of these references are herein incorporated by reference for all that they disclose.

SUMMARY

In a preferred embodiment of the invention, a monitoring system includes a shoe and a sole integrated into the shoe. The monitoring system also includes a connection mechanism attached to an underside of the sole and is shaped to connect the sole to a pedal. A pressure sensor is incorporated into the shoe that senses a force exerted on the pedal when the shoe is connected to the pedal through the connection mechanism.

In one aspect of the invention, the pressure sensor distinguishes between upward forces and downward forces.

In one aspect of the invention, the shoe also comprises an accelerometer that senses a direction of the force exerted on the pedal.

In one aspect of the invention, the shoe also comprises a wireless transmitter that transmits measurements of the pressure sensor to a computing device.

In one aspect of the invention, the computing device comprises a processor and memory with programmed instructions where the programmed instructions cause the processor to quantify the force based at least in part on the measurements of the pressure sensor.

In one aspect of the invention, the programmed instructions further cause the processor to quantify a calorie count based at least in part on the measurements of the pressure sensor.

In one aspect of the invention, the connection mechanism is a clipless pedal system.

In one aspect of the invention, the pressure sensor is positioned proximate a cleat receptacle of the clipless pedal system.

In one aspect of the invention, the pressure sensor is a capacitive based pressure sensor.

In one aspect of the invention, the capacitive based pressure sensor comprises electrically conducting plates that are spaced a distance from each other, wherein the electrically conducting plates move such that the distance narrows during a downward force and the distance widens during an upward force.

In one aspect of the invention, the shoe further comprises an energy harvesting mechanism that converts a motion of the shoe into electrical power when the shoe is in motion.

In one aspect of the invention, the shoe further comprises an energy harvesting mechanism that converts a pressure exerted onto the sole into electrical power.

In one aspect of the invention, a monitoring system may include a shoe.

In one aspect of the invention, a sole integrated into the shoe.

In one aspect of the invention, a clipless pedal system that connects the sole to a pedal when the pedal is attached to the clipless pedal system.

In one aspect of the invention, a pressure sensor incorporated into the shoe and positioned proximate a cleat receptacle of the clipless pedal system.

In one aspect of the invention, the pressure sensor senses a force exerted on the pedal.

In one aspect of the invention, the pressure sensor distinguishes between upward forces and downward forces.

In one aspect of the invention, the shoe further comprises an energy harvesting mechanism that supplies the pressure sensor with electrical power.

In one aspect of the invention, the shoe also comprises an accelerometer that that senses a direction of the force exerted on the pedal.

In one aspect of the invention, the shoe also comprises a wireless transmitter that transmits measurements of the pressure sensor to a computing device.

In one aspect of the invention, the computing device comprises a processor and memory with programmed instructions that cause the processor to quantify the force based at least in part on the measurements of the pressure sensor.

In one aspect of the invention, the programmed instructions further cause the processor to quantify a calorie count based at least in part on the measurements of the pressure sensor.

In one aspect of the invention, the pressure sensor is a capacitive based pressure sensor.

In one aspect of the invention, the capacitive based pressure sensor comprises electrically conducting plates that are spaced a distance from each other, wherein the electrically conducting plates move such that the distance narrows during a downward force to the pedal and the distance widens during an upward force to the pedal.

In one aspect of the invention, a monitoring system may comprise a shoe.

In one aspect of the invention, a sole integrated into the shoe.

In one aspect of the invention, a clipless pedal system that connects the sole to a pedal when the pedal is attached to the clipless pedal system.

In one aspect of the invention, a capacitive based pressure sensor incorporated into the shoe and positioned proximate a cleat receptacle of the clipless pedal system.

In one aspect of the invention, the capacitive based pressure sensor that senses a force exerted on the pedal wherein the capacitive based pressure sensor distinguishes between upward forces to the pedal through the shoe and downward forces to the pedal through the shoe.

In one aspect of the invention, the shoe further comprises an energy harvesting mechanism that supplies the capacitive based pressure sensor with electrical power.

In one aspect of the invention, an accelerometer incorporated into the shoe that senses a direction of the force exerted on the pedal.

In one aspect of the invention, the capacitive based pressure sensor comprises electrically conducting plates that are spaced a distance from each other, wherein the electrically conducting plates move such that the distance narrows during a downward force on the pedal and the distance widens during an upward force to the pedal.

In one aspect of the invention, a wireless transmitter incorporated into the shoe that transmits measurements of the capacitive based pressure sensor to a computing device.

In one aspect of the invention, the computing device comprises a processor and memory with programmed instructions.

In one aspect of the invention, the programmed instructions cause the processor to quantify the force based at least in part on the measurements of the capacitive based pressure sensor.

In one aspect of the invention, the programmed instructions cause the processor to quantify a calorie count based at least in part on the measurements of the capacitive based pressure sensor.

Any of the aspects of the invention detailed above may be combined with any other aspect of the invention detailed herein.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

FIG. 6 illustrates a cross sectional view of an example of an energy harvesting mechanism in accordance with the present disclosure.

FIG. 7 illustrates a cross sectional view of an example of an energy harvesting mechanism in accordance with the present disclosure.

Throughout the drawings, identical reference numbers designate similar, but not necessarily identical, elements.

DETAILED DESCRIPTION

Figure 1:
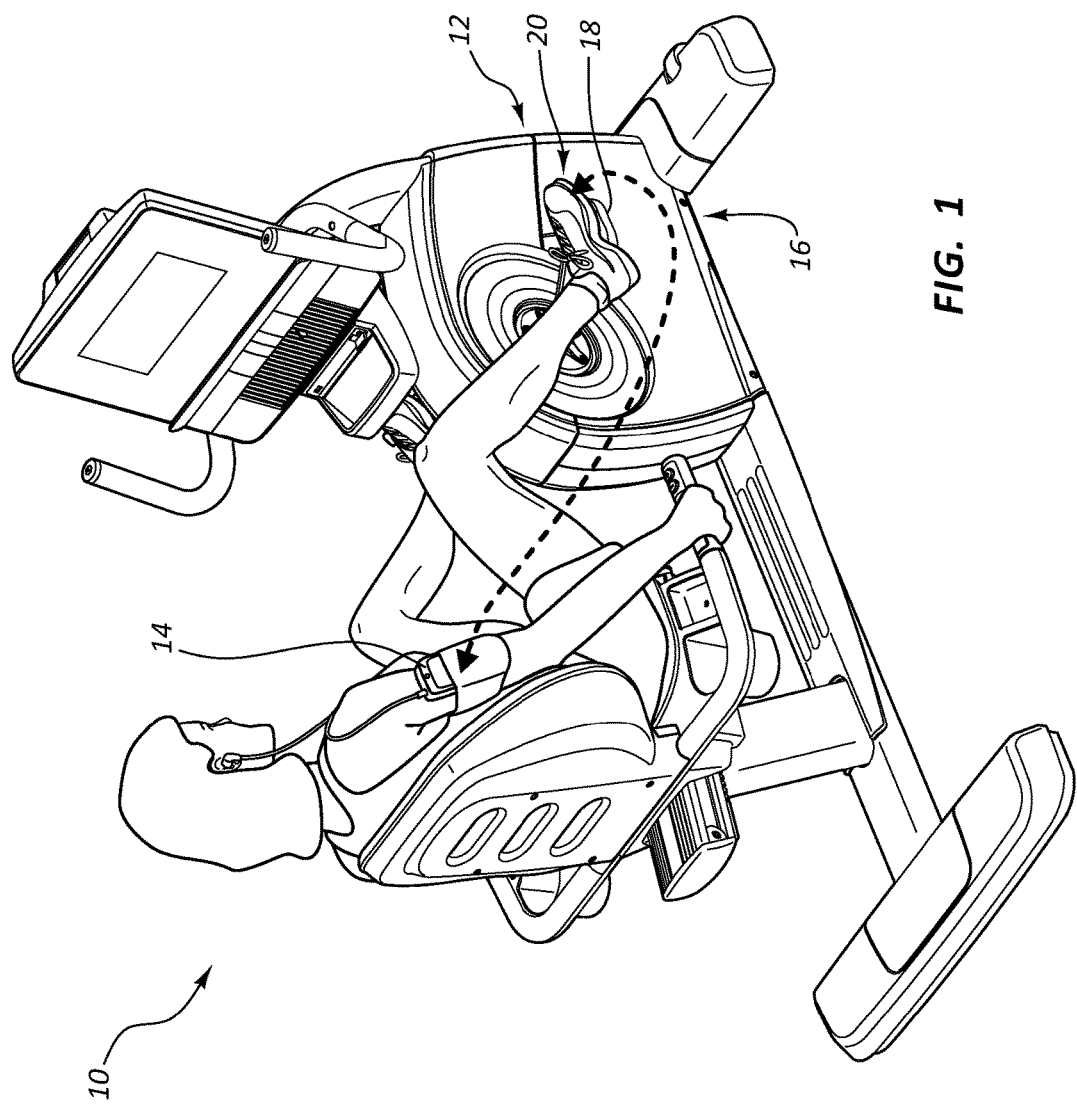
FIG. 1 illustrates a perspective view of an example of a stationary bike in accordance with the present disclosure.

Clipless bicycle pedals allow a rigid attachment to be made between a user's shoe and the pedal. Often, clipless bicycle pedals are used in lieu of straps that hold the user's shoe to the pedal as the user pulls up, thus keeping the shoe and the pedal together. These straps that are attached to the pedals stretch as the shoe is raised. As a result, some of the energy exerted by the user to pull up on the pedal through the strap is lost. Further, there is often a gap between the underside of the strap and the top of the user's shoe. Thus, to pull up on the strap with the shoe, the shoe may have be lifted off of the pedal to make contact with the strap's underside. The effort exerted to lift the shoe to the underside of the strap also does not contribute to the movement of the pedals. As a result, more energy is lost in the system. The clipless pedals are constructed to minimize such inefficiencies.

Often, the clipless pedals attach to a specialized shoe that can be locked to the pedal. In some cases, the shoe includes a cleat receptacle that can receive a cleat secured to the pedal. The cleats are often attached to the pedal with one or more bolts. Some shoes with cleat receptacles lock onto the cleat when the user steps firmly onto the pedal in a vertical direction, and the shoe unlocks when the user twists his or her heel outward. Often, the shoes associated with the clipless pedals have rigid soles to maximize efficiency and transfer power to the pedals.

The principles described in the present disclosure include a monitoring system that can measure the amount of work performed by a user on a bicycle. Such a system may be used for bicycles that can be propelled by the user's work, such as a road bicycle or a mountain bicycle. Also, the monitoring system may be incorporated into a stationary bicycle. The monitoring system includes a shoe with a sole that has an underside shaped to attach to a connection mechanism, such as a cleat of a pedal associated with a clipless pedal system. A pressure sensor is also incorporated into the shoe and senses a force exerted on the pedal. In some instances, the pressure sensor senses both upward forces and downward forces exerted by the user. An accelerometer can be used to determine the direction of the force. But, in some examples, the arrangement of the pressure sensor can distinguish between upward forces and downward forces without the assistance of an accelerometer.

The shoe can be in wireless communication with a mobile device or a control module of the stationary bicycle. The values measured with the pressure sensor can be sent to such remote devices where calculations about the amount of work performed by the user are calculated. Such calculations may be used to determine a number of calories burned by the user.

The energy to power the pressure sensor, accelerometer, transmitter, and other components of the monitoring system that are in the shoe can be harvested from the work performed by the user. For example, the power can be harvested through a piezoelectric system, a kinetic capture system, another type of system, or combinations thereof. In some examples, the energy levels performed by the components of the monitoring system are kept low so that enough power can be provided through energy harvesting.

For the purposes of this disclosure, terms such as "upward" are used with reference to motions where the pedal is moving in a direction towards the user's knee. Likewise, for the purposes of this disclosure, terms such as "downward" are used with reference to motions where the pedal is moving in a direction away from the user's knee.

Further, for the purposes of this disclosure, the term "connection mechanism" includes a structure on the underside of the shoe that assists in connecting the shoe to the pedal. Such connection mechanisms can include fittings for bicycle cleats, other attachment fittings, cleats, other mechanism, or combinations thereof.

Particularly, with reference to the figures, FIG. 1 illustrates a perspective view of an example of a stationary bicycle 10 in accordance with the present disclosure. In this example, the user is wearing a shoe 12 that includes a pressure sensor that is in wireless communication with a remote device 14. The pressure sensor collects information about the work performed by the user during the workout. The remote device 14 can use the information sent from the shoe 12 to determine results about the user's workout, like calories burned, distance traveled, speed, and other types of information. The calculated results can be presented to the user in real time, such as in a display of the stationary bicycle 10. In some examples, the information and/or the calculated results are updated to a database where the user can retrieve them at a later time.

The measurements collected by the shoe 12 can be sent to the remote device 14 in raw form where the data can be processed. In some examples, some data processing occurs prior to the information being sent to the remote device 14. Such data processing may lower the transmission time or lower the transmission power when transmitting data from the shoe 12 to the remote device 14.

In some embodiments, the shoe 12 takes just pressure measurements. However, in some cases the shoe 12 may also include an accelerometer, another type of sensor, or combinations thereof. The measurements from the accelerometer or other sensors may be sent to the remote device 14 with the measurements from the pressure sensor. Information collected by the accelerometer may be used to improve the pressure sensor calculations. The accelerometer can detect movement of the shoe 12, the direction of the movement, the speed of the movement, and other types of information about the movement that may allow the shoe 12, the remote device 14, or other device to correct for motion artifacts exhibited in the pressure measurements.

The remote device 14 may be part of a mobile device that can perform calculations to determine the amount of work exerted by the user. However, in other examples, the remote device 14 is incorporated into a stationary bicycle 10. Any appropriate type of stationary bicycle 10 may be used in accordance with the principles described in the present disclosure. For example, the stationary bicycle 10 may include a magnetic resistance mechanism, a pneumatic resistance mechanism, a hydraulic resistance mechanism, a gear type resistance mechanism, a pair of braking pads, a tensioning element, a fan blade, another type of resistance mechanism, or combinations thereof. While the examples above have been described with reference to bicycles, the principles described herein may be incorporated into other types of exercise or recreational equipment. For example, the principles described herein may be incorporated into elliptical exercise machines, paddle boats, unicycles, tricycles, stepper machines, other types of foot operated devices, or combinations thereof.

Figure 2:
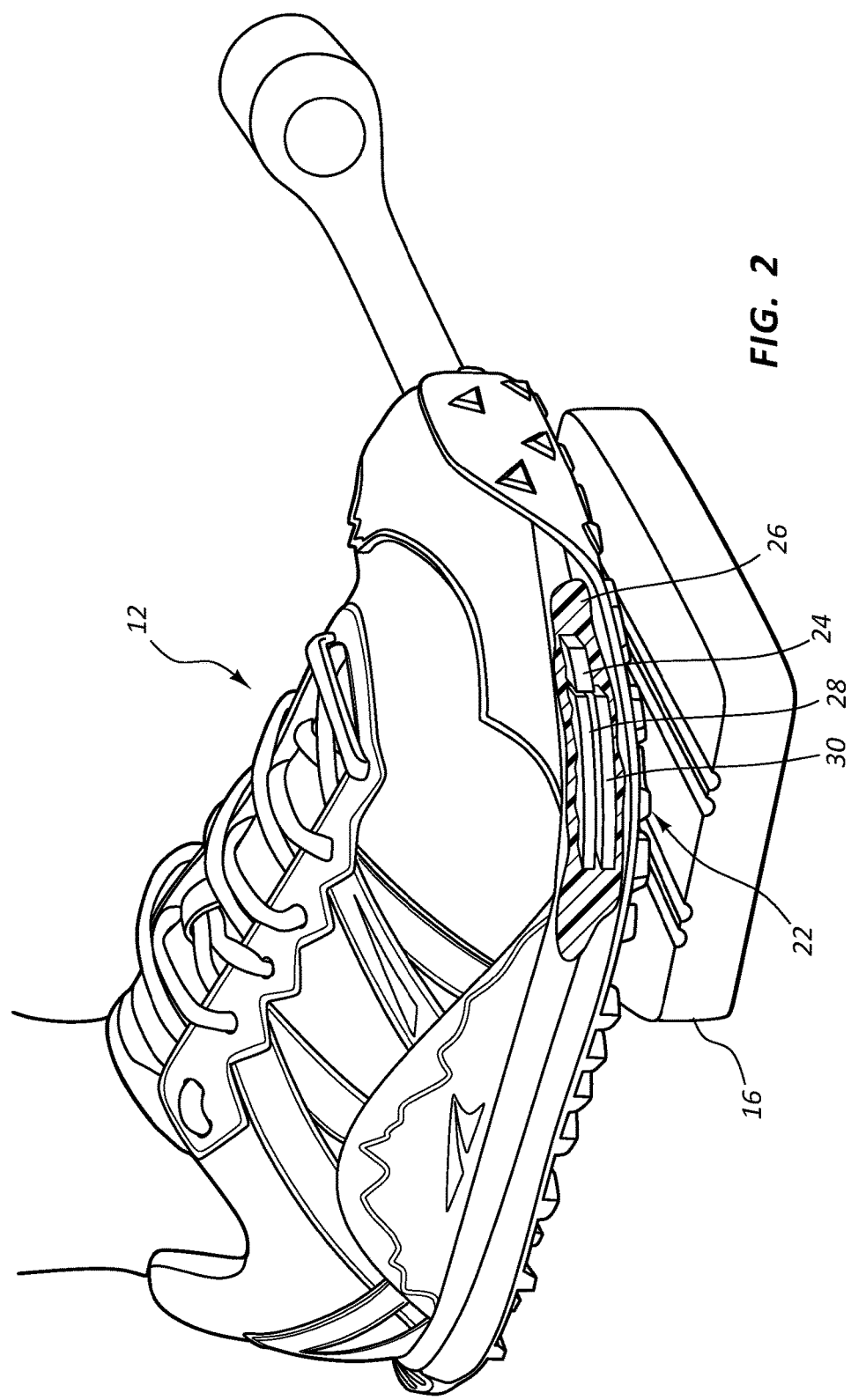
FIG. 2 illustrates a perspective view of an example of a shoe in accordance with the present disclosure.

FIG. 2 illustrates a perspective view of a shoe 12 in accordance with the present disclosure. In this example, the shoe 12 is connected to a pedal 16 through a connection mechanism 18 that is incorporated into a clipless pedal system 20. A pressure sensor 22 and an accelerometer 24 are also incorporated into the shoe 12 and record information while the shoe 12 is secured to the pedal 16 through the clipless pedal system 20.

Any appropriate type of shoe 12 may be used in accordance with the principles described herein. In some examples, the shoe 12 is a cycling shoe 12 that has a sole 26 made of a stiff material to minimize flexing of the sole 26 as a force is transferred from the shoe 12 to the pedal 16. The clipless pedal system 20 includes a cleat receptacle in the sole 26 of the shoe 12. The cleat 27 protrudes upward from the pedal and is shaped to interlock with cleat receptacle of the shoe 12 In some examples, the cleat snaps into a spring loaded mechanism incorporated into the sole 26 of the shoe 12. The cleat may be made of any appropriate material, such as metal, plastic, or other types of material. Further, the cleat may have any appropriate type of shape to interlock with the shoe's sole 26.

Any appropriate type of pedal 16 may be used with the shoe 12 in accordance with the principles described in the present disclosure as long as the pedal 16 is capable of interlocking with the shoe 12 through the connection mechanism 18. In some examples, the pedal 16 can interlock with the shoe 12 on both faces of the pedal, while in other examples, the pedal 16 can interlock with just a single face of the shoe 12.

In the example of FIG. 2, the pressure sensor 22 is positioned above the cleat and comprises a first plate 28 and a second plate 30, which are enlarged for illustrative purposes in the figure. The first and second plates 28, 30 are part of an electrically conductive circuit. The capacitance of the circuit is, in part, dependent on the distance between the first and the second plates 28, 30. The distance between the plates 28, 30 during the pedal's revolution is based on the amount of pressure applied by the user. For example, as the user applies a downward force with his or her foot, the foot pushes on the shoe 12 from within the shoe. This downward force pushes against the first plate 28 and causes the first plate 28 to move with the shoe 12. However, the second plate 30 does not move as much as the first plate 28 in response to the downward force. In other words, there is relative movement between the first plate 28 and the second plate 30. In some examples, the relative movement is caused because second plate 30 is rigidly connected to the pedal 16 through the connection mechanism 18 while the first plate 28 is allowed to move relative to the downward force. In other examples, the sole of the shoe 12 is compressed in response to the downward force causing the first and second plates 28, 30 to move closer.

The pedal 16 can be connected to the gear assembly of a self-propelling, bicycle or to a resistance mechanism of a stationary bicycle 10. The movement of the pedal in the self-propelling, bicycle may be resisted by an incline of the terrain, friction of the terrain, other terrain conditions, the weight of the bicycle, a load on the bicycle, friction in the gear assembly, other conditions, or combinations thereof. Regardless of the source of the resistance to the movement of the pedal 16, the resistance can cause the second plate 30 to move less than the first plate 28. The more three exerted by the user, the greater the relative movement between the first and second plates 28, 30. Further, the greater the relative movement of the first and second plates 28, 30, the greater the distance between the first and second plate 28, 30.

On the back end of the revolution, the user can pull his or her foot in an upward direction. This type of motion can cause the first and second plates 28, 30 to move apart. For example, as the user pulls up, the shoe 12 pulls up with the user's foot. As the shoe 12 moves in the upward direction due to the forces exerted by the user, the first plate 28 moves upward as well. However, the second plate's movement is be resisted by the pedal 16. As a result, the distance between the first plate 28 and the second plate 30 increases.

The distance between the plates 28, 30 can be recorded based on the capacitance of the circuit. In some examples, the capacitance of the circuit is periodically sampled, and the forces are reconstructed based on the samples. Such samples may be gathered at second intervals, microsecond intervals, intervals spanning multiple seconds, other types of intervals, or combinations thereof. In other examples, a measurement signal of the circuit's capacitance is continuously monitored.

The recorded measurements can be stored temporarily in memory in the shoe 12 and then be transmitted to a remote device 14. Such memory may include a buffer, a cache, another type of short term memory, or combinations thereof. In such examples, the temporarily stored measurements nay be sent to the remote device 14 on a periodic basis that allows the measurements to be obtained by the remote device 14 in real time or near real time. For example, a transmitter of the shoe 12 may send the stored data to the remote device 14 at one second intervals, sub-second intervals, microsecond intervals, other types of intervals, or combinations thereof. In other examples, the measurements may be continuously transmitted to the remote device 14.

The data may be processed prior to sending the data to the remote device 14. Such data processing may include compression processing or other types of processing that may reduce the transmission time or the transmission power of sending the data to the remote device 14. In other examples, the signals are not pre-processed prior to sending. The remote device 14 may further process the measurements.

In some examples, the remote device 14 calculates the calories burned, the distance traveled, the speed, and other parameters related to the user's workout based on the pressure measurements. In addition to sending the remote device 14 information from the pressure sensor 22, some examples include sending measurements from the accelerometer 24.

The accelerometer 24 may be positioned in any appropriate location in the shoe 12. The accelerometer 24 may sense motion of the shoe 12 in multiple directions, including upward directions, downward directions, and directions to the side. The accelerometer's measurements may be used to determine if a motion artifact exists in the values collected with the pressure sensor 22. If such a motion artifact exists, the recorded pressures can be modified to reflect the appropriate values without the motion artifact. The accelerometer's measurements may be sent to the memory or directly to the transmitter for conveyance to the remote device 14. In some embodiments, the accelerometer's measurements stay locally within the shoe 12 and are used to modify the recorded pressures prior to sending them to the remote device 14. In other examples, the calculations and other adjustments to be made based on the measurements from the accelerometer 24 are performed at the remote device 14. In other examples, the accelerometer 24 is used to determine the direction of the force applied to the shoe 12.

In some examples, the other information is recorded by other sensors in the shoe 12 or outside of the shoe 12. Such additional measurements may also be sent to the remote device 14. For example, a heart rate monitor 56, an oxygen consumption monitor, a blood pressure monitor, an odometer 58, a speedometer 60, a timer 55, a resistance mechanism 54, another type of sensor, or combinations thereof may send additional information to the remote device 14.

Workout results derived from the information received by the remote device 14 may be presented to the user during his workout in real time or near real time. For example, the calculated information may be displayed in a display of the stationary bicycle 10. In other examples, the information may be displayed in a display that mounts to the handle bars or another component of the self-propelling bicycle. However, in yet other examples, the remote device 14 does not perform calculations on the obtained information, but rather forwards the information to a cloud based network device where the information is accessible to a remote device 14 that can make calculations based on the data. Such a network device may be part of a database that stores information about the user's fitness or exercise activities. In other examples, the remote device 14 forwards the information directly to another device that performs the calculations. In some examples, the results of the calculations are sent back to a local display associated with the bicycle while the user is still performing the workout for providing feedback to the user.

Any appropriate type of communication protocol between the shoe's transmitter and the remote device may be used in accordance with the principles described in the present disclosure. Such protocols may include standard wireless protocols, protocols used by Bluetooth® technologies, Wi-Fi protocols, Z-wave protocols, Zigbee protocols, other types of wireless protocols, or combinations thereof.

In alternative embodiments, the data is stored in the shoe 12 until it is downloaded. In such an example, the stored data may be downloaded after the workout is finished. This allows the user to review his or her results after the workout is concluded. Downloading the data may be accomplished wirelessly. In some examples, a cable can be used to download the data.

Figure 4:
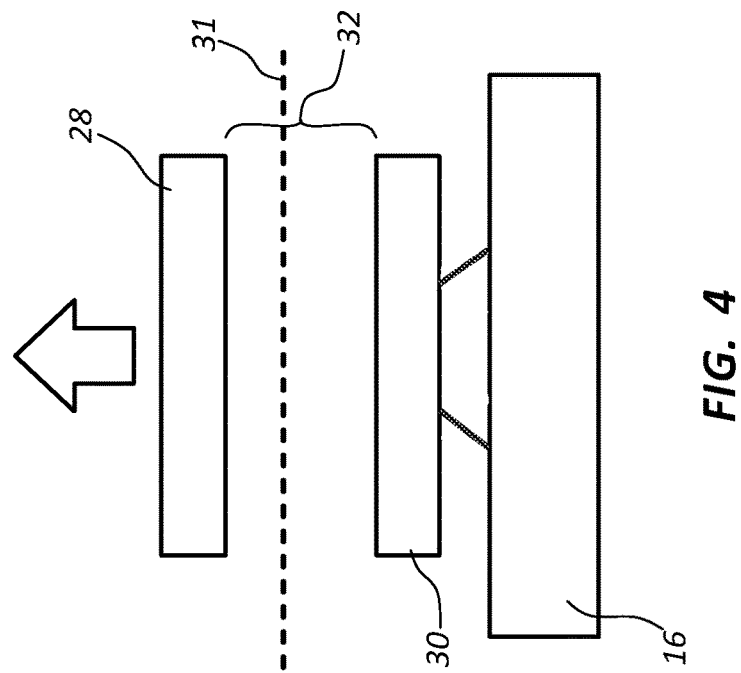
FIG. 4 illustrates a diagram of an example of a pressure sensor in accordance with the present disclosure.
Figure 3:
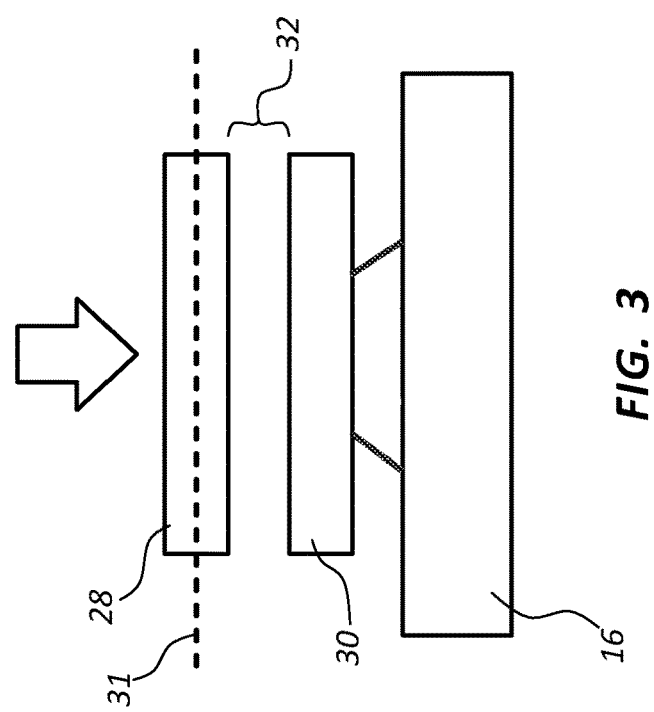
FIG. 3 illustrates a diagram of an example of a pressure sensor in accordance with the present disclosure.

FIGS. 3 and 4 illustrate a pressure sensor 22 in accordance with the present disclosure. In these examples, both the first plate 28 and the second plate 30 of the pressure sensor 22 are disposed within the shoe 12. Additionally, the second plate 30 is rigidly attached to the connection mechanism 18, such as a cleat receptacle. In such examples, when the cleat 27 is interlocked with the cleat receptacle, the second plate 30 is also rigidly attached to the pedal 16. The first plate 28 moves based on the pressures exerted on the sole 26 of the shoe 12. Thus, as the foot exerts an upward force on the shoe 12, the first plate 28 is pulled upwards, which increases the distance 32 between the first plate 28 and the second plate 30. Likewise, as the foot exerts a downward force on the shoe 12, the first plate 28 is pushed downwards, which decreases the distance 32 between the first plate 28 and the second plate 30.

In the illustrated example, the first and the second plates 28, 30 store an electrical charge as part of a circuit. As the distance 32 between the first plate 28 and the second plate 30 changes, the amount of capacitance that the circuit can hold also changes. These capacitive changes can be detected with a capacitance meter, a volt meter, an ammeter, another type of meter, or combinations thereof. As a result, the circuit can exhibit electrical properties that indicate the distance 32 between the plates 28, 30. Thus, as the pressures exerted by the foot cause the plates 28, 30 to move relative to one another, the pressure changes can be sensed by measuring the electrical properties of the circuit.

In some examples, the readings of the pressure sensor 22 indicate whether there is an upward force or a downward force on the pedals. In one approach for determining the direction of the pressure forces, a predetermined baseline distance is selected. A baseline distance between the first plate 28 and the second plate 30 is depicted in FIGS. 3 and 4 with a dashed line 31, which may represents the resulting distance 32 between the plates 28, 30 in the absence of upward or downward forces. In such an example, when there are no forces exerted by the user, the distance 32 between the plates 28, 30 are as though the underside of the first plate 28 rests on the dashed line 31. As a result, when the underside of the first plate 28 is above the dashed line 31, a processing device may determine that there is an upward force on the pedal 16. Likewise, when the underside of the first plate 28 is below the dashed line 31, the processing device may determine that there is a downward force on the pedal 16. In some examples, an electrical property of circuit can correlate with the distance 32 between the plates 28, 30. Thus, a baseline electrical value may be associated with the baseline distance. As a result, a processor may determine whether the force is an upward force or a downward based on whether the electrical property is above or below the baseline value. Further, the processor may understand the amount of force applied in either the upward or downward direction based on how high or how low the measured electrical property is from the baseline value.

In another approach, the processing device may determine that there is an upward force or an downward force by determining whether the distance 32 between the plates is increasing or decreasing. For example, to determine whether a pressure reading associated with a first timestamp is an upward force or a downward force, the processing device may look at a set of distances taken immediately before and/or immediately after the timestamp to determine whether the distances between the plates 28, 30 are increasing or decreasing. If the distance 32 between the plates is increasing, then the processing element may determine that there is an upward force. On the other hand, if the distance 32 between the plates is decreasing, then the processing element may determine that the force is a downward force. As described above, the distance may correspond to an electrical property of the circuit. Thus, in some examples, the direction of the force may be determined by whether the measured electrical property is increasing or decreasing.

In yet another approach, the accelerometer 24 may take measurements to determine whether the pedal 16 is going in an upward direction or a downward direction. In such an approach, measurements from the accelerometer 24 and the pressure sensor 22 may be compared to determine which direction the pedal 16 is moving and assign a direction to the force based on the direction indicated by the accelerometer 24.

In some examples, a pressure sensor 22 and associated components are incorporated into just a single shoe worn by the user. In such a circumstance, the processing device may estimate the forces exerted by the user's other foot. In situations where both shoes worn by the user include the pressure sensor 22 and associated components, the measurements for each shoe 12 can be used to determine the calories and forces specific to the foot exerting the energy. In some examples, a display may indicate which calories, forces, or other parameters are attributable to which foot.

The processing device may have the capability of determining whether the user is pedaling the bicycle, walking, or performing another task. In such an embodiment, the patterns exhibited in the accelerometer's readings and/or the pressure sensor's readings can be analyzed. If it is determined that the user is standing or just walking, the components of the shoe 12 may switch off, discard recorded data, withhold recorded data from the processing device, take another action, or combinations thereof. On the other hand, if the accelerometer's measurements or the pressure sensor's measurements exhibit patterns that suggest that the user is pedaling, the processing device may incorporate the measurements into the calculations for determining a calorie count, stroke specific calculations, torque, other determinations, or combinations thereof. In such examples, the user may start and stop his or her workout without turning on or off the shoe's sensors to avoid integrating non-relevant data into the user's fitness information.

Figure 5:
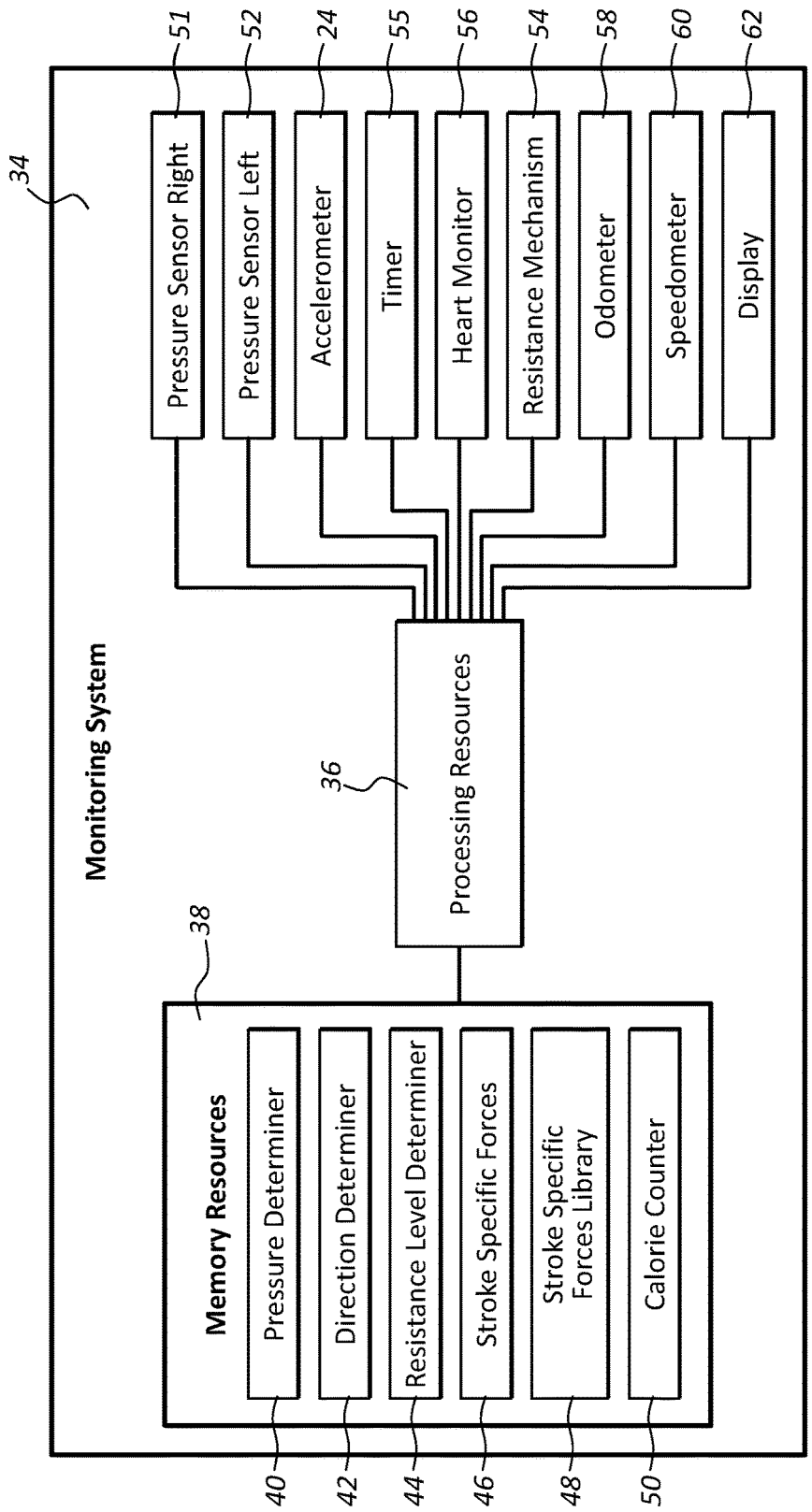
FIG. 5 illustrates a block diagram of an example of a monitoring system in accordance with the present disclosure.

FIG. 5 illustrates a block diagram of an example of a monitoring system 34 in accordance with the present disclosure. The monitoring system 34 may include a combination of hardware and program instructions for executing the functions of the monitoring system 34. In this example, the monitoring system 34 includes processing resources 36 that are in communication with memory resources 38. Processing resources 36 include at least one processor and other resources used to process programmed instructions. The memory resources 38 represent generally any memory capable of storing data such as programmed instructions or data structures used by the monitoring system 34. The programmed instructions shown stored in the memory resources 38 include a pressure determiner 40, a direction determiner 42, a resistance level determiner 44, a stroke specific forces determiner 46, and a calorie counter 50. The data structures shown stored in the memory resources 38 include a stroke specific forces library 48.

The memory resources 38 include a computer readable storage medium that contains computer readable program code to cause tasks to be executed by the processing resources 36. The computer readable storage medium may be a tangible and/or non-transitory storage medium. The computer readable storage medium may be any appropriate storage medium that is not a transmission storage medium. A non-exhaustive list of computer readable storage medium types includes non-volatile memory, volatile memory, random access memory, write only memory, flash memory, electrically erasable program read only memory, magnetic based memory, other types of memory, or combinations thereof.

The pressure determiner 40 represents programmed instructions that, when executed, cause the processing resources 36 to determine the amount of pressure exerted on the pedal 16 based on readings from a right pressure sensor 51 and a left pressure sensor 52. The direction determiner 42 represents programmed instructions that, when executed, cause the processing resources 36 to determine the direction of the pressure exerted on the pedal 16. The direction of the force may be determined based on the readings from the pressure sensors 51, 52. In some examples, the direction of the pressures is determined, at least in part, with an accelerometer 24. The resistance level determiner 44 represents programmed instructions that, when executed, cause the processing resources 36 to determine the amount of resistance applied to reciprocating movement of the pedals based on an output from a resistance mechanism 54. The stroke specific forces determiner 46 represents programmed instructions that, when executed, cause the processing resources 36 to determine forces that are specific to each stroke executed by the user. A non-exhaustive list of stroke specific forces that may be calculated in accordance with the principles described in the present disclosures include torque, revolution speed, calories burned, upward force, downward force, overall force, other types of stroke specific forces, or combinations thereof. These forces may be kept in the stroke specific forces library 48. The calorie counter 50 represents programmed instructions that, when executed, cause the processing resources 36 to track the number of calories burned by the user. The accelerometer 24 may be used to determine when a stroke is completed. A stroke may be an entire revolution, and the accelerometer 24 may record acceleration patterns throughout the revolution. In some examples, as the patterns recorded by the acceleration patterns repeat, the beginning and ending of a stroke can be determined. A timer 55 can associate the measurements with a point in time to assist in determining the time at which the pressure and/or accelerometer measurements were taken.

The calorie counter 50 may use information from the stroke specific library 48, from the pressure sensors 51, 52, the accelerometer 24, a heart rate monitor 56 worn by the user, an odometer 58 mounted to the bicycle, a speedometer 60 mounted to the bicycle, other instruments, or combinations thereof.

The calculated results of the workout can be presented to the user through any appropriate mechanism. In some examples, the calculated results are displayed to the user through a display 62 mounted to the bicycle or a mobile device of the user.

Further, the memory resources 38 may be part of an installation package. In response to installing the installation package, the programmed instructions of the memory resources 38 may be downloaded from the installation package's source, such as a portable medium, a server, a remote network location, another location, or combinations thereof. Portable memory media that are compatible with the principles described herein include DVDs, CDs, flash memory, portable disks, magnetic disks, optical disks, other forms of portable memory, or combinations thereof. In other examples, the program instructions are already installed. Here, the memory resources 38 can include integrated memory such as a hard drive, a solid state hard drive, or the like.

In some examples, the processing resources 36 and the memory resources 38 are located within the shoe 12. The memory resources 38 may be part of the shoe's main memory, caches, registers, non-volatile memory, or elsewhere in the shoe's memory hierarchy. Alternatively, the memory resources 38 may be in communication with the processing resources 36 over a network. Further, the data structures, such as the libraries, may be accessed from a remote location over a network connection while the programmed instructions are located locally. Thus, information from the monitoring system 34 may be accessed from the shoe 12; a user device; a mobile device; a phone; an electronic tablet; a wearable computing device; a head mounted device; a server; a collection of servers; a networked device; a watch; a user interface in a car, truck, plane, boat, bus, another type of automobile; or combinations thereof.

The monitoring system 34 of FIG. 5 may be part of a general purpose computer. However, in alternative examples, the monitoring system 34 is part of an application specific integrated circuit.

FIG. 6 illustrates a cross sectional view of an example of an energy harvesting mechanism 64 in accordance with the present disclosure. In this example, the energy harvesting mechanism 64 includes a piezoelectric material 66 that exhibits a characteristic of producing a voltage when mechanically deformed. In such an example, the piezoelectric material 66 receives a portion of the load when the user exerts a downward force through the shoe 12. Under such a load, the voltage is produced, which generates a current. The piezoelectric material 66 is part of a circuit and is oriented to direct the current and/or voltage generated by the deformation of the piezoelectric material 66 towards a power storage unit.

In some examples, the power storage unit is a capacitor that stores the electrical energy until the energy is needed. At such a time, the capacitor discharges enough energy to power the operation. In some examples, multiple components of the monitoring system 34 are operated by the electrical energy discharged by the capacitor. For example, electrical energy may be used to write measurements into a memory stored in the shoe 12, transmit the measurements to the remote device 14, record an accelerometer reading, write values from the accelerometer reading into memory, process the data recorded by the accelerometer 24 and/or pressure sensor 22, perform other functions, or combinations thereof. In other examples, chargeable batteries or other types of power storage units are incorporated into the shoe 12 and are the recipients of the electrical energy from the energy harvesting mechanism 64.

FIG. 7 illustrates a cross sectional view of an example of an energy harvesting mechanism 64 in accordance with the present disclosure. In this example, the energy harvesting mechanism 64 includes chamber 68 that is shaped to house a reciprocating magnet 70 that travels in response to the movement of the shoe 12. Also, an electrically conductive coil 72 is incorporated into the chamber 68. The electrically conductive coil 72 and the reciprocating magnet 70 are arranged so that as the reciprocating magnet 70 travels in response to the shoe's movement. As the reciprocating magnet 70 travels, it's magnetic field passes through portions of the electrically conductive coil 72, which induces an electrical current. The electrically conductive coil 72 may be incorporated into a circuit that directs the electrical current to the power storage unit, where the stored electrical power can be used for operations of the pressure sensor 22 and other components incorporated into the shoe 12.

Figure 8:
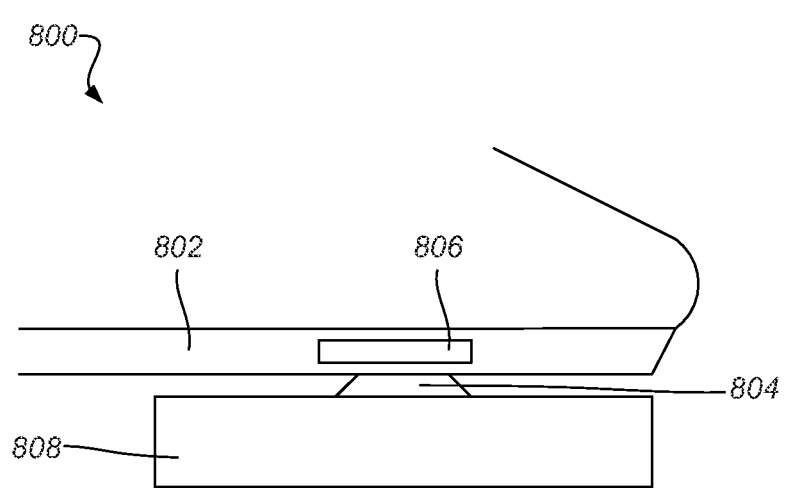
FIG. 8 illustrates a cross sectional view of an example of a monitoring system in accordance with the present disclosure.

FIG. 8 depicts the monitoring system with a shoe 800 and a sole 802 integrated into the shoe 800. A connection mechanism 804 is attached to an underside of the sole 802 and is shaped to connect the sole 802 to a pedal 808. A pressure sensor 806 incorporated into the shoe 800 that senses a force exerted on the pedal 808 when the shoe 800 is connected to the pedal 808 through the connection mechanism 804.

INDUSTRIAL APPLICABILITY

In general, the invention disclosed herein may provide the user with calorie and force calculations associated with the work performed on a bicycle or another foot operated device. The bicycle may be a stationary bicycle or a self-propelled bicycle. The pressure sensor can be incorporated into the shoe proximate the cleat receptacle of a clipless pedal system or another type of system where the shoe is connected to the pedal. The pressure sensor can include at least two plates that move in response to upward forces and/or downward forces exerted by the user while pedaling.

A pressure sensor in accordance with the present disclosure may include a pressure sensor with a first plate and the second plate. In some cases, the second plate is rigidly attached to the connection mechanism, such as a cleat receptacle in the sole of the shoe. In such examples, when the cleat is interlocked with the shoe, the second plate is also rigidly attached to the pedal. The first plate may move based on the pressures exerted on the sole of the shoe. Thus, as the foot exerts an upward force on the shoe, the first plate is pulled upwards, which increases the distance between the first plate and the second plate. Likewise, as the foot exerts a downward force on the shoe, the first plate is pushed downwards, which decreases the distance between the first plate and the second plate.

In the some examples, an electrical circuit is incorporated into the shoe. The electrical shoe includes a first and the second plates that store an electrical charge. As the distance between the first plate and the second plate changes, the amount of capacitance that the circuit can hold also changes. These capacitive changes can be detected with a capacitance meter, a volt meter, an ammeter, another type of meter, or combinations thereof. As a result, the circuit can exhibit electrical properties that indicate the distance between the plates. Thus, as the pressures exerted by the foot cause the plates to move relative to one another, the pressure changes can be sensed by measuring the electrical properties of the circuit.

In some examples, the pressure sensor may indicate whether there is an upward force or a downward force on the pedals. In one approach for determining the direction of the pressure forces, a predetermined baseline distance is selected. A baseline distance between the first plate and the second plate may represents the resulting distance between the plates in the absence of upward or downward forces cause by the turning of the pedal. In such an example, when there are no such forces exerted by the user to turn the pedal, the distance between the plates are at the baseline distance. As a result, when the underside of the first plate is above the baseline distance, a processing device may determine that there is an upward force on the pedal. Likewise, when the underside of the first plate is below the dashed line, the processing device may determine that there is a downward force on the pedal. In some examples, an electrical property of circuit can correlate with the distance between the plates. Thus, a baseline electrical value may be associated with the baseline distance. As a result, a processor may determine whether the force is an upward force or a downward based on whether the electrical property is above or below the baseline value. Further, the processor may understand the amount of force applied in either the upward or downward direction based on how high or how low the measured electrical property is from the baseline value.

In another approach, the processing device may determine that there is an upward force or an downward force by determining whether the distance between the plates is increasing or decreasing. For example, to determine whether a pressure reading associated with a first timestamp is an upward force or a downward force, the processing device may look at a set of distances taken immediately before and/or immediately after the timestamp to determine whether the distances between the plates are increasing or decreasing. If the distance between the plates is increasing, then the processing element may determine that there is an upward force. On the other hand, if the distance between the plates is decreasing, then the processing element may determine that the force is a downward force. In some examples, the distance may correspond to an electrical property of the circuit. Thus, in some examples, the direction of the force may be determined by whether the measured electrical property is increasing or decreasing.

In yet another approach, the accelerometer may take measurements to determine whether the pedal is going in an upward direction or a downward direction. In such an approach, measurements from the accelerometer and the pressure sensor may be compared to determine which direction the pedal is moving and assign a direction to the force based on the direction indicated by the accelerometer.

In some examples, a pressure sensor and associated components are incorporated into just a single shoe worn by the user. In such a circumstance, the processing device may estimate the forces exerted by the user's other foot. In situations where both shoes worn by the user include the pressure sensor and associated components, the measurements for each shoe can be used to determine the calories and forces specific to the foot exerting the energy. In some examples, a display may indicate which calories, forces, or other parameters are attributable to which foot.

The processing device may have the capability of determining whether the user is pedaling the bicycle, walking, or performing another task. In such an embodiment, the patterns exhibited in the accelerometer's readings and/or the pressure sensor's readings can be analyzed. If it is determined that the user is standing or just walking, the components of the shoe may switch off, discard recorded data, withhold recorded data from the processing device, take another action, or combinations thereof. On the other hand, if the accelerometer's measurements or the pressure sensor's measurements exhibit patterns that suggest that the user is pedaling, the processing device may incorporate the measurements into the calculations for determining a calorie count, stroke specific calculations, torque, other determinations, or combinations thereof. In such examples, the user may start and stop his or her workout by turning on or off the shoe's sensors to avoid integrating non-relevant data into the user's fitness information.

The pressure sensor and other components with the shoe can be powered with an energy harvesting mechanism that minimizes or eliminates batteries or an external power source. This reduces the weight of the shoe and spares the user from having to replace the batteries. Such energy harvesting mechanisms can include kinetic capture mechanisms, piezoelectric mechanisms, self-powered generator mechanisms, thermopile mechanisms, or combinations thereof. In some examples, the movement of the shoe causes coils to pass through a magnetic field. Such movement may be achieved through allowing some internal components of the shoe to move relative to other internal components as the shoe moves. For example, a magnet may move relative to coils as the shoe moves. In other examples, the coils may move in relation to a magnetic field. In either example, the differential movement between the coils and the magnetic field may generate an electrical current in the coils, which current may be directed to a battery or directly to the components of the shoe that user electrical power.

The monitoring system may include a shoe and a sole integrated into the sole. A connection mechanism may be attached to an underside of the sole and be shaped to connect the sole to a pedal. A pressure sensor may be incorporated into the shoe that senses a force exerted on the pedal when the shoe is connected to the pedal through the connection mechanism. In some cases, the pressure sensor can distinguish between upward forces imposed on the pedal and downward forces imposed on the pedal.

The measurements of the pressure sensor and the accelerometer (in those embodiments that include an accelerometer) may be transmitted to an external device, such as a mobile device carried by the user while on the exercise machine, another computing device, a network device, another type of device, or combinations thereof. Such a computing device may quantify the forces exerted onto the pedal and use such force determinations to determine a calorie count or another unit of energy consumption performed by the user.

The connection mechanism that connects the shoe to the pedal may be a clipless pedal system where a cleat receptacle of the underside of the shoe interlocks with the cleat from the pedal. The pressure sensor may be disposed proximate the cleat receptacle.

In some cases, the pressure sensor is a capacitive based pressure sensor. In such an example, the capacitive based pressure sensor may comprise electrically conducting plates that are spaced a distance from each other. The electrically conducting plates may move such that the distance between the plates narrows during a downward force on the pedal and the distance widens during an upward force on the pedal.

Any appropriate type of shoe may be used in accordance with the principles described herein. In some examples, the shoe is a cycling shoe that has a sole made of a stiff material to minimize flexing of the sole as a force is transferred from the shoe to the pedal. The clipless pedal system includes a cleat receptacle in the sole of the shoe. The cleat protrudes upward from the pedal and is shaped to interlock with cleat receptacle of the shoe. In some examples, the cleat snaps into a spring loaded mechanism incorporated into the sole of the shoe. The cleat may be made of any appropriate material, such as metal, plastic, or other types of material. Further, the cleat may have any appropriate type of shape to interlock with the shoe's sole.

Any appropriate type of pedal may be used with the shoe as long as the pedal is capable of interlocking with the shoe through the connection mechanism. In some examples, the pedal can interlock with the shoe on both faces of the pedal, while in other examples, the pedal can interlock with just a single face of the shoe.

What is claimed is:

1. A monitoring system, comprising:
a shoe;
a sole integrated into the shoe;
a connection mechanism attached to an underside of the sole, wherein the connection mechanism is shaped to connect the sole to a pedal;
a pressure sensor comprising a first plate and a second plate spaced apart from the first plate to form a capacitor, wherein the pressure sensor is incorporated within the sole of the shoe that senses a force exerted on the pedal when the shoe is connected to the pedal through the connection mechanism, wherein the first plate is located above the second plate, a baseline distance between the first plate and the second plate representing a distance between the first plate and the second plate in the absence of upward and downward forces, and the pressure sensor determines an upward force based on if the distance between the first plate and the second plate is greater than the baseline distance and the pressure sensor determines a downward force if the distance between the first plate and the second plate is less than the baseline distance; and
an energy harvesting mechanism disposed in the shoe and physically independent of the pressure sensor, the energy harvesting mechanism including a reciprocating element and a stationary element, where the reciprocating element induces an electric current upon moving relative to the stationary element, and wherein the electric current of the energy harvesting mechanism supplies the pressure sensor with electrical power.

2. The monitoring system of claim 1, wherein the shoe further comprises an accelerometer.

3. The monitoring system of claim 1, wherein the shoe further comprises a wireless transmitter that transmits measurements of the pressure sensor to a computing device.

4. The monitoring system of claim 3, wherein the computing device comprises a processor and memory with non-transitory programmed instructions containing computer instructions store therein, wherein the non-transitory programmed instructions cause the processor to quantify the force based at least in part on the measurements of the pressure sensor.

5. The monitoring system of claim 4, wherein the non-transitory programmed instructions further cause the processor to quantify a calorie count based at least in part on the measurements of the pressure sensor.

6. The monitoring system of claim 3, wherein the computing device includes a processor and a memory, the memory including programmable instructions, which, when accessed by the processor, cause the processor to determine if a user standing or walking.

7. The monitoring system of claim 6, wherein the programmable instructions further cause the processor to switch off the pressure sensor, discard recorded data, or withhold recorded data when the user is standing or walking.

8. The monitoring system of claim 1, wherein the connection mechanism is a clipless pedal system.

9. The monitoring system of claim 8, wherein the pressure sensor is positioned proximate a cleat receptacle of the clipless pedal system.

10. The monitoring system of claim 1, wherein the pressure sensor is a capacitive based pressure sensor.

11. The monitoring system of claim 1, wherein the energy harvesting mechanism that converts a pressure exerted onto the sole into electrical power.

12. A monitoring system, comprising:
a shoe;
a sole integrated into the shoe;
a cleat receptacle formed in the sole;
a clipless pedal system that connects the sole to a pedal when the pedal is attached to the clipless pedal system;
a pressure sensor comprising a first plate and a second plate spaced apart from the first plate to form a capacitor, wherein the pressure sensor is incorporated within the sole of the shoe, wherein the pressure sensor is positioned proximate the cleat receptacle, wherein the first plate is located above the second plate, a baseline distance between the first plate and the second plate representing a distance between the first plate and the second plate in the absence of upward and downward forces, and the pressure sensor determines an upward force based on if the distance between the first plate and the second plate is greater than the baseline distance and the pressure sensor determines a downward force if the distance between the first plate and the second plate is less than the baseline distance; and
an energy harvesting mechanism disposed in a separate area of the shoe than the pressure sensor, the energy harvesting mechanism including a reciprocating element and a stationary element, where the reciprocating element induces an electric current upon moving relative to the stationary element, and wherein the electric current of the energy harvesting mechanism supplies the pressure sensor with electrical power.

13. The monitoring system of claim 12, further comprising an accelerometer disposed in the shoe.

14. The monitoring system of claim 12, wherein the shoe further comprises a wireless transmitter that transmits measurements of the pressure sensor to a computing device.

15. The monitoring system of claim 14, wherein the computing device comprises a processor and memory, wherein the memory includes non-transitory programmed instructions containing computer instructions store therein that, when accessed by the processor, cause the processor to quantify a force based at least in part on the measurements of the pressure sensor.

16. The monitoring system of claim 15, wherein the non-transitory programmed instructions further cause the processor to quantify a calorie count based at least in part on the measurements of the pressure sensor.

17. A monitoring system, comprising:
a computing device;
a shoe;
a sole integrated into the shoe;
a cleat receptacle formed in the sole;
a clipless pedal system that connects the sole to a pedal when the pedal is attached to the clipless pedal system;
a capacitive based pressure sensor comprising a first plate and a second plate spaced apart from the first plate to form a capacitor, wherein the second plate is located above the first plate, wherein the pressure sensor is incorporated within the sole of the shoe and positioned proximate a cleat receptacle, wherein the capacitive based pressure sensor includes a baseline distance between the first plate and the second plate, wherein the baseline distance represents a distance between the first plate and the second plate in the absence of upward and downward forces, and the capacitive based pressure sensor determines the upward forces based on if the distance between the first plate and the second plate is greater than the baseline distance and the capacitive based pressure sensor determines the downward forces if the distance between the first plate and the second plate is less than the baseline distance;
wherein the capacitive based pressure sensor distinguishes between upward forces to the pedal through the shoe and downward forces to the pedal through the shoe;
an accelerometer incorporated into the shoe that senses a direction of a force exerted on the pedal; and
a wireless transmitter incorporated into the shoe that transmits measurements of the capacitive based pressure sensor to the computing device;
wherein the computing device comprises a processor and memory, wherein the memory includes non-transitory programmed instructions containing computer instructions store therein, which when accessed by the processor cause the processor to:
quantify the force based at least in part on the measurements of the capacitive based pressure sensor; and
quantify a calorie count based at least in part on the measurements of the capacitive based pressure sensor; and
wherein the shoe further comprises an energy harvesting mechanism that supplies two or more of the capacitive based pressure sensor, the accelerometer, the wireless transmitter, and the processor and memory with electrical power, the energy harvesting mechanism including a reciprocating element and a stationary element, where the reciprocating element induces an electric current upon moving relative to the stationary element.

18. The monitoring system of claim 17, wherein the measurements are at least temporarily stored in a shoe memory.

19. The monitoring system of claim 18, wherein the shoe includes a shoe processor and the shoe memory includes shoe programmable instructions that cause the shoe processor to at least partially process the measurements stored in the shoe memory before the measurements are transmitted to the computing device.

20. The monitoring system of claim 19, wherein the shoe processor compresses the measurements before the measurements are transmitted to the computing device.

* * * * *